US006383790B1

(12) United States Patent
Shokat

(10) Patent No.: US 6,383,790 B1
(45) Date of Patent: May 7, 2002

(54) HIGH AFFINITY PROTEIN KINASE INHIBITORS

(75) Inventor: Kevan M. Shokat, San Francisco, CA (US)

(73) Assignee: Princeton University, Princeton, NJ (US)

( * ) Notice: Subject to any disclaimer, the term of this patent is extended or adjusted under 35 U.S.C. 154(b) by 0 days.

(21) Appl. No.: 09/480,993

(22) Filed: Jan. 11, 2000

Related U.S. Application Data
(60) Provisional application No. 60/115,340, filed on Jan. 11, 1999, and provisional application No. 60/145,422, filed on Jul. 23, 1999.

(51) Int. Cl.[7] .......................... C12N 9/12; C12N 9/99; C07D 487/00; A61K 31/52
(52) U.S. Cl. ...................... 435/194; 435/184; 544/262; 514/261
(58) Field of Search ................................. 435/184, 194; 544/262; 514/261

(56) References Cited

U.S. PATENT DOCUMENTS 5,593,997 A    1/1997  Dow et al. ................... 514/258

FOREIGN PATENT DOCUMENTS

WO    WO-9814211 A1  *  4/1998

OTHER PUBLICATIONS

Gimsa et al., "Inhibitors of Src–Family Tyrosine Kinases Favour Th2 Differentiation" (Mar., 1999) Cytokine, 11(3), 208–215.*
Zhu et al., "Structural Analysis of the Lymphocyte–Specific Kinase Lck in Complex with Non–Selective and Src–Family Selective Kinase Inhibitors" (Jun., 1999) Structure, 7(6), 651–661.*
Bishop et al., 1997, Acquisition of Inhibitor–Sensitive Protein Kinases Through Protein Design, *Pharmacol. Ther.*, 82, 337–346.
Bishop et al., 1998, Design of Allele–Specific Inhibitors to Probe Protein Kinase Signaling. *Current Biology*, 8, 257–266.
Bishop et al., 1999, Generation of Monospecific Namomolar Tyrosine Kinase Inhibitors via a Chemical Genetic Approach. *J. Am. Chem. Soc.*, 121, 627–631.
Bolen et al., 1992, The Src Family of Tyrosine Protein Kinases in Hemopoietic Signal Transduction. *FASEB*, 6: 3403.
Brown et al., 1996, Regulation, Substrates and Functions of Src. *Biochimica Biophys. Acta* 1287, 121–149.
Brugge et al., 1977, Identification of a Transformation–Specific Antigen Induced by an Avian Sarcoma Virus. *Nature*, 269:346.
Cohen et al., 1995, Modular Binding Domains in Signal Transduction Proteins. *Cell* ,80: 237.

Espinoza et al., 1994, Cell Cycle Control by a Complex of the Cyclin HCS26 (PCL1) and the Kinase PHO85. *Science* 266, 1388–1391.
Faltynek et al., 1995, Damnacanthal is a Highly Potent, Selective Inhibitor of $p56^{lck}$ Tyrosine Kinase Activity. *Biochemistry*, 34:12404.
Hanefeld et al., 1996, One–Pot Synthesis of Tetrasubstituted pyrazoles—Proof of Regiochemistry. *J. Chem. Soc., Perkin Trans* 1: 1545–1552.
Hanke et al., 1996, Discovery of a Novel, Potent, and Src Family–Selective Tyrosine Kinase Inhibitor. *J. Biol. Chem.* 271: 695.
Hanks et al., 1991, Protein Kinase Catalytic Domain Sequence Database: Identification of Conserved Features of Primary Structure and Classification of Family Members. *Meth. Enzymol.* 200, 38–81.
Hunter et al., 1987, A Thousand and One Protein Kinases. *Cell*, 50: 823.
Hunter et al., 1995, Protein Kinases and Phosphatases: The Yin and Yang of Protein Phosphorylation and Signaling. *Cell*, 80: 225.
Kelly, 1991. Calmodulin–Dependent Protein Kinase II. *Mol. Neurobiol.* 5 , 153–177.
Laneuvill, 1995. Abl Tyrosine Protein Kinase. *Semin. Immunol.* 7, 255–266.
Liu et al., 1998, Engineering Src Family Kinases with Unnatural Nucleotide Spcificity. *Chemistry & Biology*, 5:91.
Liu et al., 1999, Structural Basis for Selective Inhibition of Scr Family Kinases by PP1. *Chem. & Biol.* 6, 671–678.
Liu et al., 1998, A Molecular Gate which Controls Unnatural ATP Analogue Recognition by the Tyrosine Kinase V–Src. *Bioorganic & Medicinal Chemistry*, 6, 1219–1226.
Mayer et al., 1994, Mutagenic Analysis of the Roles of SH2 and SH3 Domains in Regulation of the Abl Tyrosine Kinase. *Mol. Cell. Bio.* 14: 2883.
Mayer et al.,1992, Point Mutations in the Able SH2 Domain Coordinately Impair Phosphotyrosine Binding In Vitro. *Mol. Cell. Bio.* 12:609.

(List continued on next page.)

*Primary Examiner*—Jon P. Weber
(74) *Attorney, Agent, or Firm*—Morgan, Lewis & Bockius, LLP

(57) ABSTRACT

This invention provides general methods for discovering mutant inhibitors for any class of enzymes as well as the specific inhibitors so identified. More specifically, this invention provides general methods for discovering specific inhibitors for multi-substrate enzymes. Examples of such multi-substrate enzymes include, but are not limited to, kinases and transferases. The mutant inhibitors identified by the methods of this invention can be used to highly selectively disrupt cell functions such as oncogenic transformation. In one particular example, this invention provides a Src protein kinase inhibitor, pharmaceutical compositions thereof and methods of disrupting transformation in a cell that expresses the target v-scr comprising contacting the cell with the protein kinase inhibitor.

60 Claims, 37 Drawing Sheets

OTHER PUBLICATIONS

Measday et al., 1994, The PCL2 (ORFD)–PHO85 Cyclin–Dependent Kinase Complex: A Cell Cycle Regulator in Yeast. *Science* 266, 1391–1395.

Morgan, 1995, Principles of CDK Regulation. *Nature* 374, 131–134.

Omura et al., 1995, Staurosporine, a Potentially Important Gift from a Microorganism. *J. Antibiot.* 48, 535–548.

Resh, 1998, Fyn, a Src Family Tyrosine Kinase. *Int. J. Biochem. & Cell Biol.* 30, 1159–1162.

Shah et al., 1997, Engineering Unnatural Nucleotide Specificity for Rous Sarcoma Virus Tyrosine Kinase to Uniquely Label its Direct Substrates. *Proc. Natl. Acad. Sci.*, 94:3565.

Tapley et al., 1992, K252a Is a Selective Inhibitor of the Tyrosine Protein Activity of the trk Family of Oncogenes and Neurotrophin Receptors. *Oncogene* 7, 371–381.

Taylor et al., 1993, The Cell Cycle and C–Src. *Curr. Opin. Genet. Dev.* 3:26.

Waksman et al., 1993, Binding of a High Affinity Phosphotyrosyl Peptic to the Src SH2 Domain: Crystal Structures of the Complexed and Peptide–free Forms. *Cell*, 72:779.

Waksman et al., 1992, Crystal Structure of the Phosphotyrosine Recognition Domain SH2 of V–Src Complexed with Tyrosine–Phosphorylated Peptides. *Nature*, 358:646.

Waltenberger et al., 1999. A Dual Inhibitor of Platelet–Derived Growth Factor $\beta$–Receptor and Src Kinases Activity Potently Interferes with Motogenic and Mitogenic Responses to PDGF in Vascular Smooth Muscle Cells. *Circ. Res.* 85, 12–21.

Wood et al., 1997, Design and Implementation of an Efficient Synthetic Approach to Furanosylated Indolocarbazoles: Total Synthesis of (+)–and (–)–K252a. *J. Am. Chem. Soc.* 119, 9641–9651.

Wood et al., 1999, Total Synthesis and Protein Kinase Activity of C(7) Methyl Derivatives of K252a. *Synthesis*SI, 1529–1533.

Xu et al., 1995, Substrate Specificities of the Insulin and Insulin–like Growth Factor 1 Receptor Tyrosine Kinase Catalytic Domains. *J. Biol. Chem.* 270:29825.

Yu et al., 1992, Solution Structure of the SH3 Domain of Src and Identification of its Ligand–Binding Site. *Science*, 258:1665.

\* cited by examiner

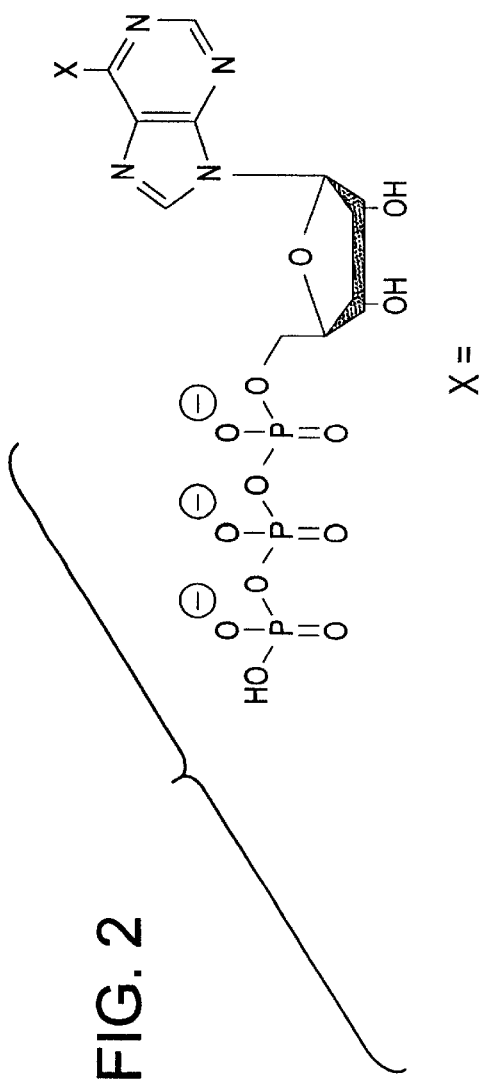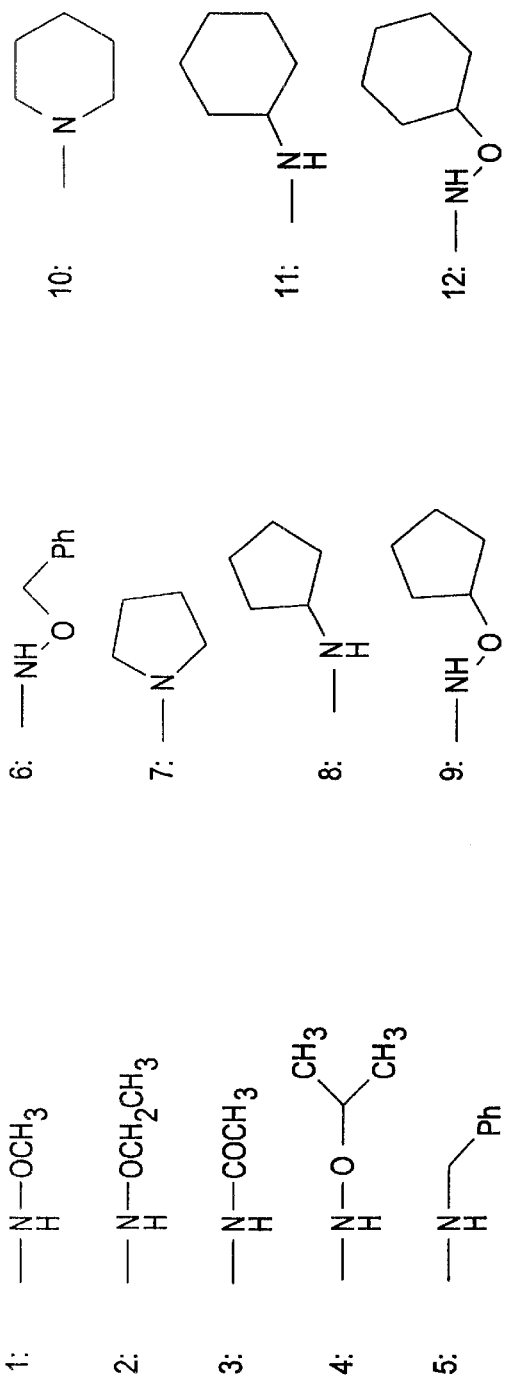
FIG. 2

FIG. 5A
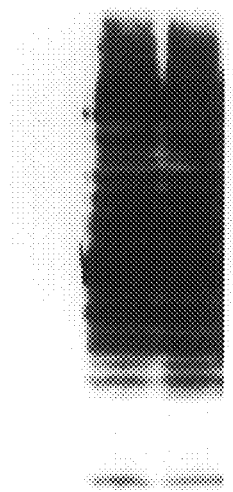
Lanes: 1 uninfected, 2 6-His-XD4, 3 6-His-XD4 (V323A, I338A)
1  2  3
FIG. 5B
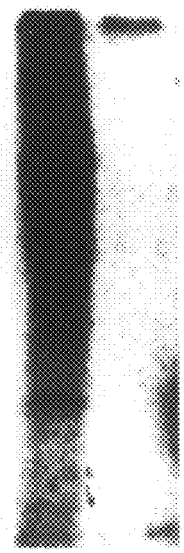
Lanes: 1 CF + [γ-$^{32}$P] ATP, 2 CF + [γ-$^{32}$P] N$^6$-Cyclopentyl ATP
1  2
FIG. 5C
Lanes: 1 GST-XD4, 2 GST-XD4 (V323A, I338A), 3 GST-XD4, 4 GST-XD4 (V323A, I338A)
[γ-$^{32}$P] ATP    [γ-$^{32}$P] A*TP(8)
← autophosphorylated kinase
1  2    3  4

$[\gamma\text{-}^{32}P]$ ATP

I338A   I338S $[\gamma\text{-}^{32}P]$ $N^6$-cyclopentyl ATP

I338A   I338S $[\gamma\text{-}^{32}P]$ ATP

I338A   I338G $[\gamma\text{-}^{32}P]$ $N^6$-cyclopentyl ATP

I338A   I338G

Damnacanthal

| | IC$_{50}$ (μM) |
|---|---|
| lck | 0.10 |
| fyn | 2.09 |
| src | 0.68 |
| erbB2 | 3.5 |

PP1

| | IC$_{50}$ (μM) |
|---|---|
| lck | 0.005 |
| fyn | 0.006 |
| src | 0.17 |
| hck | 0.020 |
| zap-70 | >100 |
| JAK2 | >50 |
| EGFR | 0.25 |

CGP 57148

| | IC$_{50}$ (μM) |
|---|---|
| bcr-abl | 0.025 |
| EGFR | >100 |
| PDGFR | 0.030 |
| c-src | >100 |
| c-lyn | >100 |
| PKA | >500 |
| cdc2/cyclin | >100 |

FIG. 10A
N-4 Acyl Analogues
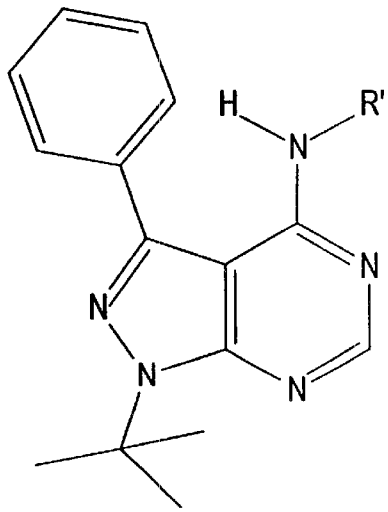
FIG. 10B
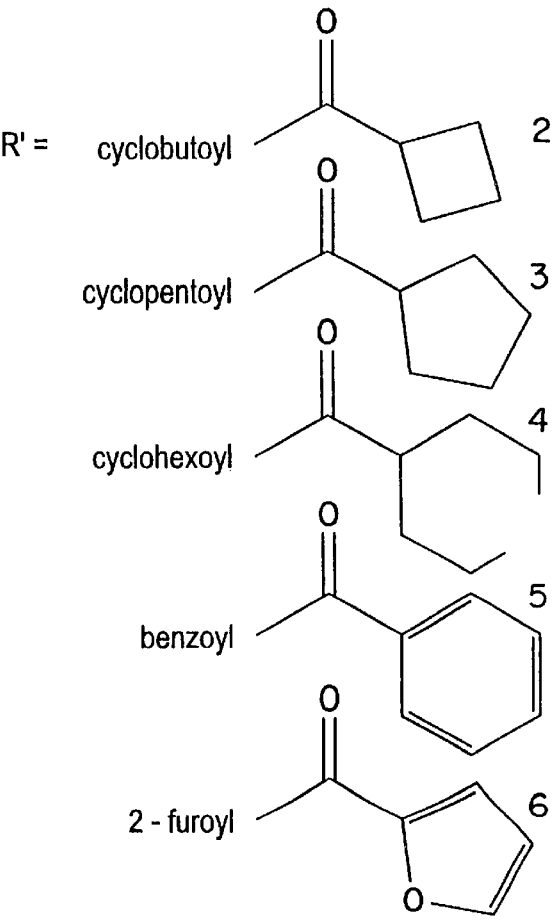
FIG. 10C
In vitro Inhibition Data
| | IC$_{50}$ ($\mu$M) | | |
|---|---|---|---|
| R' = | WT fyn | WT src | I338G src |
| H | 0.08 | 35 | <1 |
| cyclobutoyl | | >>400 | 12 |
| cyclopentoyl | 400 | >>400 | 5 |
| cyclohexoyl | 50 | >>400 | 20 |
| benzoyl | >400 | >>400 | 50 |
| 2 - furoyl | | >>400 | 150 |

FIG. IIA
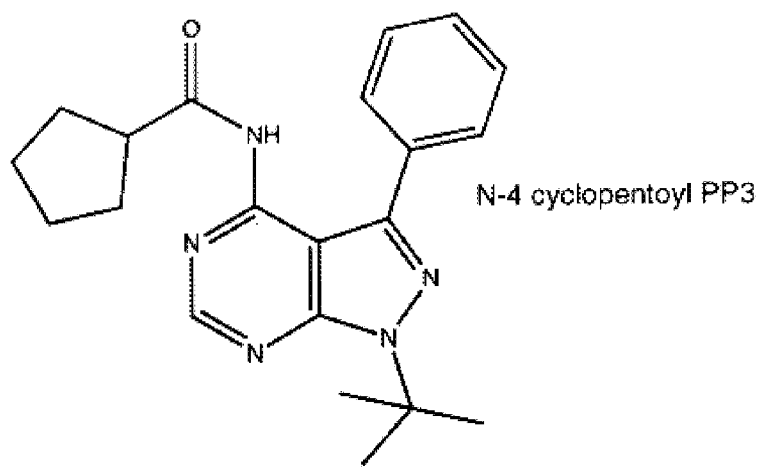
N-4 cyclopentoyl PP3
FIG. IIB
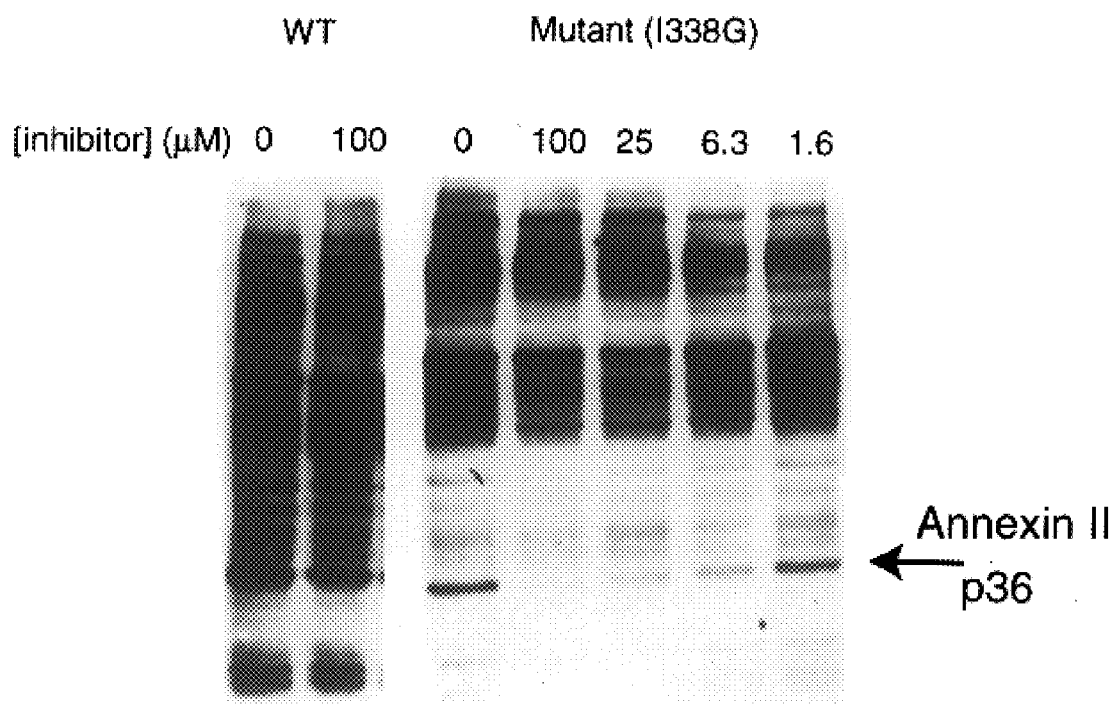

| Molecule | WT XD4 | I338G XD4 | WT Fyn | T339G Fyn | WT Abl | T120A Abl |
|---|---|---|---|---|---|---|
| a | 35 | 0.13 | 0.05 | | | <<10 |
| b | | 200 | >300 | | | |
| c | | 300 | >300 | | | |
| d | | >300 | >300 | | | |
| e | >300 | 75 | >300 | 100 | | >10 |
| f | >300 | 250 | >300 | 26 | | >10 |
| g | >300 | 85 | >300 | 63 | | >10 |
| h | | | | | | |
| i | | | | | | |

FIG. 12B
| | | | | | | | |
|---|---|---|---|---|---|---|---|
| j |  | | | | | | |
| k |  | | | | | | |
| l |  | >300 | 12 | 6.5 | 5 | | |
| m |  | >300 | 19 | 80 | 9 | | |
| n |  | >300 | 20 | 50 | 5 | | |
| o |  | >300 | 150 | 15 | 19 | | |
| p |  | >300 | 10 | 300 | 11 | | <10 |
| q |  | >300 | 10 | 300 | 6 | | <10 |
| r |  | | 1.2 | | | | <10 |
| s |  | | 0.63 | | | | |
| t |  | | <0.411 | | | | 1.8 |
| u |  | >300 | 0.43 | 300 | 0.83 | 300 | <10 |
| v |  | | | | | | |

FIG. 12C
| | | | | | | | |
|---|---|---|---|---|---|---|---|
| w | 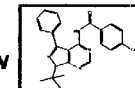 | | | | | | |
| x | 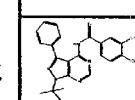 | | | | | | >10 |
| y | 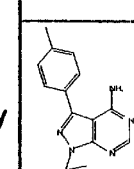 | 100 | <0.05 | 0.1 | | | |
| z | 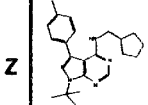 | | >100 | >300 | | | |
| aa | 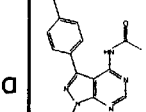 | | | 2 | | | |
| bb | 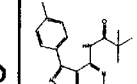 | | | 7 | | | |
| cc | 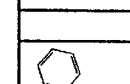 | | | | | | |
| dd |  | | | | | | |
| ee | 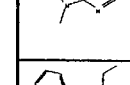 | | | | | | |
| ff | 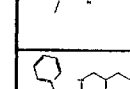 | | | | | | |

FIG. 12D
| | | | | | | | |
|---|---|---|---|---|---|---|---|
| gg | 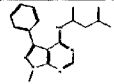 | | | | | | |
| hh | 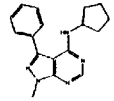 | | | | | | |
| ii | 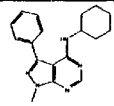 | | | | | | |
| jj | 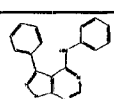 | | | | | | |
| kk | 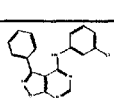 | | | | | | |
| ll | 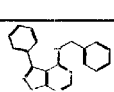 | | | | | | |
| mm | 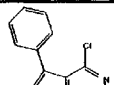 | | | | | | |
| nn | 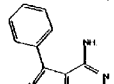 | >1000 | 0.510 | 0.4 | | <<6.5 | |
| oo | 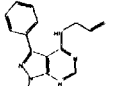 | >300 | >10 | >300 | | | |
| pp | 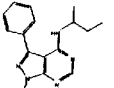 | >300 | >10 | >300 | | | |

FIG. 12E

| | | | | | | | |
|---|---|---|---|---|---|---|---|
| qq | (structure) | >300 | >10 | >300 | | | |
| rr | (structure) | >300 | >10 | >300 | | | |
| ss | (structure) | >300 | >10 | >300 | | | |
| tt | (structure) | >300 | >10 | >300 | | | |
| uu | (structure) | >300 | >10 | >300 | | | |
| vv | (structure) | >300 | >10 | >300 | | | |
| ww | (structure) | >300 | >10 | >300 | | | |
| xx | (structure) | >300 | >10 | >300 | | | |
| yy | (structure) | | | | | | |

FIG. 12F
| | | | | | | | |
|---|---|---|---|---|---|---|---|
| zz | 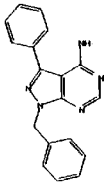 | <10 | 2.5 | <<10 | | | |
| aaa | 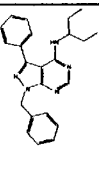 | >300 | >10 | >300 | | | |
| bbb | 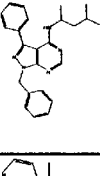 | >300 | >10 | >300 | | | |
| ccc | 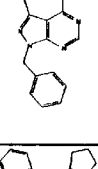 | >300 | >10 | >300 | | | |
| ddd | 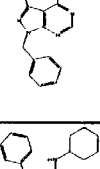 | >300 | >10 | >300 | | | |
| eee | 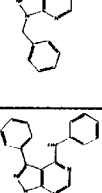 | >300 | >10 | >300 | | | |
| fff |  | >300 | >10 | >300 | | | |

| Cmpd | R= | Cmpd | R= |
|------|-----|------|-----|
| 3a | cyclobutyl | 4b | cyclopentyl |
| 3b | cyclopentyl | 4d | 2 - furyl |
| 3c | cyclohexyl | 4e | phenyl |
| 3d | 2 - furyl | | |
| 3e | phenyl | | |
| 3f | p - methylphenyl | | |
| 3g | p-tert-butylphenyl | | |

FIG. 17C  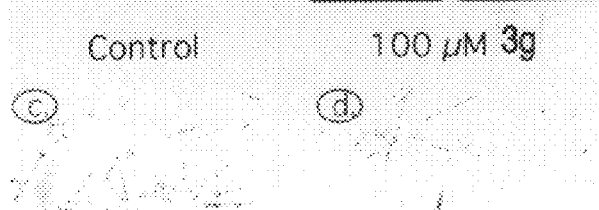 FIG. 17D
FIG. 17E   FIG. 17F
FIG. 17G  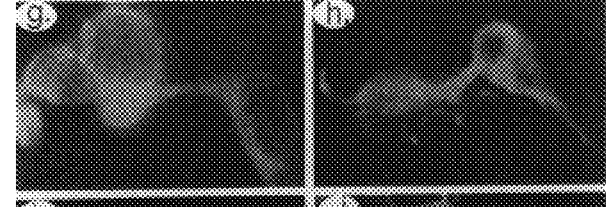 FIG. 17H
FIG. 17I  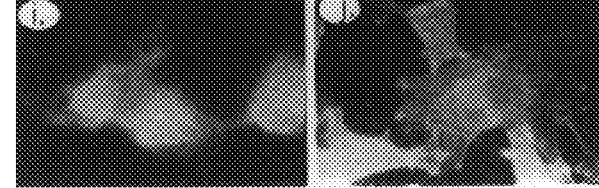 FIG. 17J

FIG. 20A      FIG. 20B
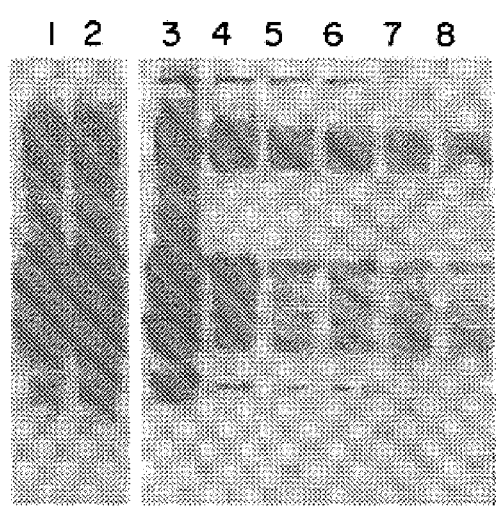

(+)-K252a (1)   (+)-Staurosporine (2)

FIG. 23B
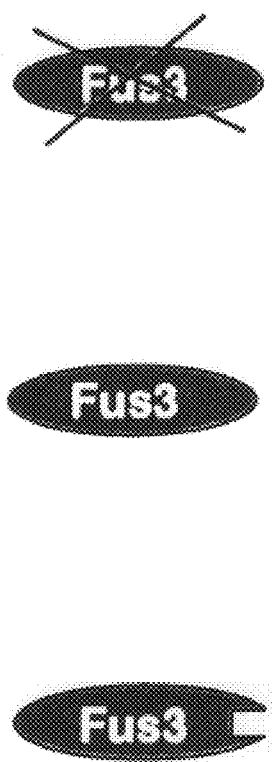
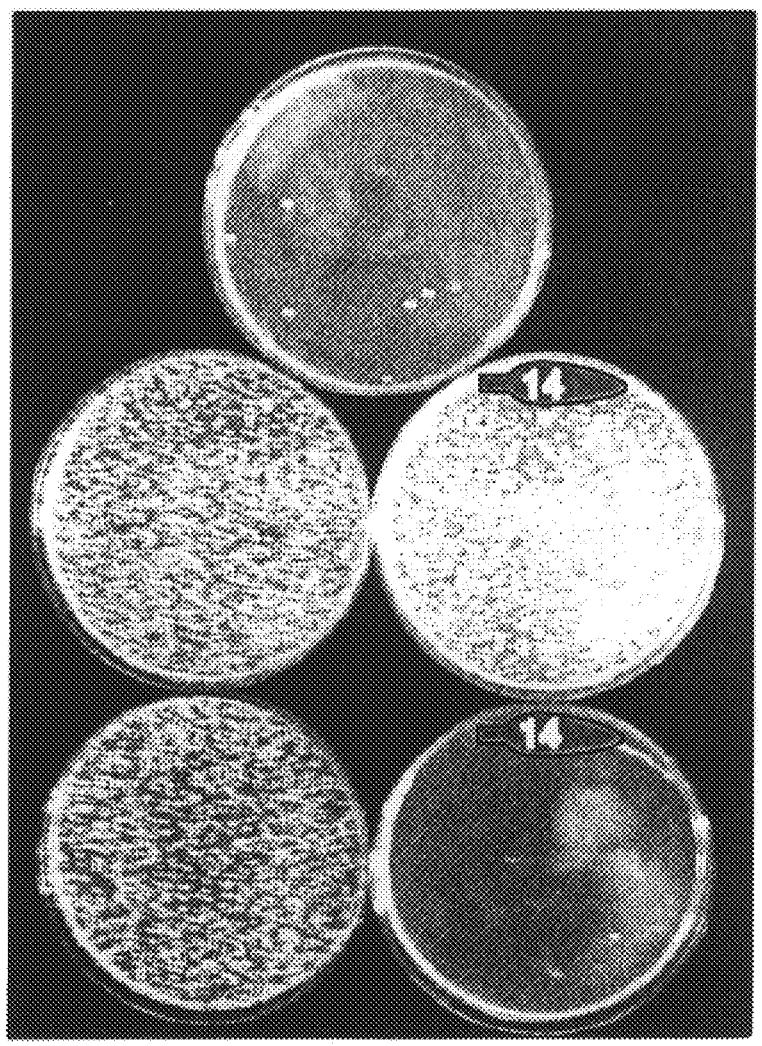

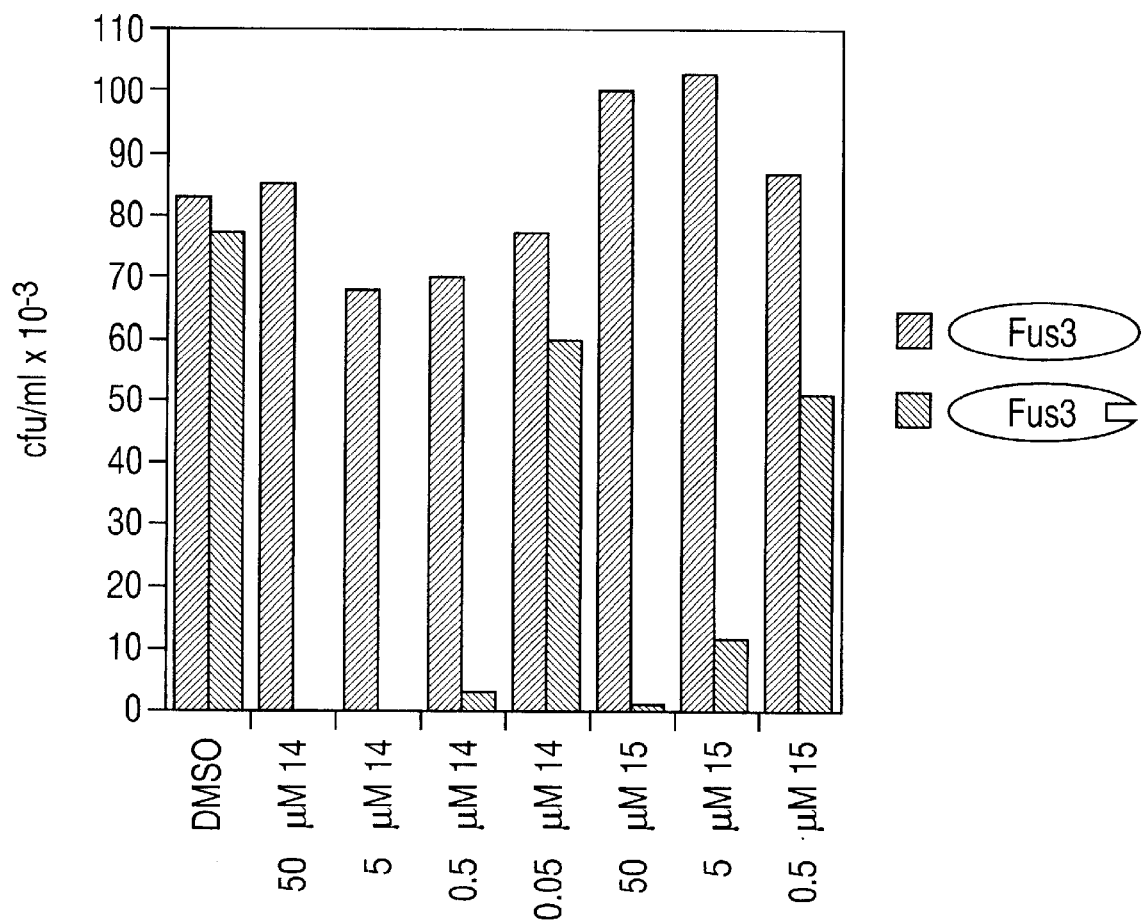

All *S. cerevisiae* genes (6,200)

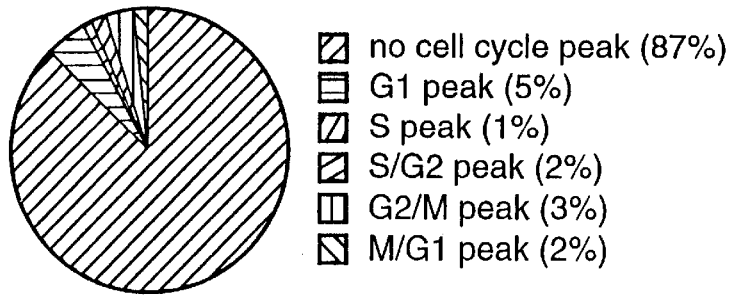

- no cell cycle peak (87%)
- G1 peak (5%)
- S peak (1%)
- S/G2 peak (2%)
- G2/M peak (3%)
- M/G1 peak (2%)

FIG. 25B

Decreases - 120 min (66)

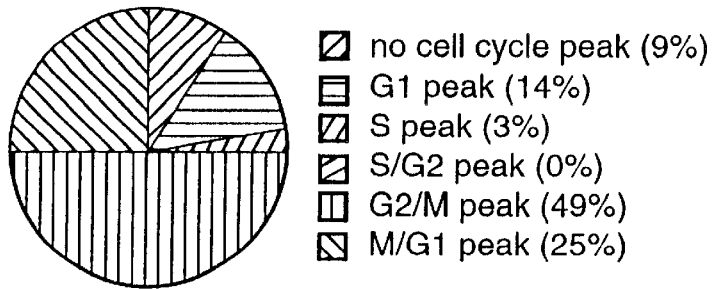

- no cell cycle peak (9%)
- G1 peak (14%)
- S peak (3%)
- S/G2 peak (0%)
- G2/M peak (49%)
- M/G1 peak (25%)

| Unreg | | S | | PHO3 | -21.5 | M/G1 | |
|---|---|---|---|---|---|---|---|
| AMI1 | -3 | HTB2 | -4.6 | PHO5 | -10.6 | AGA2 | -6.5 |
| BAR1 | -5.1 | MET14 | -2.9 | PRY1 | -3.2 | EGT2 | -28.3 |
| PUT4 | -3.2 | | | RPI1 | -2.7 | FAA3 | -4.7 |
| SUN4 | -4.1 | G2/M | | SDL1 | -3.8 | GYP6 | -2.5 |
| YBR077C | -2.6 | ALK1 | -3.5 | SKN1 | -2.5 | IAH2 | -3.4 |
| YER067W | -5.5 | ATF2 | -5.1 | STE2 | -2.5 | ICS4 | -4.7 |
| | | BNS1 | -3.7 | STE6 | -5.8 | MCM3 | -2.6 |
| G1 | | CDC20 | -4.1 | SUR7 | -2.5 | PCL9 | -4.9 |
| CTS1 | -28.4 | CDC5 | -3 | SWI5 | -3.1 | PIR1 | -3.7 |
| GPH1 | -2.9 | CLB2 | -4.1 | UTH1 | -2.5 | PTS1 | -3.5 |
| MFA1 | -3.2 | DBF2 | -2.6 | WSC4 | -6.9 | SPI1 | -2.6 |
| PRY3 | -2.7 | FAR1 | -20.4 | YDR033W | -13.6 | YGP1 | -5.5 |
| RME1 | -3.1 | HST3 | -4.1 | YIL158W | -3.1 | YNL046W | -5.7 |
| RPC10 | -41.2 | MFA2 | -6.9 | YJL051W | -4 | YNR067C | -19.4 |
| SCW11 | -16.4 | MYO1 | -3 | YLR254C | -4.2 | YOR066W | -3.7 |
| YER124C | -9.8 | PHO11 | -4.9 | YML119W | -4.1 | YOR264W | -4.7 |
| YHR218W | -3 | PHO12 | -5.9 | YNL058C | -3.1 | YPL158C | -4.6 |
| | | | | YRO2 | -7.8 | | |

Increases - 120 min (38)

- no cell cycle peak (74%)
- G1 peak (23%)
- S peak (0%)
- S/G2 peak (3%)
- G2/M peak (0%)
- M/G1 peak (0%)

| Unreg | | | | G1 | | S/G2 | |
|---|---|---|---|---|---|---|---|
| BIO3 | 2.6 | YAR068W | 4.5 | CLN2 | 3.3 | ICT1 | 2.6 |
| DIC1 | 2.6 | YBR241C | 3.7 | CSI2 | 3.2 | | |
| ERR1 | 2.5 | YCR059C | 2.5 | PCL1 | 4.7 | | |
| GSC2 | 3.2 | YEL070W | 3 | PRY2 | 3 | | |
| GUT2 | 3.9 | YFL061W | 3.2 | SRO4 | 2.9 | | |
| HEM13 | 2.8 | YGL081W | 2.8 | YLL012W | 2.6 | | |
| MAL1 | 4.1 | YGL170C | 3.5 | YLR326W | 4 | | |
| MRP20 | 2.7 | YHR214W-A | 2.8 | YNL300W | 2.5 | | |
| NGR1 | 3.5 | YIL169C | 20.1 | YPS4 | 3.4 | | |
| PES4 | 3.1 | YLR042C | 6.1 | | | | |
| SKM1 | 2.7 | YMR103C | 2.7 | | | | |
| SPO11 | 5.9 | YMR107W | 3.5 | | | | |
| THI13 | 2.6 | YOR343C | 3.3 | | | | |
| THI21 | 2.5 | YPL280W | 3.1 | | | | |

FIG. 26A

| Protein Kinase | Kinase Family | Specificity | Cellular Function |
|---|---|---|---|
| v-Src | Src | Tyr | oncogenic transformation |
| c-Fyn | Src | Tyr | lymphocyte activation |
| c-Abl | Abl | Tyr | F-actin binding, transcription |
| CAMK II | calcium/calmodulin dependent | Ser/Thr | long-term potentiation, memory |
| CDK2 | cyclin dependent | Ser/Thr | mammalian cell cycle progression |
| CDC28 | cyclin dependent | Ser/Thr | S. cerevisiae cell cycle progression |
| Fus3 | mitogen-activated | Ser/Thr | S. cerevisiae mating |

FIG. 26B

```
                               338
                                ▼
v-Src  (318) RHEKLVQLYAMVSE---------EPIYIVIEYMSK--GSLLDFLKGEMGKY
Fyn    (319) KHDKLVQLYAVVSE---------EPIYIVTEYMNK--GSLLDFLKDGEGRA
Abl    (294) KHPNLVQLLGVCTRE--------PPFYIITEFMTY--GNLLDYLRECNRQE
CamK II (68) KHPNIVRLHDSISEE--------GHHYLIFDLVTG--GELFEDIVAREY
Cdk2    (59) NHPNIVKLLDVIHTE--------NKLYLVFEFLHQ---DLKKFMDASALTG
Cdc28   (66) KDDNIVRLYDIVHSDA-------HKLYLVFEFLDL---DLKRYMEGIPKDQP
Fus3    (67) KHENIITIFNIQRPDSFENF---NEVYIIQELMQT---DLHRVISTQM
```

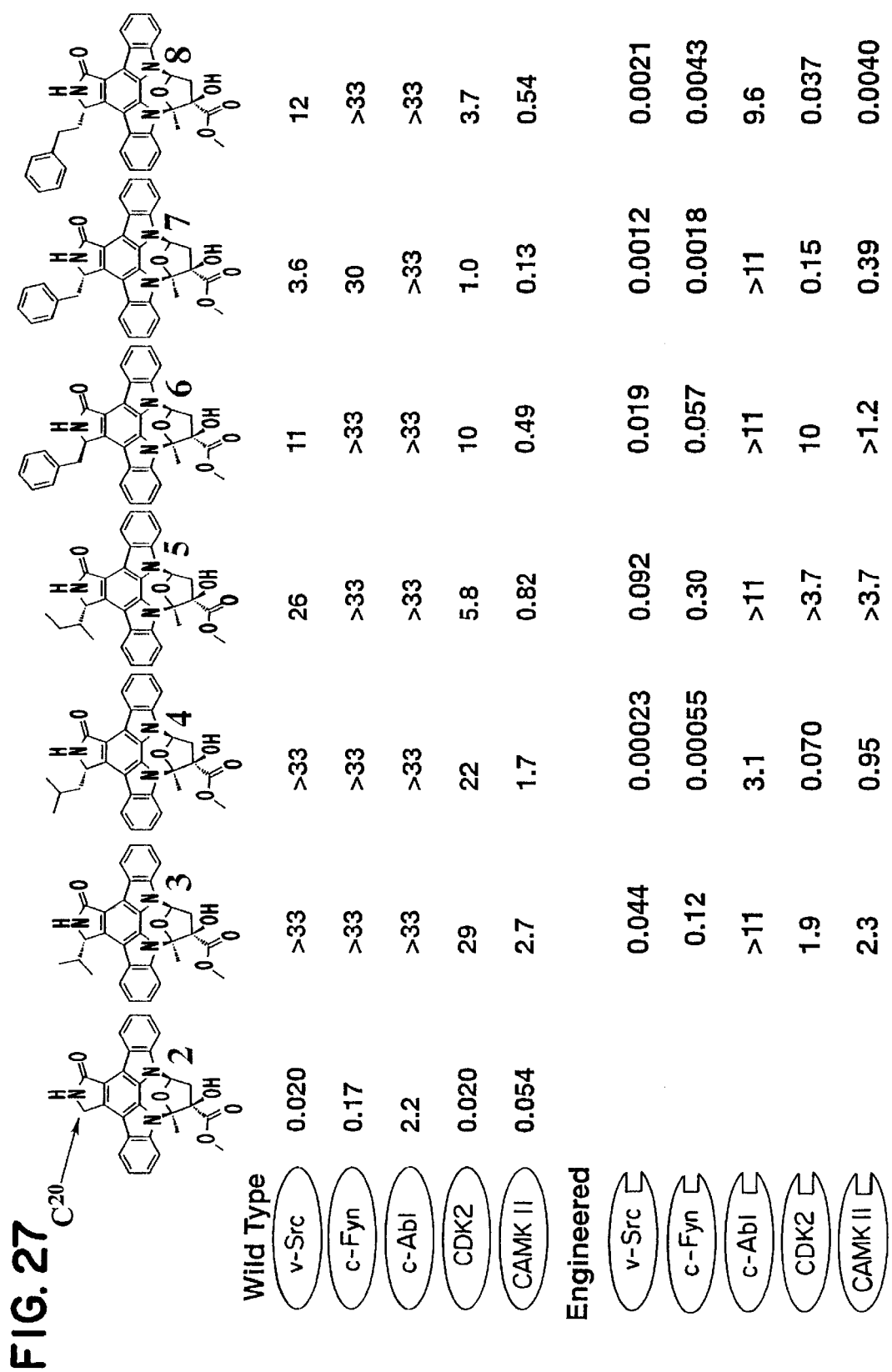

| | 9 | 10 | 11 |
|---|---|---|---|
| Wild Type | | | |
| v-Src | 2.2 | 1.0 | 28 |
| c-Fyn | 0.050 | 0.60 | 1.0 |
| c-Abl | 0.30 | 0.60 | 3.4 |
| CDK2 | 22 | 18 | 29 |
| CAMKII | 17 | 22 | 24 |
| Engineered | | | |
| v-Src | | 0.0015 | 0.0043 |
| c-Fyn | | 0.0065 | 0.0032 |
| c-Abl | | 0.0070 | 0.12 |
| CDK2 | | 0.015 | 0.0050 |
| CAMKII | | 0.097 | 0.0080 | ns

SEQUENCE LISTING

<160> NUMBER OF SEQ ID NOS: 20

<210> SEQ ID NO 1
<211> LENGTH: 27
<212> TYPE: PRT
<213> ORGANISM: Homo sapiens

<400> SEQUENCE: 1

Asn Phe Pro Phe Leu Val Lys Leu Glu Phe Ser Phe Lys Asp Asn Ser
 1               5                   10                  15

Asn Leu Tyr Met Val Met Glu Tyr Val Pro Gly
            20                  25

<210> SEQ ID NO 2
<211> LENGTH: 27
<212> TYPE: PRT
<213> ORGANISM: Rous sarcoma virus

<400> SEQUENCE: 2

Asn His Pro Asn Ile Val Lys Leu Leu Asp Val Ile His Thr Glu Asn
 1               5                   10                  15

Lys Leu Tyr Leu Val Phe Glu Phe Leu His Gln
            20                  25

<210> SEQ ID NO 3
<211> LENGTH: 26
<212> TYPE: PRT
<213> ORGANISM: Rous sarcoma virus

<400> SEQUENCE: 3

Arg His Glu Lys Leu Val Gln Leu Tyr Ala Val Val Ser Glu Glu Pro
 1               5                   10                  15

Ile Tyr Ile Val Ile Glu Tyr Met Ser Lys
            20                  25

<210> SEQ ID NO 4

```
<211> LENGTH: 30
<212> TYPE: DNA
<213> ORGANISM: Rous sarcoma virus

<400> SEQUENCE: 4
tttggatcca tggggagtag caagagcaag                                    30

<210> SEQ ID NO 5
<211> LENGTH: 30
<212> TYPE: DNA
<213> ORGANISM: Rous sarcoma virus

<400> SEQUENCE: 5
tttgaattcc tactcagcga cctccaacac                                    30

<210> SEQ ID NO 6
<211> LENGTH: 26
<212> TYPE: DNA
<213> ORGANISM: Rous sarcoma virus

<400> SEQUENCE: 6
tgagaagctg gctcaactgt acgcag                                        26

<210> SEQ ID NO 7
<211> LENGTH: 26
<212> TYPE: DNA
<213> ORGANISM: Rous sarcoma virus

<400> SEQUENCE: 7
ctgcgtacag ttgagccagc ttctca                                        26

<210> SEQ ID NO 8
<211> LENGTH: 24
<212> TYPE: DNA
<213> ORGANISM: Rous sarcoma virus

<400> SEQUENCE: 8
ctacatcgtc gctgagtaca tgag                                          24

<210> SEQ ID NO 9
<211> LENGTH: 24
<212> TYPE: DNA
<213> ORGANISM: Rous sarcoma virus

<400> SEQUENCE: 9
ctcatgtact cagcgacgat gtag                                          24

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence:  Imaginary
      sequence for enzyme modelling

<400> SEQUENCE: 10

Asp Met Phe Arg Asp Lys Glu
 1               5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence:  Imaginary
```

-continued sequence for enzyme modelling

<400> SEQUENCE: 11

Asp Met Ile Arg Glu Lys Asp
 1               5

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence:  Optimized
      substrate for src kinases

<400> SEQUENCE: 12

Ile Tyr Gly Glu Phe Lys Lys Lys
 1               5

<210> SEQ ID NO 13
<211> LENGTH: 12
<212> TYPE: PRT
<213> ORGANISM: Artificial Sequence
<220> FEATURE:
<223> OTHER INFORMATION: Description of Artificial Sequence:  Optimized
      substrate for Abl

<400> SEQUENCE: 13

Glu Ala Ile Tyr Ala Ala Pro Phe Ala Lys Lys Lys
 1               5                  10

<210> SEQ ID NO 14
<211> LENGTH: 40
<212> TYPE: PRT
<213> ORGANISM: Rous sarcoma virus
<220> FEATURE:
<223> OTHER INFORMATION: v-Src kinase

<400> SEQUENCE: 14

Arg His Glu Lys Leu Val Gln Leu Tyr Ala Met Val Ser Gly Glu Pro
 1               5                  10                  15

Ile Tyr Ile Val Ile Glu Tyr Met Ser Lys Gly Ser Leu Leu Asp Phe
            20                  25                  30

Leu Lys Gly Glu Met Gly Lys Tyr
        35                  40

<210> SEQ ID NO 15
<211> LENGTH: 40
<212> TYPE: PRT
<213> ORGANISM: Homo sapiens
<220> FEATURE:
<223> OTHER INFORMATION: c-Fyn kinase

<400> SEQUENCE: 15

Lys His Asp Lys Leu Val Gln Leu Tyr Ala Val Val Ser Glu Glu Pro
 1               5                  10                  15

Ile Tyr Ile Val Thr Glu Tyr Met Asn Lys Gly Ser Leu Leu Asp Phe
            20                  25                  30

Leu Lys Asp Gly Glu Gly Arg Ala
        35                  40

<210> SEQ ID NO 16
<211> LENGTH: 41
<212> TYPE: PRT
<213> ORGANISM: Homo sapiens
<220> FEATURE:

-continued

<223> OTHER INFORMATION: c-Abl kinase

<400> SEQUENCE: 16

Lys His Pro Asn Leu Val Gln Leu Leu Gly Val Cys Thr Arg Glu Pro
1               5                   10                  15

Pro Phe Tyr Ile Ile Thr Glu Phe Met Thr Tyr Gly Asn Leu Leu Asp
            20                  25                  30

Tyr Leu Arg Glu Cys Asn Arg Gln Glu
        35                  40

<210> SEQ ID NO 17
<211> LENGTH: 39
<212> TYPE: PRT
<213> ORGANISM: Homo sapiens
<220> FEATURE:
<223> OTHER INFORMATION: CamK II, calcium/calmodulin-dependent kinase

<400> SEQUENCE: 17

Lys His Pro Asn Ile Val Arg Leu His Asp Ser Ile Ser Glu Glu Gly
1               5                   10                  15

His His Tyr Leu Ile Phe Asp Leu Val Thr Gly Gly Glu Leu Phe Glu
            20                  25                  30

Asp Ile Val Ala Arg Glu Tyr
        35

<210> SEQ ID NO 18
<211> LENGTH: 40
<212> TYPE: PRT
<213> ORGANISM: Homo sapiens
<220> FEATURE:
<223> OTHER INFORMATION: Cdk2, cyclin-dependent kinase

<400> SEQUENCE: 18

Asn His Pro Asn Ile Val Lys Leu Leu Asp Val Ile His Thr Glu Asn
1               5                   10                  15

Lys Leu Tyr Leu Val Phe Glu Phe Leu His Gln Asp Leu Lys Lys Phe
            20                  25                  30

Met Asp Ala Ser Ala Leu Thr Gly
        35                  40

<210> SEQ ID NO 19
<211> LENGTH: 42
<212> TYPE: PRT
<213> ORGANISM: Saccharomyces cerevisiae
<220> FEATURE:
<223> OTHER INFORMATION: Cdc28, cyclin-dependent kinase

<400> SEQUENCE: 19

Lys Asp Asp Asn Ile Val Arg Leu Tyr Asp Ile Val His Ser Asp Ala
1               5                   10                  15

His Lys Leu Tyr Leu Val Phe Glu Phe Leu Asp Leu Asp Leu Lys Arg
            20                  25                  30

Tyr Met Glu Gly Ile Pro Lys Asp Gln Pro
        35                  40

<210> SEQ ID NO 20
<211> LENGTH: 42
<212> TYPE: PRT
<213> ORGANISM: Saccharomyces cerevisiae
<220> FEATURE:
<223> OTHER INFORMATION: Fus3, mitogen-activated kinase

<400> SEQUENCE: 20

```
Lys His Glu Asn Ile Ile Thr Ile Phe Asn Ile Gln Arg Pro Asp Ser
 1               5                  10                  15

Phe Glu Asn Phe Asn Glu Val Tyr Ile Ile Gln Glu Leu Met Gln Thr
             20                  25                  30

Asp Leu His Arg Val Ile Ser Thr Gln Met
         35                  40
```

HIGH AFFINITY PROTEIN KINASE INHIBITORS

CROSS REFERENCES TO RELATED APPLICATIONS

This application claims priority to U.S. Provisional Patent Application No. 60/115,340, filed on Jan. 11, 1999, and U.S. Provisional Patent Application No. 60/145,422, filed on Jul. 23, 1999, both applications which are hereby incorporated by reference in their entirety.

FEDERALLY SPONSORED RESEARCH

The research leading to the present invention was supported in part by the grant NIH(IROIICA70331-0) and NIH(IROIAI/CA44009-01) from the National Institute of Health. The government may have certain rights in the present invention.

FIELD OF THE INVENTION

This invention provides general methods for discovering mutant inhibitors for any class of enzymes as well as the specific inhibitors so identified. More specifically, this invention provides general methods for discovering specific inhibitors for multi-substrate enzymes. Examples of such multi-substrate enzymes include, but are not limited to, kinases and transferases. The mutant inhibitors identified by the methods of this invention can be used to highly selectively disrupt cell functions such as oncogenic transformation. In one particular example, this invention provides a Src protein kinase inhibitor, pharmaceutical compositions thereof and methods of disrupting transformation in a cell that expresses the target v-Src comprising contacting the cell with the protein kinase inhibitor.

BACKGROUND OF THE INVENTION

All publications and patent applications herein are incorporated by reference to the same extent as if each individual publication or patent application was specifically and individually indicated to be incorporated by reference. U.S. patent application Ser. Nos. 08/797,522 and 60/046,727, and PCT/US98/02522 are related to the present invention and each of these applications is specifically and individually incorporated by reference in its entirety.

The current explosion in the number of newly discovered genes underscores the need for small molecule ligands which can be used to elucidate and control gene function. Convergent engineering of protein/small molecule interfaces has emerged in recent years as a powerful method for generating novel ligand/receptor pairs with high specificity. By introducing chemical diversity into the target protein as well as the small molecule, unique binding interactions can be designed and exploited more efficiently than through traditional medicinal chemistry. Such approaches have been used to chemically explore a number of biological systems. FK506-binding protein has been engineered to preferentially bind non-natural FK506 analogues by Schreiber and co-workers, as well as Clackson and co-workers. This system has been used extensively to selectively dimerize receptors and control gene expression in a cellular context. Nuclear hormone receptors have also been shown to be amendable to chemical genetic design. Corey and co-workers demonstrated that mutations at two amino acid residues in the retinoid X receptor are sufficient to create two new classes of receptors with novel ligand specificities. In a more medicinally applicable system, Smith and co-workers engineered the protease, carboxypeptidase A1, to hydrolyze a prodrug of methotrexate which is resistant to hydrolysis by wild type proteases.

Protein kinase catalyzed phosphorylation of the hydroxyl moiety of serine, threonine or tyrosine is the central post-translational control element in eukaryotic signal transduction. The phosphorylation state of a given protein can govern its enzyme activity, protein-protein binding interactions, and cellular distribution. Phosphorylation and dephosphorylation is thus a "chemical switch" which allows the cell to transmit signals from the plasma membrane to the nucleus to ultimately control gene expression in a highly regulated manner. Highly selective, cell permeable inhibitors of individual kinases would allow for the systematic investigation of the cellular function of a kinase in real time, and thus, would provide invaluable tools for the deconvolution of phosphorylation dependent processes in signal transduction cascades.

The Src family is composed of ten highly homologous cytosolic kinases which are critical components in an array of cell signaling pathways ranging from lymphocyte activation to cell growth and proliferation. Constitutive activation of these enzymes can lead to oncogenic cell transformation, making them putative drug targets for cancer therapies. Because of their importance in the regulation of these fundamental cellular processes, many studies have focused on developing inhibitors for the Src family kinase. However, the potent inhibitors that have been discovered lack the high selectivity that would be required for probing the cellular inhibition of an individual target kinase. Conventional inhibitor screens have produced few if any molecules which can discriminate between the active sites of the various Src family kinases.

Unfortunately, the very features which make kinases so useful in signal transduction, and which has made them evolve to become central to almost every cellular function, also makes them extremely difficult, if not impossible, to study and understand. Their overlapping protein specificities, their structural and catalytic similarities, their large number, and their great speed make the specific identification of their in vivo protein substrates extremely difficult, if not impossible, using current genetic and biochemical techniques. This is today the main obstacle to deciphering the signaling cascades involved in protein kinase-mediated signal transduction (4,6–8).

Efforts to dissect the involvement of specific protein kinases in signal transduction cascades have been frustrated by their apparent lack of protein substrate specificity in vitro and in vivo (4,8). The catalytic domains of protein kinases possess little or no inherent protein substrate specificity, as demonstrated by domain swapping experiments (18–23). The catalytic domain from one protein kinase can be substituted into a different protein kinase with little change in the protein substrate specificity of the latter (22).

The poor in vitro specificity of kinases also makes it difficult, if not impossible, to extrapolate what the in vivo function of given kinases might be. An isolated protein kinase of interest will often phosphorylate many test substrates with equal efficiency (29). This apparently poor substrate specificity is also found in vivo; for example, many genetic approaches, such as gene knock out experiments, give no interpretable phenotype due to compensation by other cellular protein kinases (30,31).

Another complication is that many protein kinases have been proposed to phosphorylate downstream and upstream proteins which are themselves protein kinases; although this appears to make complex positive feedback loops possible, it also makes dissecting the cascade even more difficult (1). One important avenue for deciphering the role and understanding the function of enzymes, both in vitro and in vivo, is the use of specific enzyme inhibitors. If one or more compound can be found that will uniquely inhibit the protein kinase target, the inhibitor can be used to modulate the enzyme's activity, and the effects of that decrease can be observed. Whole genome techniques have provided many targets but their function is unknown. Many methods have been developed to determine if a given new kinase could be a good target. These methods, all have in common the lack of a small molecule to inhibit the enzyme which can lead to confusion.

For example, the most commonly used state of the art technique is to knock out the kinase and see a new phenotype. Typically, deletion of one kinase in the mouse genome (most common model organism) causes no informative change. This is for two reasons: 1) either the gene kinase) is essential during embryogenesis, thereby causing lethality before birth, or 2) the gene is absent (knocked out) and its function can be replaced by a closely related kinase which is still present. The important difference between the art recognized approach and the invention herein is that herein small organic molecules are employed to inhibit the function of the kinase of interest, since it is still present in the organisms but inactive thus it can cause significant changes to the organisms and most importantly the changes are exactly like that which would occur if an inhibitor of wild-type enzyme was made.

In addition, such inhibitors are among the most important pharmaceutical compounds known. For example, aspirin (acetylsalicylic acid) is such an inhibitor. It inhibits an enzyme that catalyzes the first step in prostaglandin synthesis, thus inhibiting the formation of prostaglandins, which are involved in producing pain (72). Traditional drug discovery can be characterized as the design and modification of compounds designed specifically to bind to and inactivate a disease-causing protein; the relative success of such an effort depends upon the selectivity of the drug for the target protein and its lack of inhibition of non-disease associated enzymes with similar enzyme activities. Such approaches would appear to be promising ways to develop treatments for cancer, since many human cancers are caused by disregulation of a normal protein (e.g., when a proto-oncogene is converted to an oncogene through a gene translocation). And since kinases are key regulators, they have turned out to be very common proto-oncogenes, and thus ideal drug design targets.

The process of designing selective inhibitors is relatively simple in cases where few similar enzymes are present in the target organism, for example in cases where inhibitors of a protein unique to bacteria can be targeted. But unfortunately, the similarities between the kinases and their large number has almost completely frustrated the discovery and design of specific inhibitors, and has blocked most hopes of developing specific pharmaceutical treatments aimed at the proto-oncogene level. It is expected that the vast majority of candidate inhibitors will inhibit multiple kinases, even though they may have initially been identified as inhibiting a particular, purified kinase.

These difficulties described above have implications well beyond the mere frustration of scientists; they have frustrated efforts to decipher the kinase cascades and the function of individual kinases in those cascades and other cellular mechanisms. Such an understanding of kinase activity and function may be essential before certain human diseases can be effectively treated, prevented or cured. For example, it has been known for over 30 years that the oncogene bcr-abl is a protein kinase that is responsible for chronic myelogenous leukemia; but the physiological substrates that it acts upon to cause oncogenesis, which may be important drug design targets, have yet to be definitively identified (11). On the bright side, despite this shortcoming, the inhibitor CGP 57148 is reportedly now undergoing clinical trials for use in treating myelogenous leukemia, even though the substrates it may block phosphorylation of in vivo are not known.

The medical significance of these difficulties is further illustrated by the Rous sarcoma virus (RSV), which has become an important model system for studying the role of kinases in oncogenesis. RSV transformation of fibroblasts is controlled by a single viral gene product, the protein kinase v-src (32). It is the rapid time course and the dramatic morphological changes during RSV fibroblast transformation that have made RSV a paradigm for studies of oncogene activity in all cells. The origin (33), regulation (3,8,34,35), and structure (25,27,36) of v-Src have been extensively studied and are well understood (8,37,38). But central questions about the intensely studied kinase remains unanswered: what are its direct cellular substrates? Does inhibition of its catalytic activity effectively inhibit, or even reverse, transformation? Would such inhibition be an effective therapy for or prophylactic against RSV transformation? Unfortunately, as discussed above, the answers to these questions are not forthcoming, largely because the number of cellular kinases is enormous (it is estimated that 2% of the mammalian genome encodes protein kinases (4)) and because protein kinases display overlapping substrate specificities (8,39) and share catalytic domains, making the design of specific inhibitors enormously difficult.

Although the difficulties are daunting, new methods of rational drug design and combinatorial organic synthesis make the design or discovery of kinase-specific inhibitors feasible given sufficient resources. However, because the kinase networks are highly degenerate and interconnected in unknown ways, there is considerable uncertainty with regard to many diseases which kinases should be targeted for inhibition. Moreover, it is by no means clear that a specific inhibitor of a given kinase will have any effect on the disease, either in vitro or in vivo. Because kinases can be highly promiscuous, there is a significant chance that inhibiting one kinase will simply force another kinase to "take its place."

The present invention provides a strategy (i.e., methodology) of combining chemical and genetic approaches to enable the rapid generation of highly selective small molecule inhibitors for one engineered enzymes, such as kinases and methyltransferases, in vitro and in whole cells. The invention disclosed herein involves using a specific point mutation to create a unique pocket in the substrate binding pocket or site of the enzyme of interest which does not occur in any other enzyme in the genome. A specific inhibitor of the engineered enzyme is then synthesized by derivatizing an enzyme inhibitor with a bulky group designed to fit the novel active site pocket. By using genetic manipulation to introduce a unique structural difference into the conserved enzyme active site, highly selective inhibitors can be identified from very small panels (10 compounds) of putative inhibitors as explained herein. The inhibitors of the present invention are useful for studying the function of enzymes in biochemical pathways as well as for therapeutic purposes.

SUMMARY OF THE INVENTION

This invention provides inhibitors that do not inhibit a catalytic activity of a wild-type enzyme but do inhibit the same catalytic activity of the corresponding mutant enzyme, wherein the wild-type enzyme and the mutant enzyme are functionally identical. More specifically, the inhibitors of the present invention inhibit the catalytic activity of a mutant enzyme with an $IC_{50}$ of less than about 200 nM. The present invention further provides methods of inhibiting a catalytic activity of a mutant enzyme by contacting the mutant enzyme with the inhibitors of this invention.

The present invention provides inhibitors that do not inhibit the growth of a cell expressing a wild-type enzyme but do inhibit the growth of a cell expressing a mutant form of the wild-type enzyme, wherein the wild-type enzyme and the mutant form of the wild-type enzyme are functionally identical. Examples of inhibitors provided by the present invention include, but are not limited to, protein kinase inhibitors, lipid kinase inhibitors, aminoglycoside kinase inhibitors and transferase inhibitors, such as methyltransferase inhibitors. The present invention also provides methods of inhibiting the growth of a cell expressing a mutant enzyme by contacting a cell with the inhibitors of the present invention.

The present invention further provides protein kinase inhibitors represented by the following formula I:

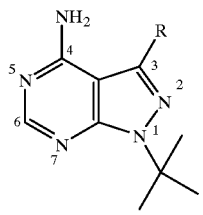

wherein R is a 1'-naphthyl; 2'-napthyl; m-phenoxyphenyl; m-benzyloxyphenyl; m-(2', 6'-dichloro)benzyloxyphenyl; 3-piperonylpyrazolo; p-tert-butylphenyl; 1'-naphthylmethyl; 1'-napthoxymethyl; or 2'-naphthylmethyl. More specifically, the present invention provides such protein kinase inhibitors where R is 1'-naphthyl; 2'-naphthyl or 1'-napthylmethyl; 2'-napthylmethyl. The present invention also provides compositions which include the protein kinase inhibitors of the present invention.

The present invention provides methods of disrupting transformation in a cell that expresses a mutant protein kinase of the Src family by contacting the cell with the protein kinase inhibitors of the present invention. More specifically, the present invention provides methods of disrupting transformation in a cell that expresses I338G v-Src or T339G Fyn by contacting the cell with the protein kinase inhibitors of the present invention.

The present invention further provides methods of disrupting transformation in a cell that expresses a mutant protein kinase of the Src family by contacting the cell with a composition comprising the protein kinase inhibitors of the present invention. More specifically, the present invention provides methods of disrupting transformation in a cell that expresses I338G v-Src or T339G Fyn by contacting the cell with a composition comprising the protein kinase inhibitors of the present invention.

The present invention also provides methods of inhibiting the phosphorylation of a substrate of a mutant protein kinase by incubating a protein kinase inhibitor of the present invention with a mixture containing the mutant protein kinase and its substrate.

The present invention also provides methods of inhibiting the catalytic activity of a mutant enzyme by incubating the mutant enzyme with an inhibitor of the present invention.

The present invention also provides methods of inhibiting the growth of a cell by incubating the cell with an inhibitor of the present invention.

Mutant protein kinases used in the methods of the present invention include, but are not limited to the following: i) mutant protein kinases of the Src family, such as mutant v-Src; ii) mutant Fyn; iii) mutant c-Abl; iv) mutant CAMK IIα; v) mutant CDK2; vi) mutant Cdc28 and vii) mutant Fus3. Specific examples of mutant protein kinases used in the methods of the present invention include, but are not limited to the following: i) I338G v-Src; ii) T339G Fyn; iii) T315A Abl; iv) F89G CAMK IIα; v) F80G CDK2; vi) Cdc28-as1 and vii) Fus-as1.

This invention further provides a general approach for sensitizing protein kinases to cell permeable molecules which do not inhibit any wild-type protein kinases. Using this approach, potent and specific inhibitors from two structural classes of putative inhibitors are identified for seven protein kinases from five distinct sub-families. This approach can be used in vivo to systematically generate conditional alleles of protein kinases.

This invention also provides mutant kinase, Cdc28-as1 (analog-specific 1), that is uniquely sensitive to the cell-permeable inhibitor 4-amino-1-(tert-butyl)-3-(1'-naphthylmethyl)pyrazolo[3,4-d]pyrimidine (1-NM-PP1). In cdc28-as1 cells, entry into mitosis is inhibited by low concentrations of 1-NM-PP 1, whereas higher concentrations of inhibitor are required to induce the G1 arrest that is typically observed in temperature-sensitive cdc28 mutants. Genome-wide transcriptional analysis confirms that 1-NM-PP1 treatment of cdc28-as1 cells leads to inhibition of G2/M-specific gene expression, whereas treatment of wild-type cells has no significant effects. The generation of the analog-specific cdc28-as1 mutant thus provides a highly specific method for inhibiting Cdc28 activity in the cell, and demonstrates the general utility of this method in the analysis of protein kinases.

BRIEF DESCRIPTION OF THE FIGURES

FIG. 2 is a schematic representation of adenosine triphosphate (ATP), with an "X" bound to the $N^6$ position; and in the box below, schematic representations are provided for the twelve side chains that take the place of "X" in each of the orthogonal ATP analogs described in the examples (which are always referred to by the numbers 1–12).

Figure 3:
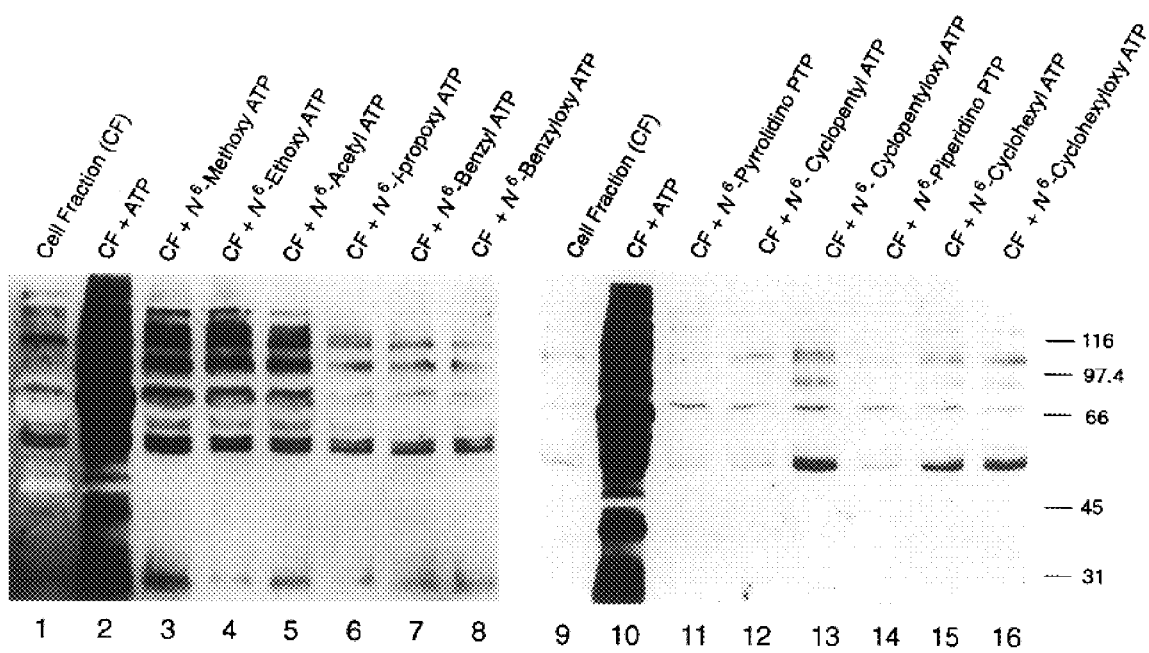

These analogs are:

1- $N^6$(methoxy)ATP
2- $N^6$(ethoxy)ATP
3- $N^6$(acetyl)ATP
4- $N^6$(i-propoxy)ATP
5- $N^6$(benzyl)ATP
6- $N^6$(benzyloxy)ATP
7- $N^6$(pyrolidiono)ATP
8- $N^6$(cyclopenty)ATP
9- $N^6$(cyclopentyloxy)ATP
10- $N^6$(pipperidino)ATP
11- $N^6$(cyclohexyl)ATP
12- $N^6$(cyclohexyloxy)ATP FIG. 3 is an anti-phosphotyrosine immunoblot showing the level of protein tyrosine phosphorylation following treatment of a murine lymphocyte cell lysate with ATP or one of the ATP analogs (A*TPs).

Figure 4:
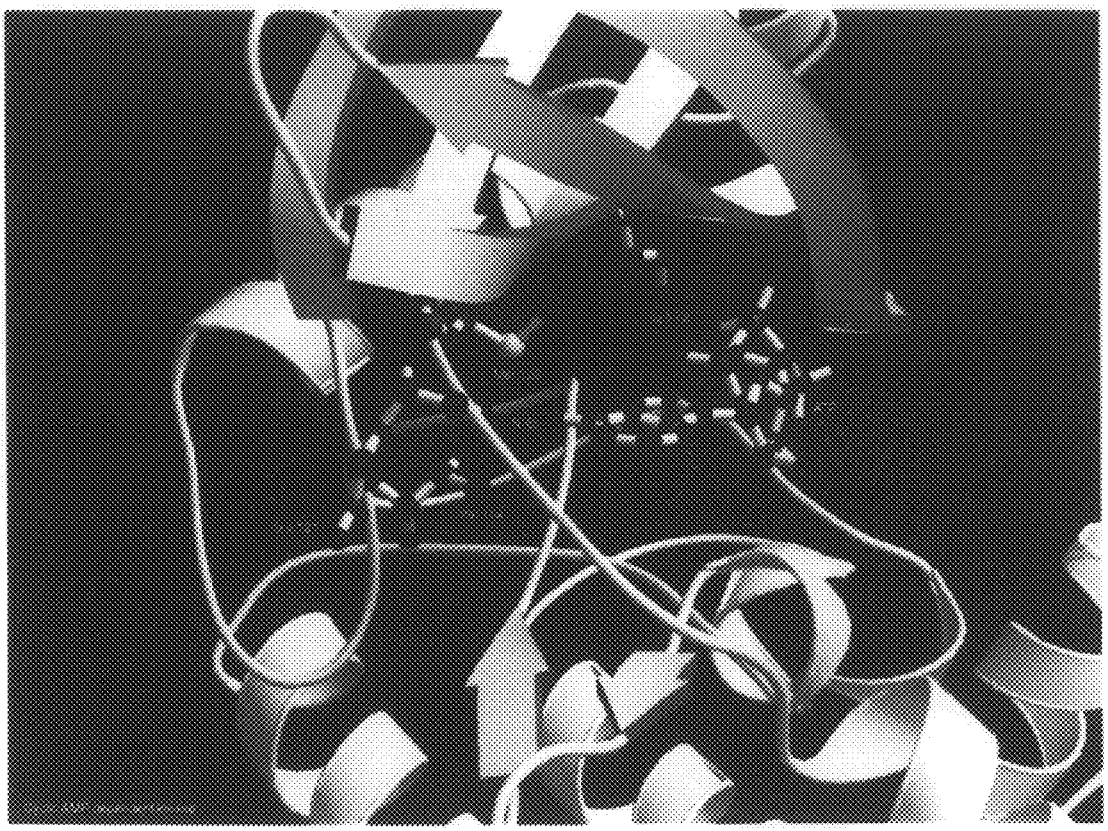

FIG. 4 provides a close-up view of the X-ray model showing the ATP binding domain in cAMP dependent protein kinase (1ATP).

FIGS. 5A–C: FIG. 5A shows an anti-phosphotyrosine blot of cell lysates expressing XD4 and GST-XD4(V323A, I338A). FIG. 5B shows an autoradiogram showing levels of phosphorylation when cell lysates are provided only radio-labeled ATP or only radiolabeled $N^6$ (cyclopentyl) ATP. FIG. 5C shows an autoradiogram showing autophosphorylation of GST-XD4 and GST-XD4(V323A, I338A) by radiolabeled ATP and radiolabeled $N^6$(cyclopentyl)ATP(A*TP(8)).

Figure 6:
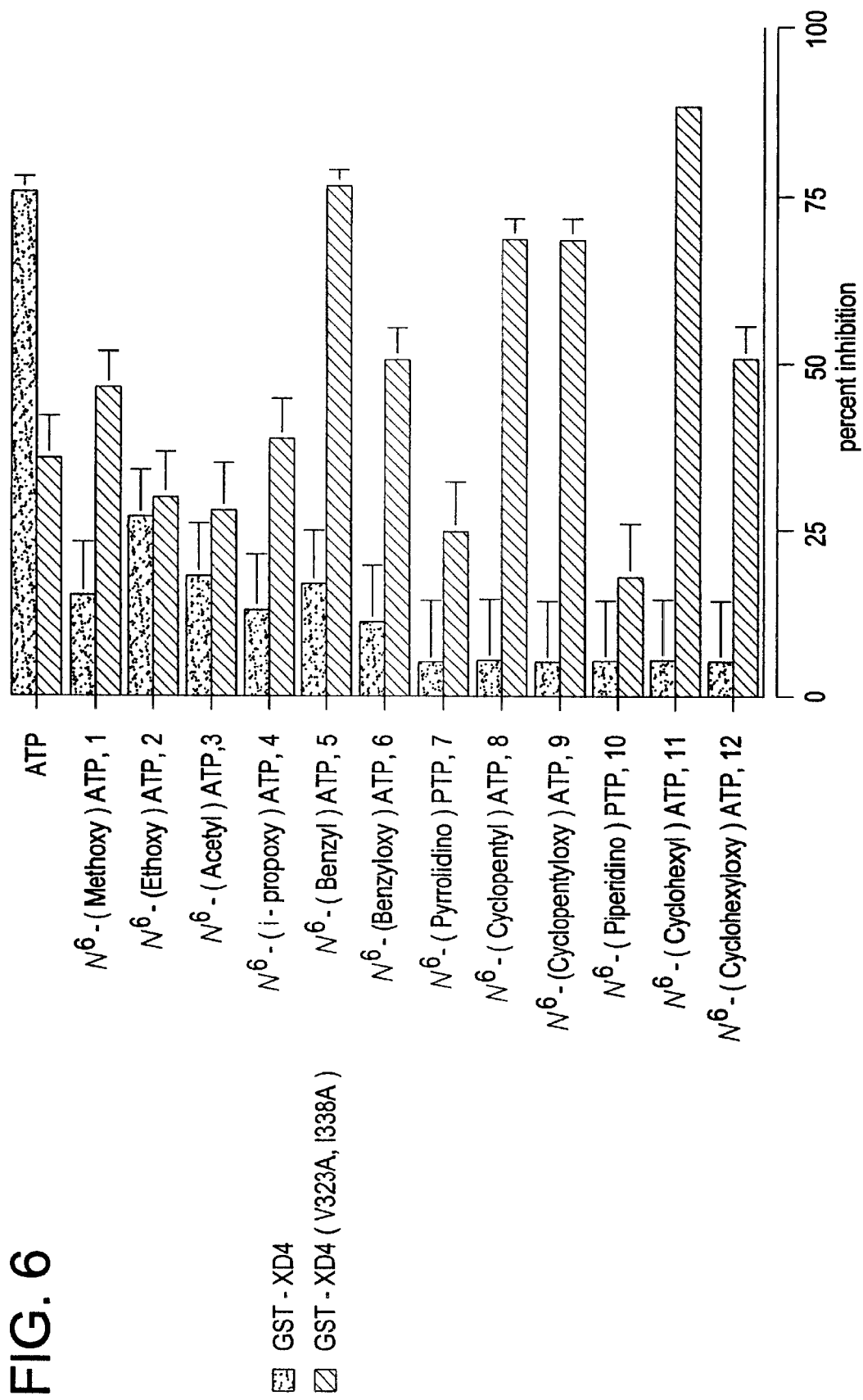
Figure 7A:
Figure 7B:
Figure 7C:
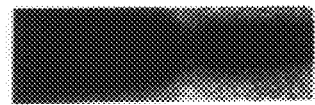
Figure 7D:

FIG. 6 is a bar chart showing the relative degree to which ATP and each of the twelve ATP analogs inhibits GST-XD4 and GST-XD4(V323A, I338A) catalyzed phosphorylation by radiolabeled ATP.

FIG. 7 shows autoradiograms indicating the levels of autophosphorylation by several v-Src position 338 single mutants when provided with either radiolabeled ATP and radiolabeled $N^6$ (cyclopentyl)ATP as phosphate donor substrate.

Figure 8:
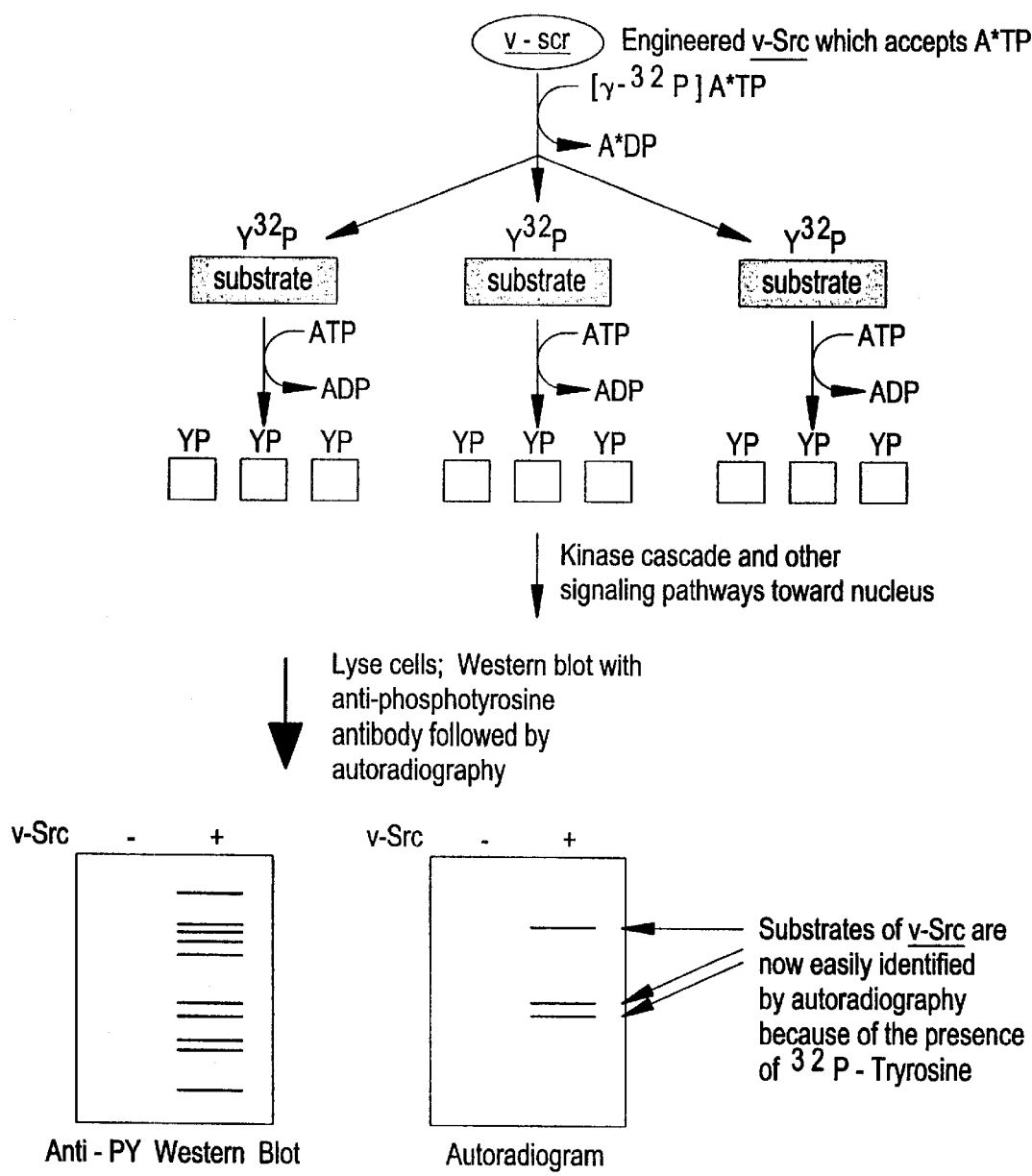

FIG. 8 is a schematic diagram of a method of the present invention for determining which phosphorylated substrates in cells were phosphorylated by a particular kinase. Here v-src.

Figure 9A:
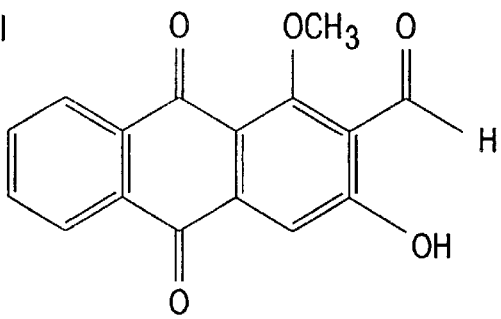
Figure 9B:
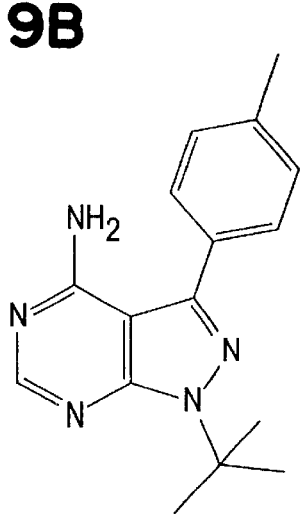
Figure 9C:
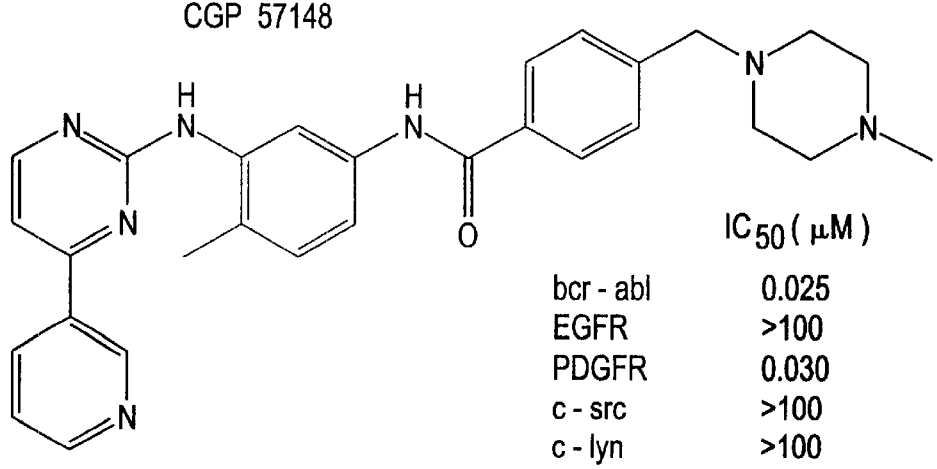

FIGS. 9A–C show the chemical structures for three known kinase inhibitors, Damnacanthal (A), PP1 (3) and CGP 57148 (C), along with summaries of their inhibition constants ($IC_{50}$) for several kinases.

FIGS. 10A–C: FIGS. 10A and 10B show the structures of a variety of bulky substituents which, when added to either N-4 of PP3 or to $N^6$ of adenosine diphosphate, or to $N^6$ of adenosine monophosphate, or to $N^6$ of adenosine (specifically $N^6$ cyclopentyloxy adenosine) to produce inhibitors of the mutant kinase v-Src(T120G), which is an engineered kinase of the present invention; the synthesis and inhibition constants (FIG. 10C) for these inhibitors are discussed in Example 12 below.

FIGS. 11A–11B shows the chemical structure of N-4 cyclopentoyl PP3, and autogradiograms of electrophoresed proteins which have become radiolabeled in the presence of N-4 cyclopentoyl PP3 in the presence of either wild-type v-Src or the mutant (I338G).

FIGS. 12A–F: FIGS. 12A–F disclose a chart presenting additional inhibitor analogs prepared and tested in accordance with the present invention.

Figure 13B:
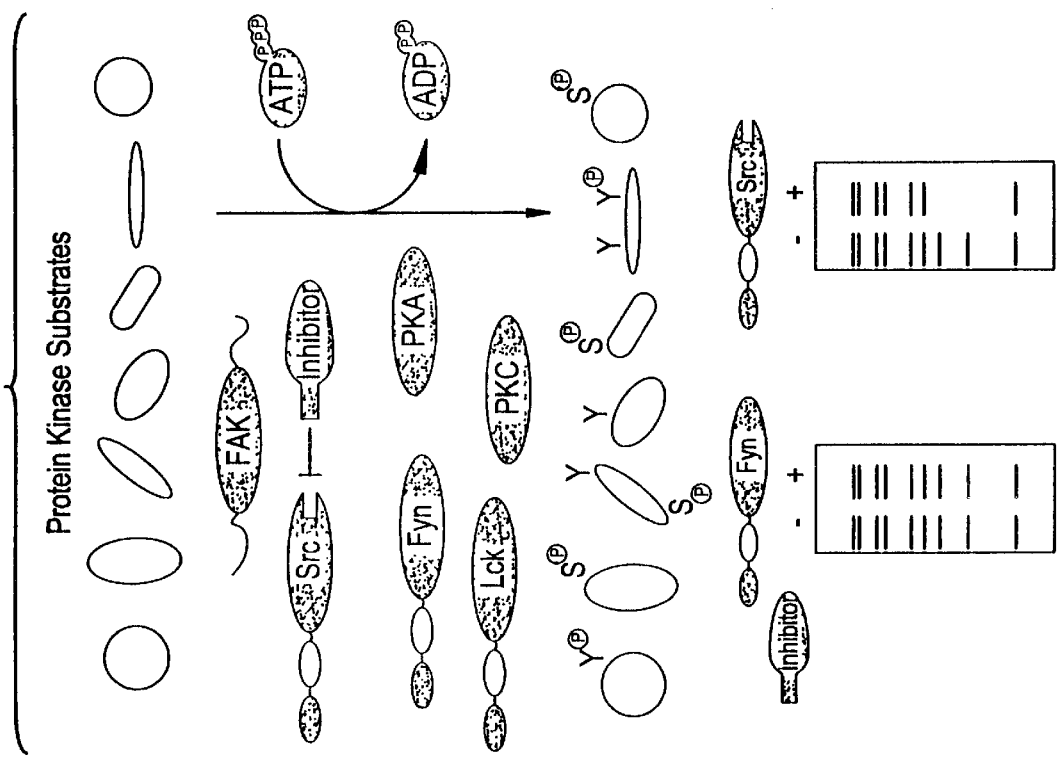
Figure 13A:
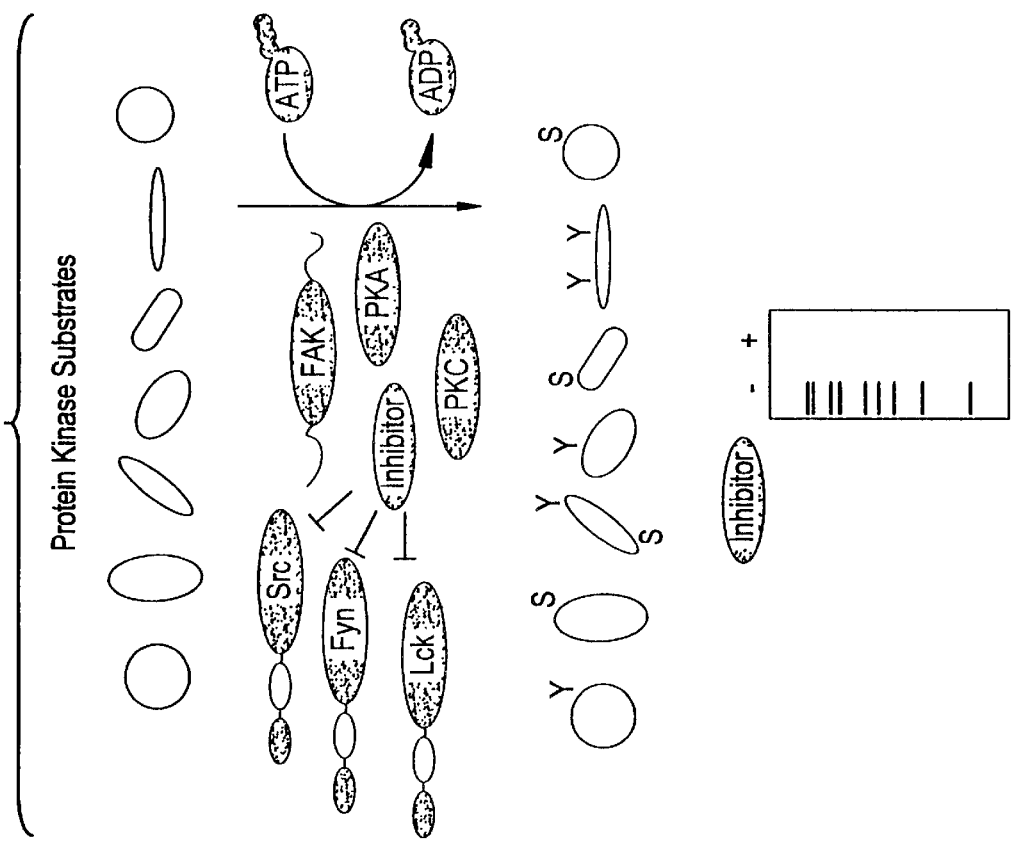

Names corresponding to FIGS. 12A–12F:
a. 1-tert-Butyl-3-phenyl-1H-indazol-4-ylamine
b. (1-tert-Butyl-3-phenyl-1H-indazol-4-yl)-ethyl-amine
c. (1-tert-Butyl-3-phenyl-1H-indazol-4-yl)-propyl-amine
d. (1-tert-Butyl-3-phenyl-1H-indazol-4-yl)-isobutyl-amine
e. (1-tert-Butyl-3-phenyl-1H-indazol-4-yl)-cyclopentylmethyl-amine
f. (1-tert-Butyl-3-phenyl-1H-indazol-4-yl)-furan-2-ylmethyl-amine
g. Benzyl-(1-tert-butyl-3-phenyl-1H-indazol-4-yl)-amine
h. N-(1-tert-Butyl-3-phenyl-1H-indazol-4-yl)-acetamide
i. N-(1-tert-Butyl-3-phenyl-1H-indazol-4-yl)-propionamide
j. N-(1-tert-Butyl-3-phenyl-1H-indazol-4-yl)-isobutyramide
k. N-(1-tert-Butyl-3-phenyl-1H-indazol-4-yl)-2-phenyl-acetamide
l. Cyclobutanecarboxylic acid (1-tert-butyl-3-phenyl-1H-indazol-4-yl)-amide
m. Cyclopentanecarboxylic acid (1-tert-butyl-3-phenyl-1H-indazol-4-yl)-amide
n. Cyclohexanecarboxylic acid (1-tert-butyl-3-phenyl-1H-indazol-4-yl)-amide
o. Furan-2-carboxylic acid (1-tert-butyl-3-phenyl-1H-indazol-4-yl)-amide
p. N-(1-tert-Butyl-3-phenyl-1H-indazol-4-yl)-benzamide
q. N-(1-tert-Butyl-3-phenyl-1H-indazol-4-yl)-4-methyl-benzamide
r. N-(1-tert-Butyl-3-phenyl-1H-indazol-4-yl)-4-ethyl-benzamide
s. N-(1-tert-Butyl-3-phenyl-1H-indazol-4-yl)-4-isopropyl-benzamide
t N-(1-tert-Butyl-3-phenyl-1H-indazol-4-yl)-4-propyl-benzamide
u. 4-tert-Butyl-N-(1-tert-butyl-3-phenyl-1H-indazol-4-yl)-benzamide
v. Biphenyl-4-carboxylic acid (1-tert-butyl-3-phenyl-1H-indazol-4-yl)-amide
w. N-(1-tert-Butyl-3-phenyl-1H-indazol-4-yl)-4-chloro-benzamide
x. N-(1-tert-Butyl-3-phenyl-1H-indazol-4yl)-3,4-dichloro-benzamide
y. 1-tert-Butyl-3-p-tolyl-1H-indazol-4-ylamine
z. (1-tert-Butyl-3-p-tolyl-1H-indazol-4-yl)-cyclopentylmethyl-amine
aa. N-(1-tert-Butyl-3-p-tolyl-1H-indazol-4-yl)-acetamide
bb. N-(1-tert-Butyl-3-phenyl-1H-indazol-4-yl)-2,2-dimethyl-propionamide
cc. 1-Methyl-3-phenyl-1H-indazol-4-ylamine
dd. sec-Butyl-(1-methyl-3-phenyl-1H-indazol-4-yl)-amine
ee. (1-Ethyl-propyl)-(1-methyl-3-phenyl-1H-indazol-4-yl)-amine
ff. (2-Methyl-butyl)-(1-methyl-3-phenyl-1H-indazol-4-yl)-amine
gg. (3-Methyl-butyl)-(1-methyl-3-phenyl-1H-indazol-4-yl)-amine
hh. Cyclopentyl-(1-methyl-3-phenyl-1H-indazol-4-yl)-amine
ii. Cyclohexyl-(1-methyl-3-phenyl-1H-indazol-4-yl)-amine
jj. (1-Methyl-3-phenyl-1H-indazol-4-yl)-phenyl-amine
kk. (3-chloro-phenyl)-(1-methyl-3-phenyl-1H-indazol-4-yl)-amine
ll. Benzyl-(1-methyl-3-phenyl-1H-indazol-4-yl)-amine
mm. 4-Chloro-1,3-diphenyl-1H-indazole
mn. 1,3-Diphenyl-1H-indazol-4-ylamine
oo. (1,3-Diphenyl-1H-indazol-4-yl)-propyl-amine
pp. sec-Butyl-(1,3-diphenyl-1H-indazol-4-yl)-amine
qq. (1,3-Diphenyl-1H-indazol-4-yl)-(1-ethyl-propyl)-amine
rr. (1,3-Diphenyl-1H-indazol-4-yl)-(2-methyl-butyl)-amine
ss. (1,3-Dimethyl-butyl)-(1,3-diphenyl-1H-indazol-4-yl)-amine
tt. (3,3-Dimethyl-butyl)-(1,3-diphenyl-1H-indazol-4-yl)-amine
uu. (1,3-Diphenyl-1H-indazol-4-yl)-diethyl-amine
vv. Cyclopentyl-(1,3-diphenyl-1H-indazol-4-yl)-amine
ww. Cyclohexyl-(1,3-diphenyl-1H-indazol-4-yl)-amine
xx. (1,3-Diphenyl-1H-indazol-4-yl)-phenyl-amine
yy. 1-Benzyl-4-chloro-3-phenyl-1H-indazole
zz. 1-Benzyl-3-phenyl-1H-indazol-4-ylamine
aaa. (1-Benzyl-3-phenyl-1H-indazol-4-yl)-(1-ethyl-propyl)-amine
bbb. (1-Benzyl-3-phenyl-1H-indazol-4-yl)-(1,3-dimethyl-butyl)-amine
ccc. (1-Benzyl-3-phenyl-1H-indazol-4-yl)-diethyl-amine
ddd. (1-Benzyl-3-phenyl-1H-indazol-4-yl)-cyclopentyl-amine
eee. (1-Benzyl-3-phenyl-1H-indazol-4-yl)-cyclohexyl-amine fff. (1-Benzyl-3-phenyl-1H-indazol-4-yl)-phenyl-amine FIGS. 13A–13B: FIG. 13A sets forth a schematic representation of the specificity problems associated with using small molecule protein kinase inhibitors to deconvolute cell signaling. Kinase catalytic domains are highly conserved. Thus, the majority of potent inhibitors block the activity of closely related kinases and broadly down regulate pathways mediated by kinase activity. FIG. 13B sets forth a schematic representation of the approach toward selective protein kinase inhibition described here. A space creating mutation is introduced into the ATP binding site of the kinase of choice (Src). This mutation creates an active site pocket (notch) in Src which can be uniquely recognized by a rationally designed small molecule inhibitor. This inhibitor contains a bulky chemical group (bump) which makes it orthogonal to wild type protein kinases. Design of the complementary kinase/inhibitor pair allows for highly selective inhibition of the target kinase in the context of whole cell.

Figure 14A:
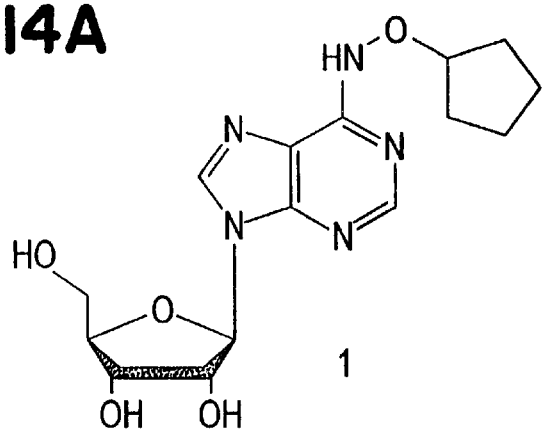
Figure 14B:
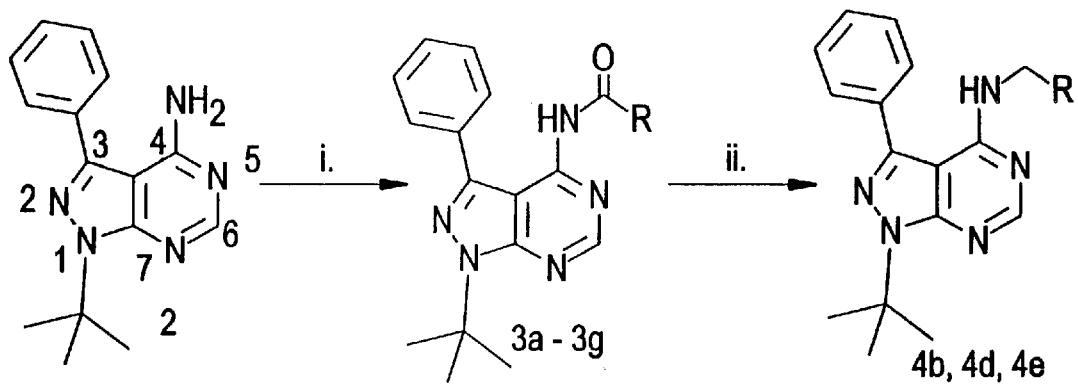

FIGS. 14A–B: FIG. 14A sets forth a structure of N-6 cyclopentyloxyadenosine (1). FIG. 14B sets forth the synthesis of pyrazolo[3,4-d] pyrimidine inhibitor and analogues. 2 was synthesized according to Hanefeld, et al. (i) RCOCI (10 equiv.), pyridine, 5(C, 1 h; then warm to 22(c, 11 h; (ii) LiAlH$_4$ (3.0 equiv), dry THF under argon, 0(C, 30 min; then heat to reflux for 30 min. All compounds were characterized by $^1$H NMR (300 MHz) and high resolution mass spectrometry (EI).

Figure 15A:
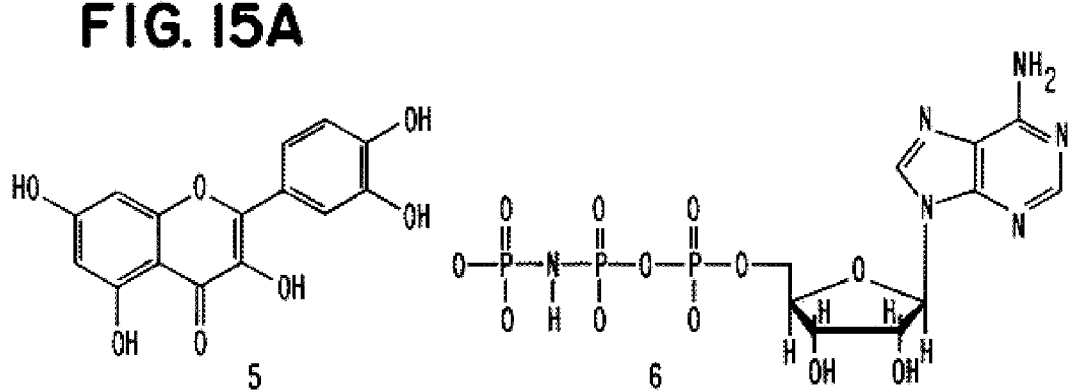
Figure 15B:
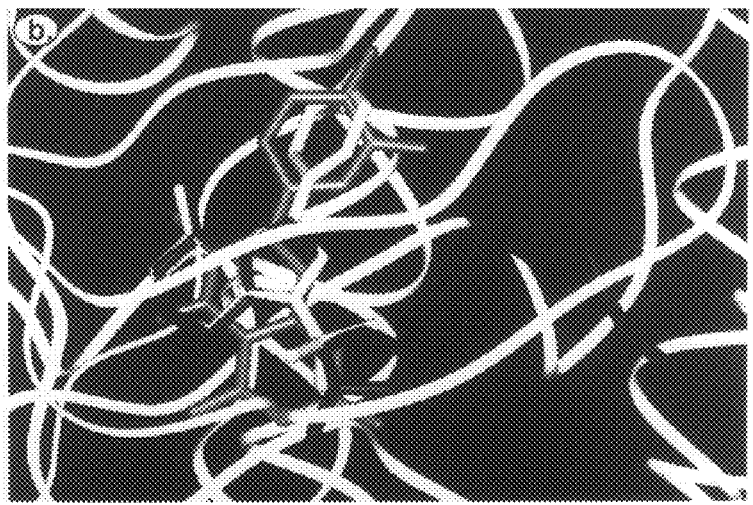
Figure 15C:
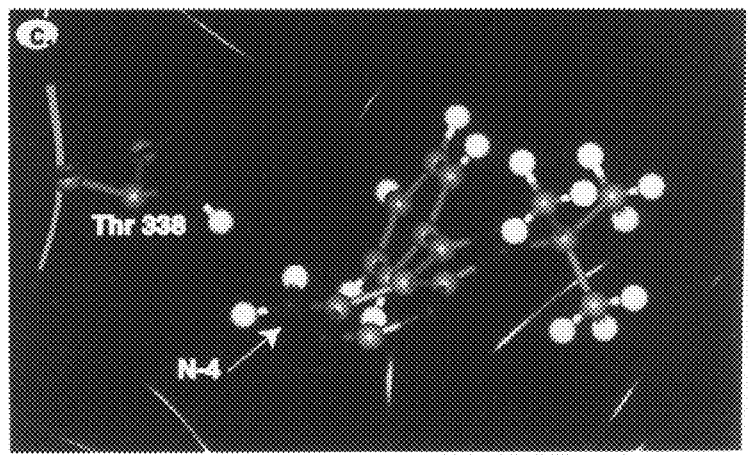

FIGS. 15A–15C: FIG. 15A sets forth the chemical structures of quercetin (5) and AMP PNP (6). FIG. 15B shows the predicted binding orientation of 2 in src family kinase active sites. The crystal structures of Hck bound to AMP PNP and Hck bound to quercetin were superimposed according to the HcK protein backbone. The structure of 2 was subsequently docked into the kinase active site by superimposing the pyrazolo[3,4-d]pyrimidine ring system of 2 onto the adenine ring of AMP PNP. FIG. 15C shows the predicted close contact between N-4 of 2 and the side chain of residue 338 in src family kinases. Molecule 2 has been docked into the ATP binding site of the src family kinase, Hck, as in FIG. 3. The methyl hydrogens of the threonine side chain are now shown. Images were generated using the program InsightII.

Figure 16:
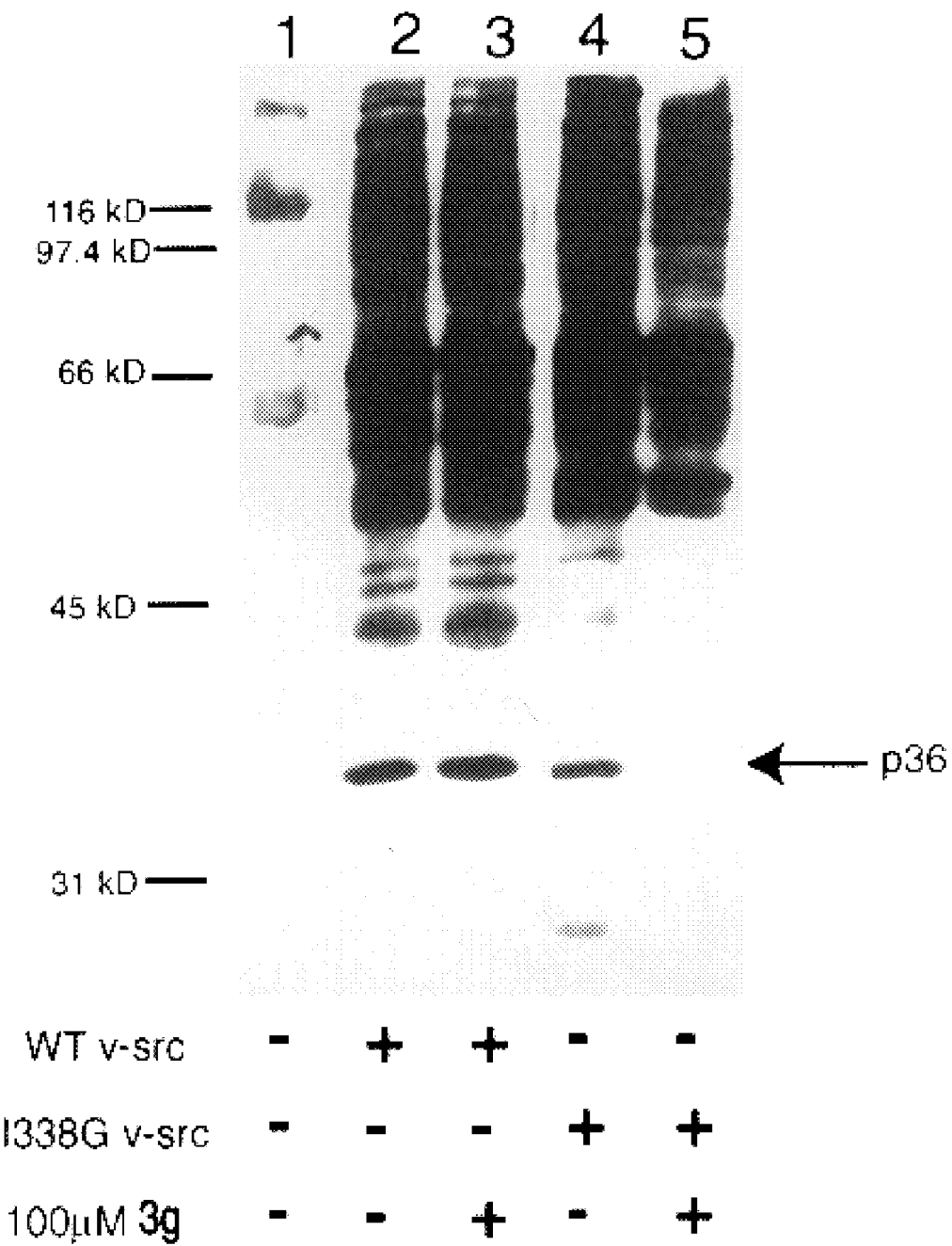
Figure 17A:
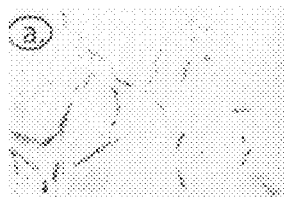
Figure 17B:
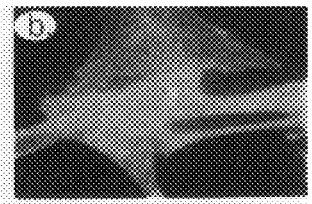

FIG. 16 shows the inhibitor 3 g (FIG. 14) blocks p36 phosphorylation in I338 G v-Src, but not WT v-Src transformed NIH3T3 fibroblasts. Non-transformed NIH3T3 cells (lane 1). WT v-Src transformed NIH3T3 cells (lanes 2–3), and I338G v-Src transformed NIH3T3 cells (lanes 4–5) were incubated with 1.1% DMSO (lanes 1, 2 and 4) or 100 μM 3 g in 1.1% DMSO (lanes 3 and 5). After 12 hours, the cells were lysed. Phosphorylation levels were determined as in FIG. 4.

FIGS. 17A–J show the I338G v-Src transformed fibroblasts selectively acquire a flattened morphology and selectively regain Actin stress fibers upon incubation with 3 g (FIG. 14). Non-transformed (a., b.), WT v-Src transformed (c., d., g., h.), and I338G v-Src transformed (e., f., i., j.). NIH3T3 fibroblasts were treated with either 1.1% DMSO (a., c., e., g., i.) or 100 μM analog 3 g in 1% DMSO (d., f., h., j.). After 48 hours cells were photographed (a., c.,f.), stained with phalloidin-FITC, and visualized (b., g., j.) by fluorescence microscopy.

Figure 18:
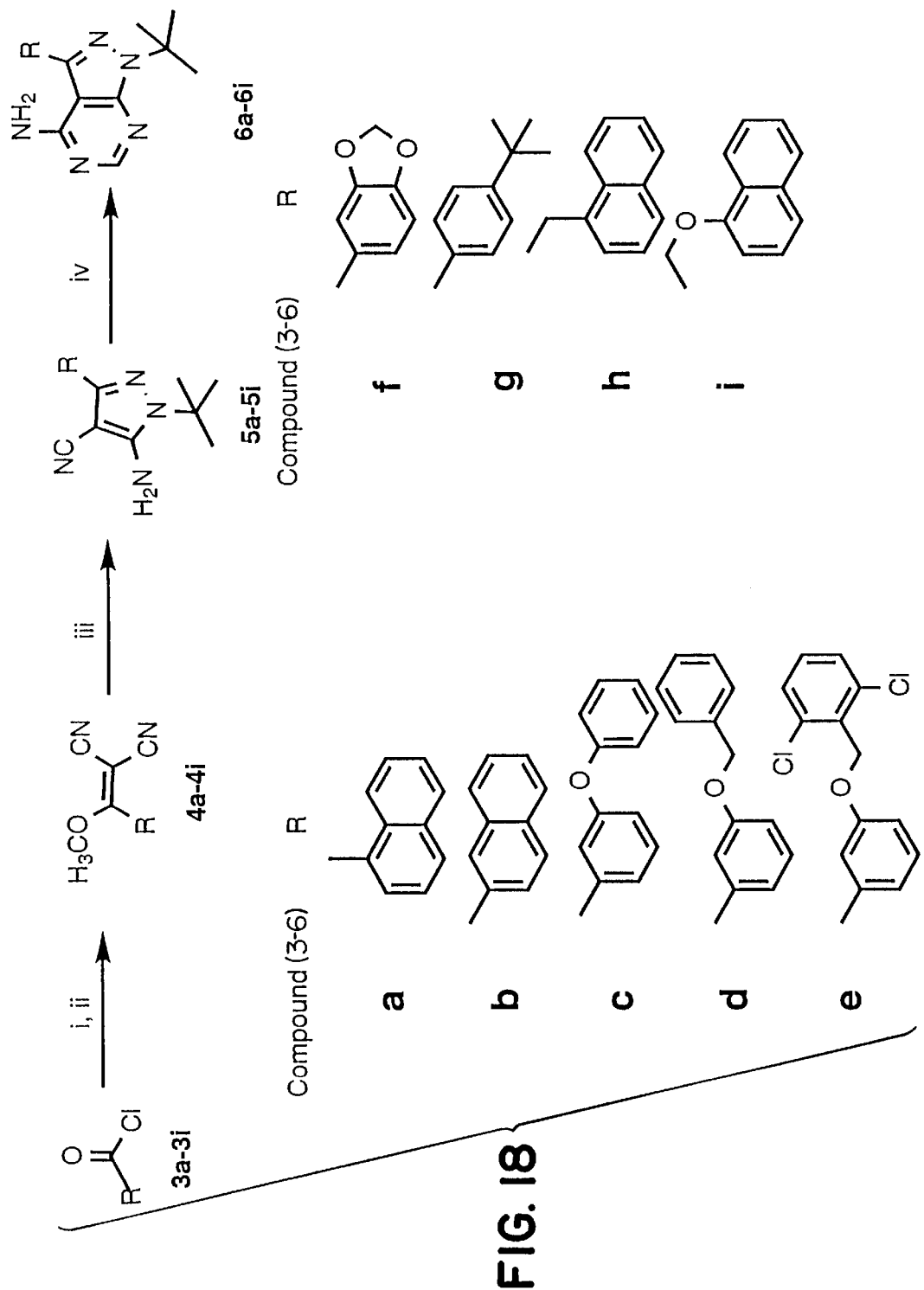

FIG. 18 sets forth the synthesis of C$^3$ Derivatized PP1 Analogues. Conditions: (i.) 2 equiv NaH, 1 equiv malonitrile, THF, RT, 0.5 h; (ii.) 5 equiv NaHcO$_3$, 5 equiv dimethyl sulfate, dioxane/H$_2$O(6/1), 80° C., 1 h; (iii.) 1 equiv triethylamine, 1 equiv tert-butylhydrazine hydrochloride, EtOH, reflux, 1 h; (iv.) formamide, 180° C., 12 h.

Figure 19:
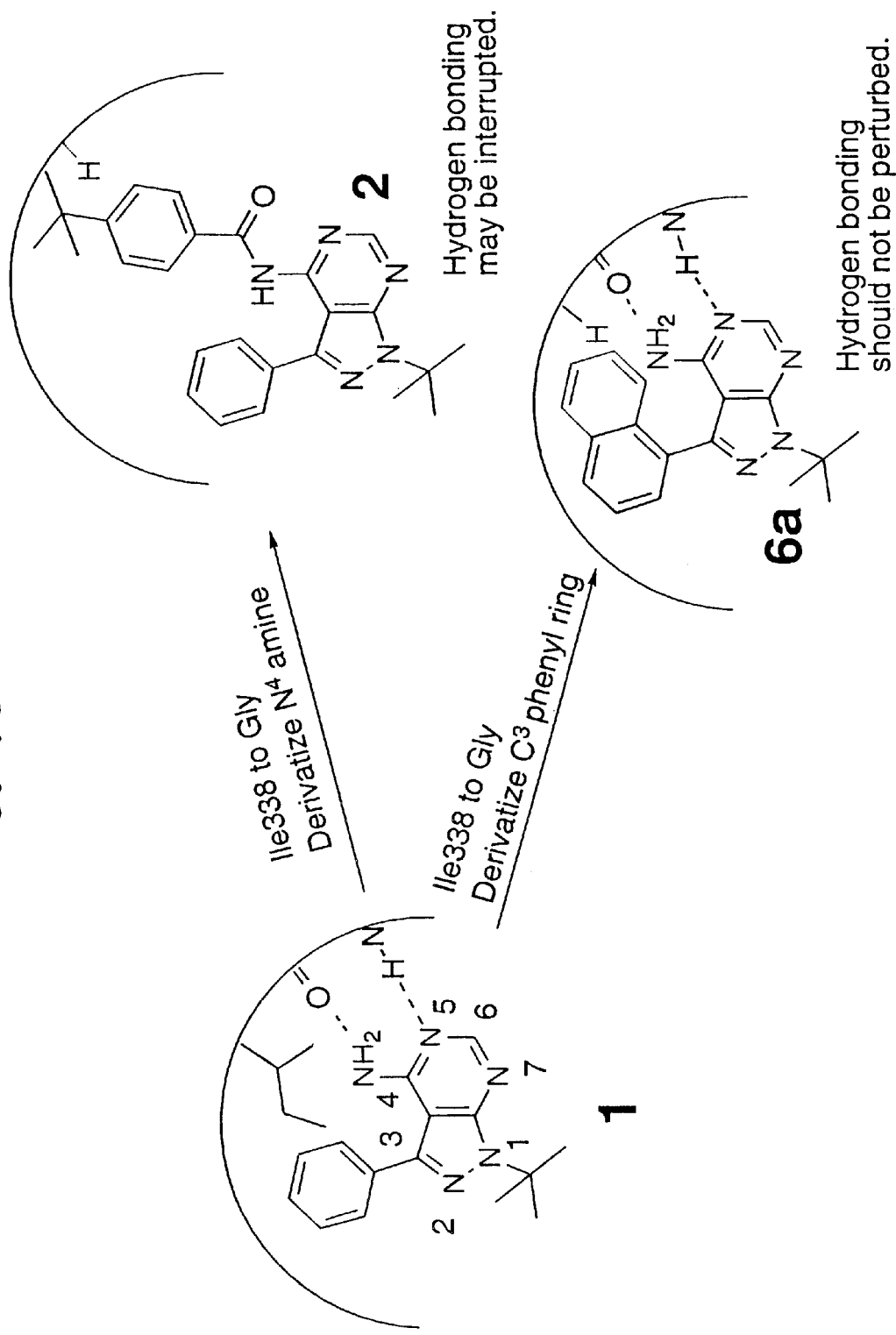

FIG. 19 sets forth a schematic representation of the predicted binding orientation of two classes of derivatized pyrazolo[3,4-d]pyrimidines. Analogues that were derivatized at N$^4$ may have lost potency due to an interruption of the ATP-like hydrogen bonding network. This network is presumably intact in the C$^3$ derivatized inhibitors.

FIGS. 20A–20B: FIG. 20A shows the effect of 6a (FIG. 18) on tyrosine phosphorylation in NIH3T3 fibroblasts expressing either wild type v-Src (lanes 1, 2) or I338G v-Src (lanes 3–8). Cells were treated with the indicated amount of 6a (FIG. 18) in 0.5% DMSO for 30 min and immediately lysed. Cellular proteins were separated by polyacrylamide gel electrophoresis (10%) and transferred to nitrocellulose. Tyrosine phosphorylated proteins were visualized by immunoblotting with a monoclonal anti-phosphotyrosine antibody (4G10). FIG. 20B shows the effect of 6a (FIG. 18) on tyrosine phosphorylation in wild type Jurkat cells. 10$^6$ Jurkat cells were incubated at 37° C. for 30 min in the presence of 0.5% DMSO (lanes 9,10), 500 nM 6a (lane 11), or 10 μM PPI (lane 12). Cells in lanes 10–12 were subsequently treated with 0.5 mM pervanadate for 10 min before lysis. Tyrosine phosphorylated proteins were visualized as in FIG. 20A.

Figures 21A, 21B:
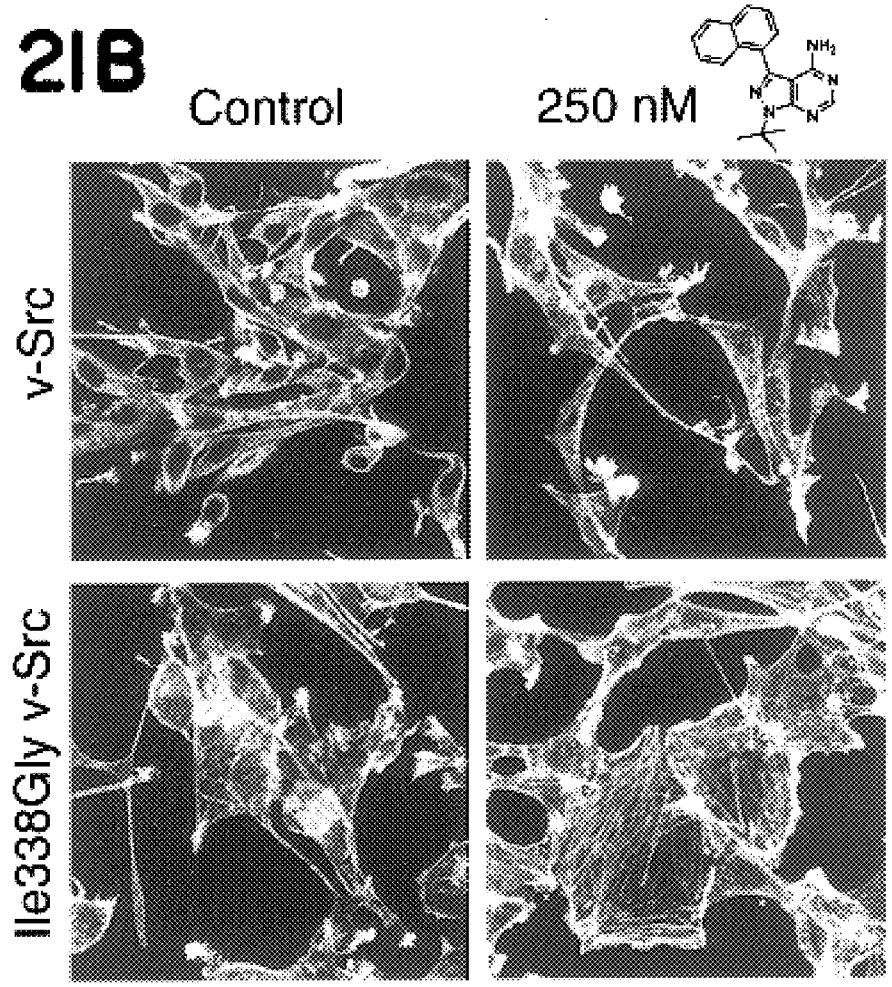

FIGS. 21A–21B: FIGS. 21A and B show 338G v-Src transformed fibroblasts selectively acquire a flattened morphology and selectively regain actin stress upon incubation with 6a (FIG. 18). FIG. 21A show non-transformed NIH3T3 cells. FIG. 21B show cells transformed by either wild type v-Src or I338G v-Src were treated with 0.5% DMSO or 250 nM 6a in 0.5% DMSO for 16 hours. All cells were fixed, stained with phalloidin-rhodamine, and visualized by confocal microscopy.

Figure 22A:
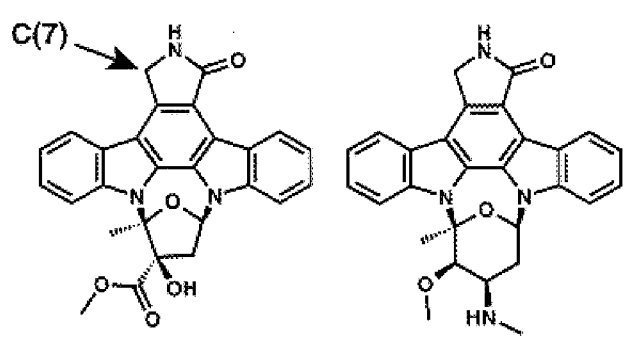
Figure 22B:
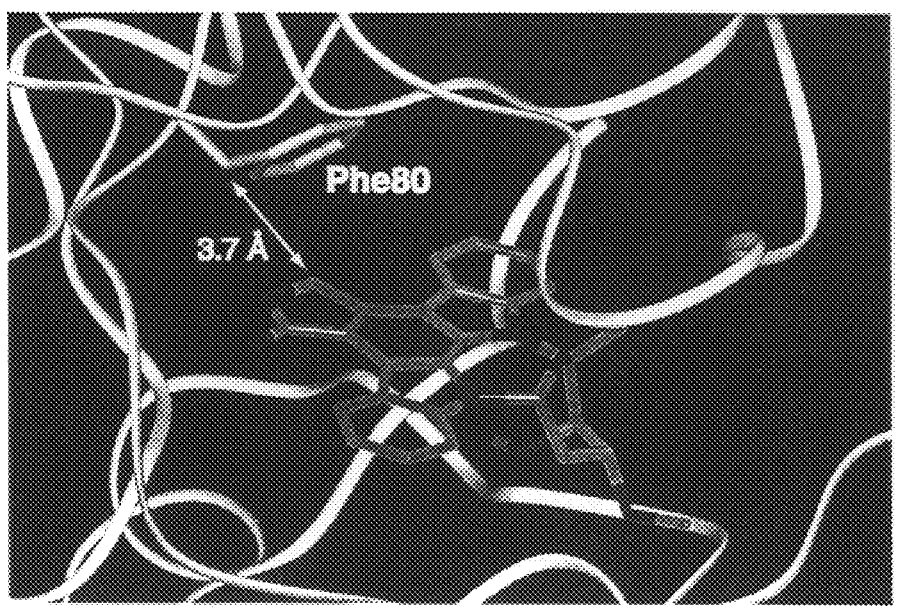

FIGS. 22A–22B: FIG. 22A shows chemical structures of (+)-K252a (1) and (+)-Staurosporine (2). FIG. 22B shows crystal structure of 2 bound to CDK2 (28). CDK2 is shown with the peptide backbone illustrated as a ribbon and the F80 side chain as sticks. Staurosporine is shown with carbon, nitrogen, and oxygen. Hydrogens are not shown.

Figure 23A:
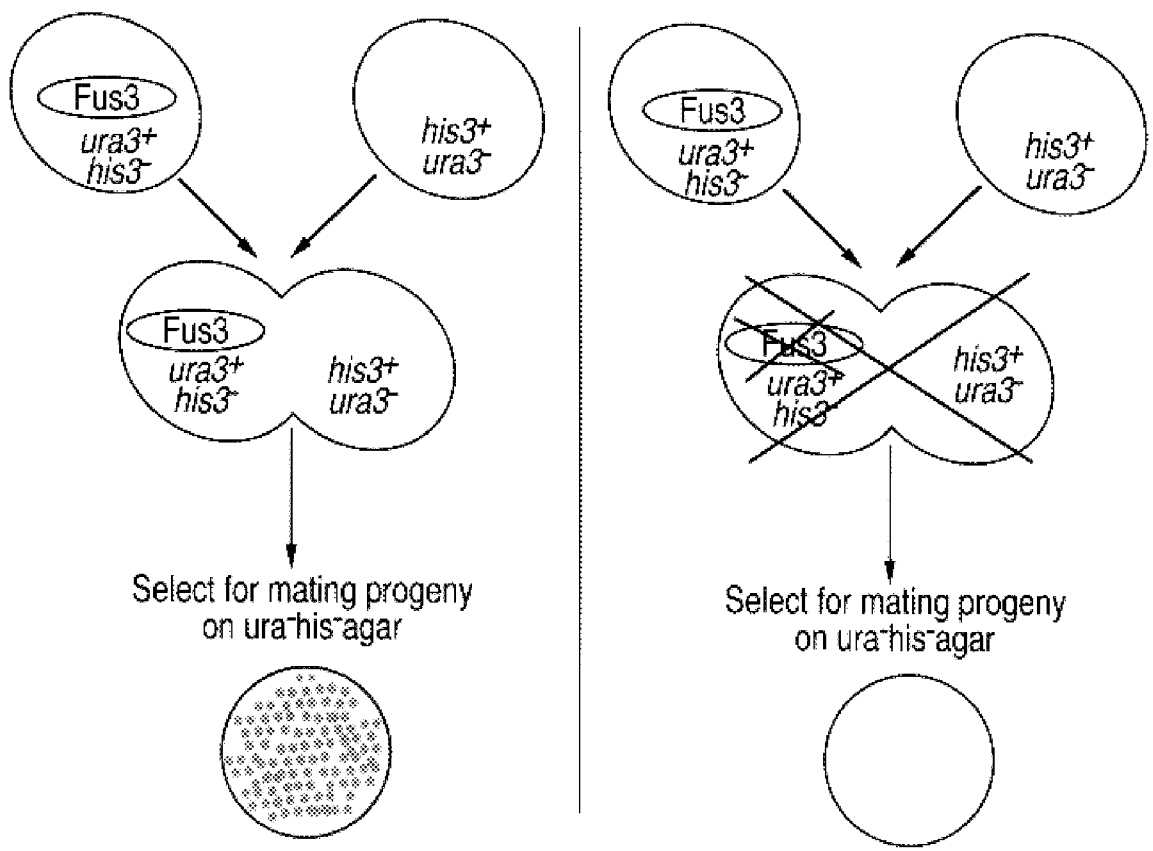
Figure 28:
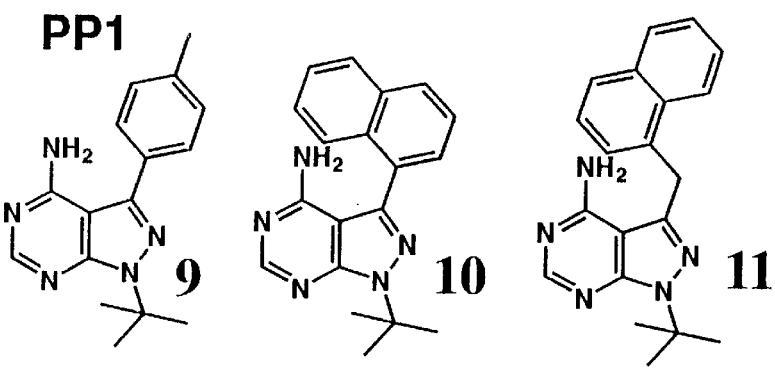

FIGS. 23A–C: FIG. 23A sets forth a schematic diagram of mating assay used to test for Fus3 function. FIGS. 23B and C show selective disruption of fus3-as1 yeast mating by 10 (FIG. 28) and 11 (FIG. 28). Haploid URA3 his3 S. cerevisiae expressing either wild-type Fus3, Fus3-as1, or no Fus3 at OD$_{600}$=0.5 were mated with an equal number of ura3 HIS3fus1Δfus2A cells and pipetted onto a nitrocellulose disk. The disk was placed on a YPD plate containing the indicated amounts of inhibitor for 5 hours at 30° C. Cells were liberated from the disks and serial dilutions of the resulting cultures were plated on media lacking uracil and histidine and grown for two days at 30° C. and the colonies were counted. To ensure that 10 and 11 (FIG. 28) were not non-selectively cytotoxic, all cultures were also plated on YPD. No significant decrease in cfu/mL on YPD plates was observed for any of the three strains in the presence of 10 or 11 (FIG. 28). FIG. 23B sets forth Photograph of plates lacking histidine and uracil which were inoculated with 0.1 mL of the mating cultures from the following strains (from top): fus3Δ, fus3, fus3+5 μM 10, fus3-as1, fus3-as1+5 μM 10. FIG. 23C shows disruption of Fus3 dependent mating is selective and dose dependent. The bars indicate the cfu/mL× 10$^{-3}$ for wild-type Fus3 or for Fus3-as1 expressing yeast at the indicated inhibitor concentrations. Experimental conditions are as described above.

Figure 24:
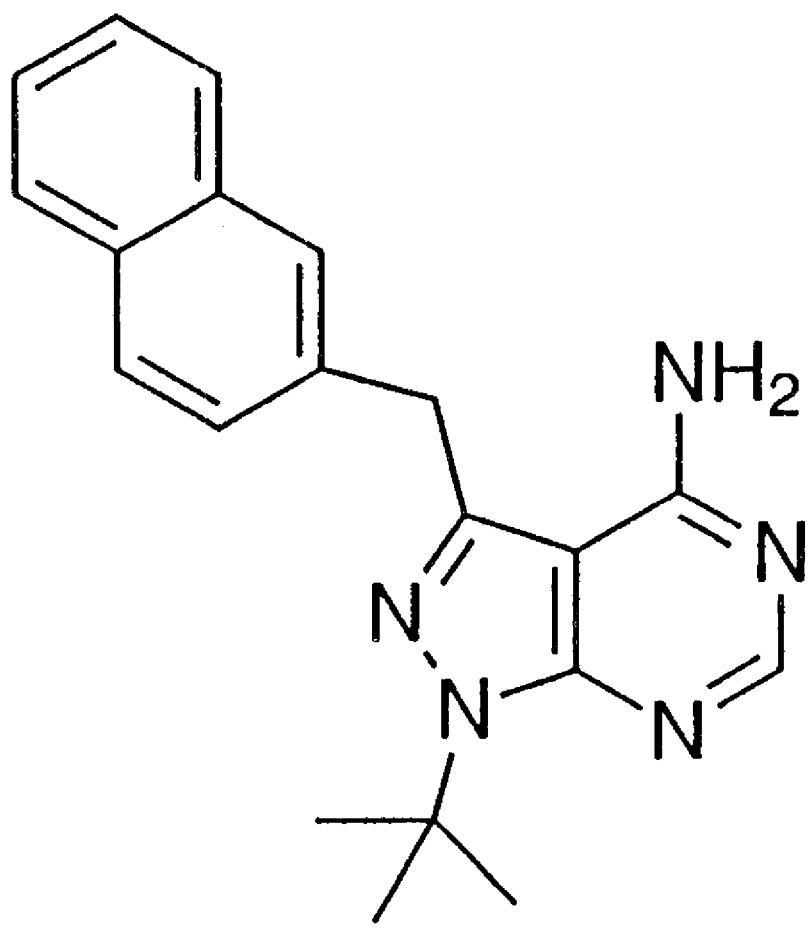

FIG. 24 shows the structure of 4-amino-1-(tert-butyl)-3-(2'-napthylmethyl)pyrazolo[3,4-d]pyrimidine (6j).

Figure 25C:
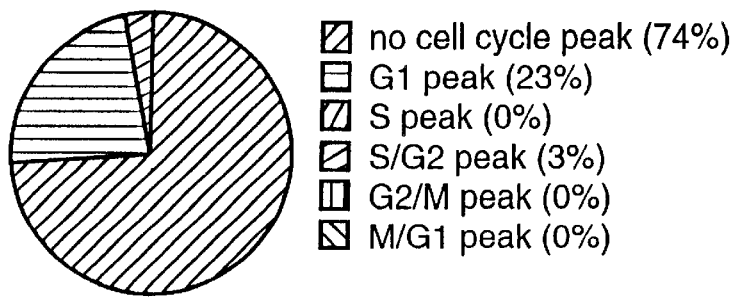
Figure 25D:
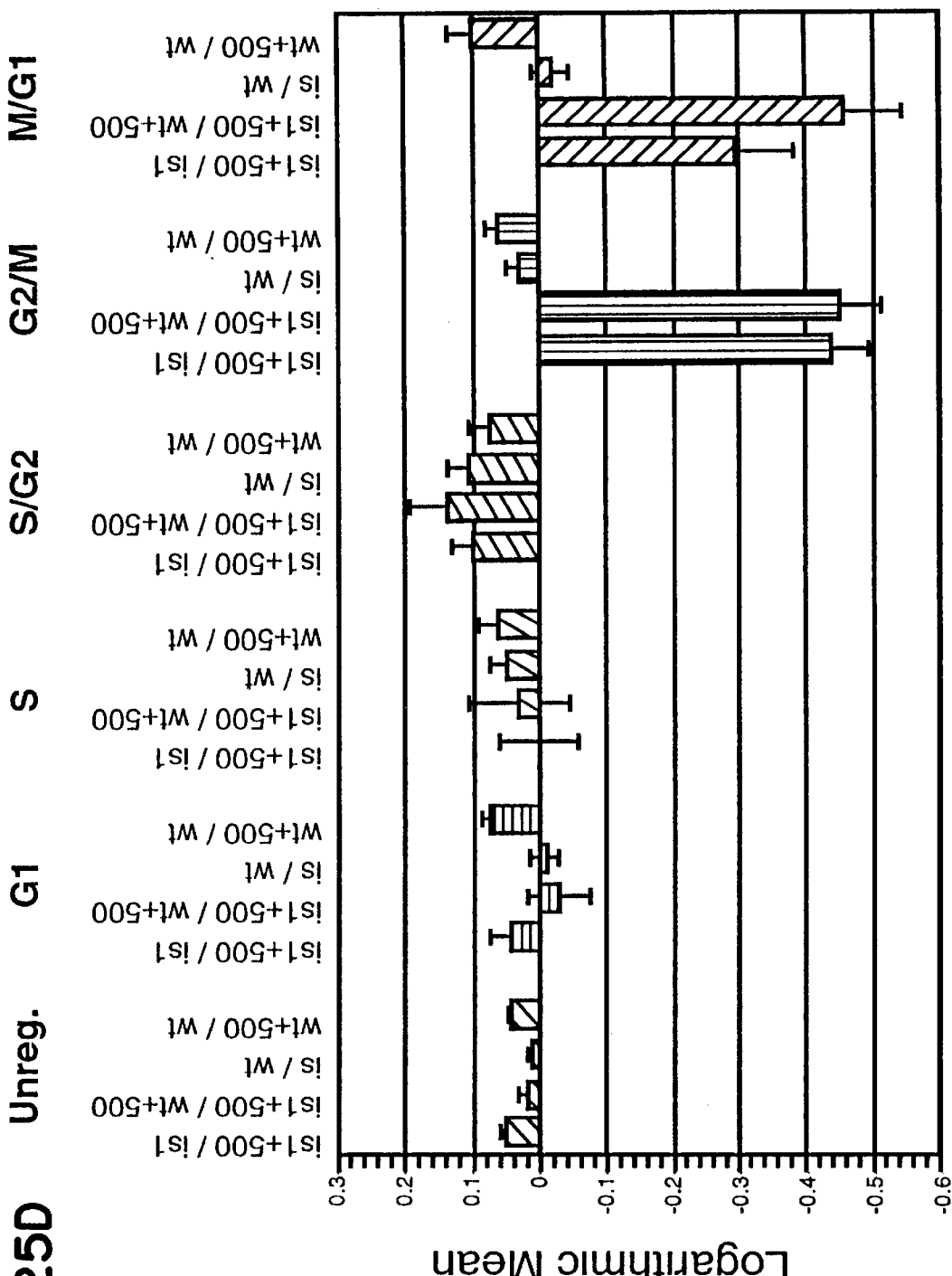

FIGS. 25A–D set forth 500 nM 1-NM-PP1 addition causes a drop in G2/M transcription. FIGS. 25A–C show an asynchronous population of cdc28-as1 cells was treated with 1-NM-PP1 for 120 minutes. Genome-wide transcriptional differences in the absence and presence of inhibitor were measured by oligonucleotide microarray analysis of cellular mRNA (127). For comparison, FIG. 25A shows the percentage of genes whose transcription is known to be regulated during the cell cycle (150). FIG. 25B shows transcripts that decreased over 2.5-fold following inhibitor treatment. FIG. 25C shows transcripts that increase after inhibitor treatment. Transcripts are grouped in the lists and pie charts according to their known cell cycle regulation (150). FIG. 25D shows genome-wide changes in gene expression were assessed in four comparisons as follows: 1. cdc28-as1 cells+500 nM 1-NM-PP1 compared to untreated cdc28-as1 cells (as1+500/as1); 2. drug-treated cdc28-as1 cells compared to drug-treated wild-type cells (as1+500/wt+500); 3. untreated cdc28-as1 cells compared to wild-type cells (as1/wt); and 4. drug-treated wild-type cells compared to untreated wild-type cells (wt+500/wt). For each comparison, the ratio of gene expression under the two conditions was converted to its natural logarithm. The mean logarithmic change in expression of all genes in each of the major cell cycle clusters (G1, S, S/G2, G2/M, M/G1), as well as that of genes whose expression is not cell-cycle-regulated (Unreg.), was calculated. Error bars represent standard errors of the means.

FIGS. 26A and 26B: (a.) Classification, substrate specificities, and cellular functions of the protein kinases utilized in this report. (b.) Sequence alignment of the residues surrounding position 338 (v-Src numbering) for the protein kinases listed in (a) (SEQ ID NO: 14–20).

FIG. 27: 50% inhibitory concentrations (IC$_{50}$, $\mu$M) for K252a and C(7) derivatized K252a analogs against a panel of wild-type and rationally engineered protein kinases. IC$_{50}$ values for the best K252a derivative/engineered kinase pair are shown. Kinase purification and measurement of IC$_{50}$ values were performed essentially as described (86).

FIG. 28: 50% inhibitory concentrations (IC$_{50}$, $\mu$M) for PP1 and C(3)-phenyl derivatized PP1 analogs against a panel of wild-type and rationally engineered protein kinases. IC$_{50}$ values for the best PP1 derivative/engineered kinase pair are shown. Kinase purification and measurement of IC$_{50}$ values were performed essentially as described (86).

DETAILED DESCRIPTION OF THE INVENTION

I. Definitions

As is generally the case in biotechnology, the description of the present invention herein has required the use of a substantial number of terms of art. Although it is not practical to do so exhaustively, definitions for some of these terms are provided here for ease of reference. Definitions for other terms also appear elsewhere herein, and those are not repeated here. It is important to note that it is not intended that the terms defined here or elsewhere herein be given a meaning other than that which those skilled in the art would understand them to have when used in the field, and it is therefore urged that other sources also be consulted in interpreting the meaning of these terms and those defined elsewhere herein. However, the definitions provided here and elsewhere herein should always be considered in determining the scope and meaning of the defined terms.

As used herein, the term "enzyme" means any naturally occurring or synthetic macromolecular substance composed wholly or largely of protein, that catalyzes, more or less specifically, one or more (bio)chemical reactions. The substances upon which the enzymes act are known as "substrates", for which the enzyme possesses a specific binding or "active site". Enzymes can also act on macromolecular structures such as muscle fibers and more "cargo" such as intracellular vesicles. Such proteins are called motor proteins, two classes of which are myosins and kinesins.

As used herein, the term "catalytic activity of an enzyme" is defined as the property measured by the increase in the rate of conversion of a specified chemical reaction that the enzyme produces in an assay system.

As used herein, the term "kinase" means any phosphotransferase enzyme that transfers a phosphate group.

As used herein, the term "protein kinase" means any enzyme that phosphorylates one or more hydroxyl or phenolic groups in proteins, ATP being the phosphoryl-group donor.

As used herein, the term "phosphorylase" means any enzyme that catalyzes the phosphorolytic removal of the nonreducing terminal glucose residue from a glucan.

As used herein, the term "phosphorylase kinase" is synonymous with the term "protein phosphorylase kinase" and means any phosphorylase enzyme that converts phosphorylase b to phosphorylase a.

As used herein, the term "phosphorylase phosphatase" is synonymous with "protein phosphorylase phosphatase" and means any phosphorylase enzyme that converts phosphorylase a to phosphorylase b.

As used herein, the term "tyrosine kinase" is synonymous with the term "protein tyrosine kinase" and means an enzyme that transfers the terminal phosphate of ATP to a specific tyrosine residue on its target protein.

As used herein, the term "transferase" means any enzyme that catalyzes the transfer of a group—e.g., the methyl group, glycosyl group, acyl group, phosphorus-containing, or other groups.

As used herein, the term "methyltransferase" is synonymous with the term "transmethylase" and means any of the enzymes which catalyze the transfer of a methyl group.

The term "low affinity inhibitor" refers to a small molecule which has a binding constant (IC$_{50}$) for the target enzyme of greater than about 200 nM, and thus would need to be used at a high concentrations in a cell based or whole animal based assay (a concentration of greater than 50 $\mu$M). Such high concentrations might induce non-specific drug affects that could mask the specific role of the desired target of the inhibitor.

As used herein, the term "mutant specific inhibitor" is defined as an inhibitor that inhibits a specific type of mutant enzyme.

As used herein, the term "monospecific inhibitor" means an inhibitor that is only able to react with a single specified enzyme.

The term "high affinity inhibitor" refers to a small molecule which has a binding constant (IC$_{50}$) for the target enzyme of less than about 200 nM, and thus allowing it to be used at "low" concentrations in a cell based or whole animal based assay (a concentration less than 50 $\mu$M). At lower concentrations, the non-specific effects of the small molecule would be lessened, thus allowing a more true response to inhibition of the target kinase to be assessed.

The term "orthogonal" is used here to mean a compound that is similar, structurally and/or geometrically, to the natural substrate for a given enzyme, or to an inhibitor of the wild-type form of the enzyme, but has differences in chemical structure which make that compound less able to bind to the wild-type form of the enzyme than is the natural substrate. By "natural" substrate it is meant that the substrate which is utilized by the wild-type form of that enzyme. The orthogonal inhibitors of the present invention may be referred to in different ways herein; for example, sometimes they are referred to as "modified substrates," "modified inhibitors," "analogs," "derivatives," just as "substrates," or "inhibitors," and perhaps by other terms as well. However, in each instance, the same meaning is intended. Of course, the meaning of "orthogonal" and its synonyms are further explained in the descriptions of the invention provided below.

The putative orthogonal substrates and inhibitors of the embodiments of the invention described herein were made by adding bulky substituents to an atom on the natural substrate of known kinase inhibitor, respectively. However, the present invention is not so limited. For example, it is possible to make an orthogonal substrate that is smaller than a known inhibitor or the natural substrate, e.g., by preparing an analog that is missing one or more atoms or substituents that are present in the natural substrate. With such putative orthogonal substrates or inhibitors, one could mutate the enzyme to contain one or more amino acids having more bulky side chains than those found in the wild-type amino acid sequence, so that when the orthogonal substrate or inhibitor binds, those more bulky amino acid side chains fill or partially fill the extra space created by the missing atoms or substituents. In this way, it would be expected that the mutant would bind to and/or be inhibited by the orthogonal substrate or inhibitor but would not substantially utilize the normal substrate, because the added bulky amino acids present a steric hindrance to its binding. Such an approach would allow for highly selective control of the resulting mutant.

It is important to keep in mind that even though the substrates and inhibitors of the examples herein are of the non-competitive type, this should not be viewed as a limitation of the scope of the present invention. Many different types of enzyme substrates and inhibitors are known, e.g., competitive, non-competitive, uncompetitive, "suicide" inhibitors, etc. Competitive inhibitors compete with a substrate for its binding site, but since the inhibitor cannot participate in the catalytic reaction which that enzyme carries out, it slows down catalysis. Non-competitive inhibitors bind to the active site, but then become covalently or ionically bound to the protein structure of the enzyme, such that they cannot come off. Thus, they inhibit catalysis by taking molecules of enzyme out of the reaction altogether. More detailed descriptions of these and other competitive mechanisms can be found in a variety of sources (e.g., 72). By applying the understanding of the art regarding such mechanisms to the design of inhibitors of the present invention, all such types of inhibitors could be made.

For example, an analog which can bind, but not react, would provide a competitive inhibition, and an analog which becomes covalently attached to the enzyme upon binding, would be a non-competitive inhibitor, i.e.,, a poison. All such types of inhibitors are within the scope of the present invention.

The term "homologous to" has been used to describe how information about how to modify one enzyme can be deducted from information regarding the three-dimensional structure of other, related enzymes. As those in the field well know, a part of one enzyme which is "homologous" to part of a second enzyme has a protein sequence which is related to that of the second enzyme. This relationship is that they have a number of amino acids in the same relative location to one another. For example, the imaginary sequence Asp-Met-Phe-Arg-Asp-Lys-Glu (SEQ ID NO: 10) and the imaginary sequence Asp-Met-Ile-Arg-Glu-Lys-Asp (SEQ ID NO: 11) have four amino acids in the same relative location, and three which are different, and they would be said to have homologous sequences. Note that the three amino acids that are different between the chains are "conservative" differences, in that the substitutions in the second sequence relative to the first are with amino acids that have similar functionalities on their side chains. For example, Glu and Arg both have charged groups and both Phe and Ile are hydrophobic. Although this is often the case with homologous protein sequences, it need not be the case, and these two imaginary sequences would still be considered homologous even if the differences were not conservative. Reference 71 gives a good overview of which domains of the known kinases are considered by the art to be "homologous." In addition, although the art may not generally agree, it is intended here that sequences that are identical to one another also be considered to be "homologous" to one another.

The term "domain" is also one well known in the art, and it refers to a region in a protein which has been identified as having a particular functionality. For example, the three domains in protein kinases have been discussed elsewhere herein, and their functional roles have been discussed. Often, as is the case with the kinases, different enzymes of the same family will have the same number of domains with each serving the same function, and they are often (but probably not always) arranged in the same order along the protein sequence. Interestingly, as is the case for the kinases, one enzyme may have a different length of protein sequence between its domains than does another. However, since the domains of two related enzymes are generally (but probably not always) homologous to one another, this does not generally hamper the identification of corresponding domains.

In describing the broader aspects of the present invention, the terms "multi-substrate" or "multi-substrate enzyme" are used. These terms are synonymous and are intended to mean enzymes which bind two or more substrates. Those multi-substrate enzymes of most interest here are those which catalytically attach at least part of one substrate to at least one other substrate. The kinases and the transferases are but two families of such multi-substrate enzymes, and those of skill in the art will readily recognize that there are other such enzymes and enzyme families.

The term "recognize" is sometimes used here to describe the ability of a substrate to specifically bind to the active site on an enzyme. This simply refers to the fact that an enzyme's substrate (or sometimes substrate derivatives or even completely different compounds that mimic the substrate) can contact and bind to the enzyme's active site, but other compounds will not. This concept is well known in the art. Enzymologists often say that the enzyme has an affinity for its substrate, or that the substrate has an affinity for the enzyme. They also say that an enzyme has "substrate specificity," These all really describe the same phenomenon.

A related term is the term "bind." An inhibitor generally binds, or sticks to, to an active site through one or more hydrophobic, hydrophilic, hydrogen, and/or ionic bonds, or, in the case of non-competitive inhibitors, through covalent bonds. Although the complex understanding in the art regarding inhibitor binding and the reasons for inhibition may be of interest, such an understanding is not essential to understanding the present invention. It is sufficient to simply note that binding by an inhibitor causes inhibition of the catalytic reaction.

The terms "mutant" and "engineered form," when used to describe the enzymes of the present invention, simply mean that they have sequences that have a different amino acid at one or more position when compared to the sequence of the wild-type enzyme. In describing such mutants, two letters separated by a number indicate the amino acid mutations made. The letters are single-letter amino acid codes, and the numbers are the amino acid residue positions in the intact, wild-type enzyme. For example, GST-XD4 is a fusion protein containing a fragment, XD4, that has the same sequence as a specific part of the wild-type v-Src. In the designation GST-XD4(V323A, I338A), the valine in the sequence of v-Src fragment XD4 that represents position 323 in the compete wild-type v-Src sequence has been replaced by alanine, and the isoleucine in the XD4 fragment that represents position 338 in the complete wild type v-Src sequence has also been replaced with alanine. Thus, the terms "mutant" and "engineered form" encompass portions of the wild-type enzyme containing the mutated amino acid or amino acids.

The term "A*TP" refers to a form of ATP in which additional atoms or groups of atoms are added to one or more positions of the ATP structure. In addition, A*TP means an analog of ATP which has one or more of its atoms removed to form a molecule which is smaller than ATP itself. A*TP does not necessarily mean a non-natural analog of ATP, for example GTP could be considered an analog of ATP for the purposes of this definition.

The phrase "functionally silent active site mutation" means that the mutation does not disrupt the normal cellular role of the protein. In other words, the "functionally silent" mutant should be able to completely, or at least significantly, be able to replace the biological role of the wild-type protein. For example, if a cell or organism is created in which the wild-type form of the protein is absent and then the "functionally silent" form of the enzyme is added into that cell or organism, this "mutant containing" cell or organism should be very similar if not identical in behavior (by any appropriate assay) to the original unmodified form of the cell or organism.

II. General Description

This invention provides specific protein kinase inhibitors. Selective protein kinase inhibitors are highly sought after as tools for studying cellular signal transduction cascades, yet few have been discovered due to the highly conserved fold of kinase catalytic domains. Through a combination of small molecule synthesis and protein mutagenesis a highly potent ($IC_{50}$=1.5 nM and uniquely specific inhibitor (4-amino-1-tert-butyl)-3-(1'-naphthyl)pyrazolo naphthyl)pyrazolo [3,4-d]pyrimidine) of a rationally engineered v-Src protein kinase (Ile338Gly v-Src) has been identified. Both the potency and specificity of this compound surpass those of any known Src family protein kinase inhibitors. The molecule strongly inhibits the engineered v-Src in whole cells but does not inhibit tyrosine phosphorylation in cells that express only wild type protein kinases. In addition, the inhibitor selectively disrupts transformation in cells that express the target v-Src. The structural degeneracy of kinase active site should allow the same complementary inhibitor/protein design strategy to be widely applicable across this entire enzyme super-family. Thus, this invention provides mutant tyrosine and ser/thr kinases.

This invention provides mutant protein kinases that are sensitive to the disclosed cell permeable inhibitors. The mutant protein kinases belong to the following sub-families: Src family (v-Src, Fyn), Abl family (c-Abl), $Ca^{+2}$/Calmodulin dependent family (CAMK IIα), and cyclin dependent family (CDK2 and Cdc28).

III. Protein Kinase Inhibitor

The present invention provides a protein kinase inhibitor represented by the following formula I:

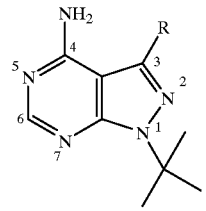

wherein R is a 1'-naphthyl, 2'-naphthyl; m-phenoxyphenyl; m-benzyloxyphenyl; m-(2', 6'-dichloro)benzyloxyphenyl; 3-piperonylpyrazolo; p-tert-butylphenyl; 1'-naphthylmethyl; 1'-naphthoxymethyl; or 2'-naphthylmethyl.

In one embodiment the naphthyl is a naphthylpyrazolo, pyrimidine. In another embodiment the protein kinase inhibitor is represented by the formula 6a as set forth in FIG. 18. In another embodiment the protein kinase inhibitor is represented by the formula 6b as set forth in FIG. 18. In another embodiment the m-phenoxyphenyl is a m-phenoxyphenyl, pyrazolopyrimidine. In another embodiment the protein kinase inhibitor is represented by the formula 6c as set forth in FIG. 18. In another embodiment the m-benzyloxyphenyl is a m-benzyloxyphenyl, pyrazolopyrimidine. In another embodiment the protein kinase inhibitor is represented by the formula 6d as set forth in FIG. 18. In another embodiment the m-dichloro, benzyloxyphenyl is a m-dichloro, benzyloxyphenyl, pyrazolopyrimidine. In another embodiment the protein kinase inhibitor is represented by the formula 6e as set forth in FIG. 18. In another embodiment the 3-piperonyl is a 3-piperonyl, pyrazolopyrimidine. In another embodiment the protein kinase inhibitor is represented by the formula 6f as set forth in FIG. 18. In another embodiment the p-tert-butylphenyl is a p-tert-butylphenyl, pyrazolopyrimidine. In another embodiment the protein kinase inhibitor is represented by the formula 6g as set forth in FIG. 18. In another embodiment the naphthylmethyl is a naphthylmethyl, pyrazolopyrimidine. In another embodiment the protein kinase inhibitor is represented by the formula 6h as set forth in FIG. 18. In another embodiment the protein kinase inhibitor is represented by the formula 6j as set forth in FIG. 24. In another embodiment the naphthoxymethyl is a naphthoxymethyl, pyrazolopyrimidine. In another embodiment the protein kinase inhibitor is represented by the formula 6i as set forth in FIG. 18.

This invention provides a src family kinase inhibitor, where the inhibitor is 4-amino-1-(tert-butyl)-3-(1'-naphthyl)pyrazolo[3,4-d]pyrimidine (6a);

4-amino-1-(tert-butyl)-3-(2'-naphthyl)pyrazolo[3,4-d]pyrimidine (6b);

4-amino-1-(tert-butyl)-3-(m-phenoxyphenyl)pyrazolo[3,4-d]pyrimidine (6c);

4-amino-1-(tert-butyl)-3-(m-benzyloxyphenyl)pyrazolo[3,4-d]pyrimidine (6d);

4-amino-1-(tert-butyl)-3-(m-(2',6'-dichloro)benzyloxyphenyl) pyrazolo[3,4-d]pyrimidine (6e);

4-amino-1-(tert-butyl)-3-piperonylpyrazolo[3,4-d]pyrimidine (6f);

4-amino-1-(tert-butyl)-3-(p-tert-butylphenyl)pyrazolo[3,4-d]pyrimidine (6g);

4-amino-1-(tert-butyl)-3-(1'-naphthylmethyl)pyrazolo[3,4-d]pyrimidine (6h);

4-amino-1-(tert-butyl)-3-(1'-naphthoxymethyl)pyrazolo[3,4-d]pyrimidine (6i); or 4-amino-1-(tert-butyl)-3-(2'-naphthylmethyl)pyrazolo[3,4-d]pyrimidine (6j).

As demonstrated herein all starting materials and synthetic reagents were purchased from commercial suppliers unless otherwise noted. Acid chlorides that were not readily commercially available (3c, 3d, 3e, 3h, 3i) were synthesized by treating the corresponding carboxylic acids with excess oxalyl chloride and catalytic DMF in diethyl ether. All PP1 analogues were synthesized according to Henefeld, et al. The group of modified inhibitors was screened against the catalytic domain of the target kinase, I338G v-Src, which was expressed in bacteria and purified as a gluthathione-S-transferase (GST) fusion protein. All of the $C^3$ derivatized analogues are more potent inhibitors of I338G v-Src than the most potent molecule (compound 3g, $IC_{50}$=430 nM, FIG. 14) identified from the first generation panel of $N^4$ derivatized compounds (see FIG. 14). Four of the molecules (6a, 6b, 6d, 6h) inhibit the target kinase at low nM concentrations with the two naphthyl isomers (6a, 6b) exhibiting the greatest potency ($IC_{50}$=1.5 nM). Under the conditions of our assay the parent molecule, PP1, inhibited its optimal target, Fyn, at only $IC_{50}$=30 nM. This data shows that an inhibitor design strategy combining enzyme engineering with directed small molecule synthesis can not only match the potency of molecules identified through screening of large libraries, but can lead to a significant increase (20 fold in the case of 6a, 6b) in affinity over previously optimized inhibitors of wild type kinase. Compounds having the formula of 6a and 6b are the most potent inhibitors of any Src family protein kinase that have been reported to date. Compound 6h and 6j are more orthogonal to wild-type kinases and is of medium potency. They are not as potent as 6a and 6b, but since they bind very poorly to wild-type kinases, they are ultimately very useful for inhibiting mutant kinases.

The present invention provides a pharmaceutical composition comprising a protein kinase inhibitor represented by the following formula I:

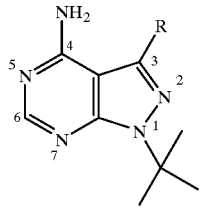

where R is a 1'-napthyl; 2'-naphthyl; m-phenoxyphenyl;m-benzyloxyphenyl; m-(2',6'-dichloro) benzyloxyphenyl; 3-piperonylpyrazolo; p-tert-butylphenyl; 1'-naphthylmethyl; 1'-naphthoxymethyl; or 2'-naphthylmethyl; and a suitable diluent or carrier.

In one embodiment the naphthyl is a naphthylpyrazolo, pyrimidine. In another embodiment the protein kinase inhibitor is represented by the formula 6a as set forth in FIG. 18. In another embodiment the protein kinase inhibitor is represented by the formula 6b as set forth in FIG. 18. In another embodiment the protein kinase inhibitor is represented by the formula 6c as set forth in FIG. 18. In another embodiment the m-benzyloxphenyl is a m-benzyloxyphenyl, pyrazolopyrimidine. In another embodiment the protein kinase inhibitor is represented by the formula 6d as set in FIG. 18. In another embodiment the m-dichloro, benzyloxyphenyl is a m-dichloro, benzyloxyphenyl, pyrazolopyrimidine. In another embodiment the protein kinase inhibitor is represented by the formula 6e as set forth in FIG. 18. In another embodiment the 3-piperonyl is a 3-piperonyl, pyrazolopyrimidine. In another embodiment the protein kinase inhibitor is represented by the formula 6f as set forth in FIG. 18. In another embodiment the p-tert-butylphenyl is a p-tert-butylphenyl, pyrazolopyrimidine. In another embodiment the protein kinase inhibitor is represented by the formula 6 g as set forth in FIG. 18. In another embodiment the naphthylmethyl is a naphthylmethyl, pyrazolopyrimidine. In another embodiment the protein kinase inhibitor is represented by the formula 6h as set forth in FIG. 18. In another embodiment the protein kinase inhibitor is represented by the formula 6j as set forth in FIG. 24. In another embodiment the naphthoxymethyl is a naphthoxymethyl, pyrazolopyrimidine. In another embodiment the protein kinase inhibitor is represented by the formula 6i as set forth in FIG. 18.

This invention provides a pharmaceutical composition comprising a src family protein kinase inhibitor, wherein the inhibitor is 4-amino-1-(tert-butyl)-3-(1'-naphthyl)pyrazolo[3,4-d]pyrimidine (6a);

4-amino-1-(tert-butyl)-3-(2'-naphthyl)pyrazolo[3,4-d]pyrimidine (6b);

4-amino-1-(tert-butyl)-3-(m-phenoxyphenyl)pyrazolo[3,4-d]pyrimidine (6c);

4-amino-1-(tert-butyl)-3-(m-benzyloxyphenyl)pyrazolo[3,4-d]pyrimidine (6d);

4-amino-1-(tert-butyl)-3-(m-(2',6'-dichloro) benzyloxyphenyl) pyrazolo[3,4-d]pyrimidine (6e);

4-amino-1-(tert-butyl)-3-piperonylpyrazolo[3,4-d]pyrimidine (6f);

4-amino-1-(tert-butyl)-3-(p-tert-butylphenyl)pyrazolo[3,4d]pyrimidine (6g);

4-amino-1-(tert-butyl)-3-(1'-naphthylmethyl)pyrazolo[3,4-d]pyrimidine (6h);

4-amino-1-(tert-butyl)-3-(1'-naphthoxymethyl)pyrazolo[3,4-d]pyrimidine (6i); or 4-amino-1-(tert-butyl)-3-(2'-naphthylmethyl)pyrazolo[3,4-d]pyrimidine (6j); and a suitable carrier or diluent.

This invention provides a method of disrupting transformation in a cell that expresses the target mutant v-Src comprising contacting the cell with a protein kinase inhibitor represented by the following formula I:

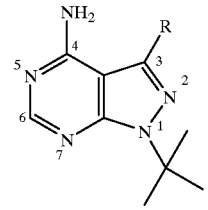

wherein R is a 1'-naphthyl; 2'-naphthyl; m-phenoxyphenyl; m-benzyloxyphenyl; m-(2',6'-dichloro)benzyloxyphenyl; 3-piperonylpyrazolo; p-tert-butylphenyl; 1'-napthylmethyl; 1'-naphthoxymethyl; or 2'-napthylmethyl.

In one embodiment the naphthyl is a naphthylpyrazolo, pyrimidine. In another embodiment the protein kinase inhibitor is represented by the formula 6a as set forth in FIG. 18. In another embodiment the protein kinase inhibitor is represented by the formula 6b as set forth in FIG. 18. In another embodiment the m-phenoxyphenyl is a m-phenoxyphenyl, pyrazolopyrimidine. In another embodiment the protein kinase inhibitor is represented by the formula 6c as set forth in FIG. 18. In another embodiment the m-benzyloxyphenyl is a m-benzyloxyphenyl, pyrazolopyrimidine. In another embodiment the protein kinase inhibitor is represented by the formula 6d as set forth in FIG. 18. In another embodiment the m-dichloro, benzyloxyphenyl is a m-dichloro, benzyloxyphenyl, pyrazolopyrimidine. In another embodiment the protein kinase inhibitor the 3-piperonyl is a 3-piperonyl, pyrazolopyrimidine. In another embodiment the protein kinase inhibitor is represented by the formula 6f as set forth in FIG. 18. In another embodiment the p-tert-butylphenyl is a p-tert-butylphenyl,pyrazolopyrimidine. In another embodiment the protein kinase inhibitor is represented by the formula 6g as set forth in FIG. 18. In another embodiment the naphthylmethyl is a naphthylmethyl, pyrazolopyrimidine. In another embodiment the protein kinase inhibitor is represented by the formula 6h as set forth in FIG. 18. In another embodiment the protein kinase inhibitor is represented by the formula 6j as set forth in FIG. 24. In another embodiment the naphthoxymethyl is a naphthoxymethyl, pyrazolopyrimidine. In another embodiment the protein kinase inhibitor is represented by the formula 6i as set forth in FIG. 18.

This invention provides a method of disrupting transformation in a cell that expresses the target mutant v-Src comprising contacting the cell with a pharmaceutical composition comprising a protein kinase inhibitor represented by the following formula I:

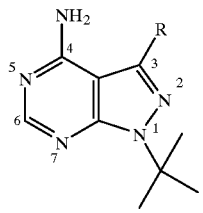

wherein R is a 1'-naphthyl; 2'-naphthyl; m-phenoxyphenyl; m-benzyloxyphenyl; m-(2',6'-dichloro)benzyloxyphenyl; 3-piperonylpyrazolo; p-tert-butylphenyl; 1'-naphthylmethyl; 1'-naphthoxymethyl; 2'-naphthylmethyl; and a suitable diluent or carrier.

In one embodiment the naphthyl is a naphthylpyrazolo, pyrimidine. In another embodiment the protein kinase inhibitor is represented by the formula 6a as set forth in FIG. 18. In another embodiment the protein kinase inhibitor is represented by the formula 6b as set forth in FIG. 18. In another embodiment the m-phenoxyphenyl is a m-phenoxyphenyl, pyrazolopyrimidine. In another embodiment the protein kinase inhibitor is represented by the formula 6c as set forth in FIG. 18. In another embodiment the protein kinase inhibitor is represented by the formula 6d as set forth in FIG. 18. In another embodiment the m-dichloro,benzyloxyphenyl is a m-dichloro, benzyloxyphenyl,pyrazolopyrimidine. In another embodiment the protein kinase inhibitor is represented by the formula 6e as set forth in FIG. 18. In another embodiment the 3-piperonyl is a 3-piperonyl, pyrazolopyrimidine. In another embodiment the protein kinase inhibitor is represented by the formula 6f as set forth in FIG. 18. In another embodiment the p-tert-butylphenyl is a p-tert-butylphenyl, pyrazolopyrimidine. In another embodiment the protein kinase inhibitor is represented by the formula 6g as set forth in FIG. 18. In another embodiment the naphthylmethyl is a naphthylmethyl,pyrazolopyrimidine. In another embodiment the protein kinase inhibitor is represented by the formula 6h as set forth in FIG. 18. In another embodiment the protein kinase inhibitor is represented by the formula 6j as set forth in FIG. 24. In another embodiment the napthoxymethyl is a naphthoxymethyl, pyrazolopyrimidine. In another embodiment the protein kinase inhibitor is represented by the formula 6i as set forth in FIG. 18.

As demonstrated herein, wild type v-Src expressing cells that are treated with 6a appear indistinguishable from untreated wild type cells suggesting that 6a has no effect on this non-mutant cell line. However, cells expressing the target kinase have clear actin fibers and appear indistinguishable from normal NIH3T3 fibroblasts when incubated with 250 nM 6a for 16 hours. From this data it is clear that small molecule inhibition of v-Src's catalytic activity is sufficient to block its role in onocogenesis.

The lower alkyl groups on the compound represented by formula I which may be included contain 1–6 carbon atoms and include methyl, ethyl, propyl, butyl, pentyl, hexyl, and the corresponding branched-chain isomers thereof. These groups are optionally substituted by one or more halo hydroxy, amino or lower alkylamino groups. Where the possibility exists for substitution of a phenyl or aryl ring, the position of the substituents may be ortho, meta, or para to the point of attachment of the phenyl or aryl ring to the nitrogen of the hydrazine group. Preferably, the substituents are para or meta to the point of attachment, and where more than one is present on the same ring, they are preferably in the para and meta positions. The halo atoms in the above formula may be fluoro, chloro, bromo or iodo. The lower alkoxy groups contain 1–6, and preferably 1–3, carbon atoms and are illustrated by methoxy, ethoxy, n-propoxy, isopropoxy and the like. Further, as contemplated herein the t-butyl group may be substituted or modified with any of the above.

The compounds of the instant invention may include labels or markers such as fluorescent dyes in a range of blue, red, green, yellow, colors, and especially blue and green colors. The color of fluorescence may be different from the absorption color. Fluorescent pigments possess high luminenscence and advantageous application properties, for example, high light fastness and a low migration tendency. The possession of fluorescent properties further enables the use of the compounds of the instant invention in a variety of medical, pharmaceutical and diagnostic applications. The compounds of the instant invention can also be utilized to label various therapeutic agents to enable their disposition in the body. As such, therapy with such labeled therapeutic agents can be closely monitored with respect to target organs and tissues. This is particularly useful in the treatment of various cancers, especially those of a solid tumor type, where localization of the chemo-therapeutic agent is extremely important and dosage due to the possibility of side-effects, must be closely monitored.

The inhibitors of the present invention belong to the family of pyrazolopyrimidines. Pyrazolopyrimidines are useful in the treatment and prevention of respiratory diseases represented by asthma (U.S. Pat. No. 5,942,515). Moreover, amino-pyrazolopyrimidine derivatives have been used as protein kinase inhibitors for inhibiting cell proliferation and are thus useful in the treating tumors and hyperproliferative diseases (WO 9631510). This family of inhibitors has also been shown to be useful in the treatment of cardiovascular and urogenital diseases (DE 19709126 A) and for treating ischaemia, arthritis and pain (WO 9640707). Thus, the inhibitors of the present invention are also expected to have therapeutic applications.

In addition, the present invention provides a solution to the above-described problems by providing materials and methods by which a single protein kinase can be specifically inhibited without the simultaneous inhibition of another protein kinase.

IV. Engineered Kinase and Engineered Multi-Substrate Enzymes

In a first aspect, the present invention involves the engineering of kinase and other multi-substrate enzymes such that they can utilize modified substrates which are not as readily used by their wild-type forms. The invention further provides such chemically modified nucleotide triphosphate substrates, methods of making them, and methods of using them. The methods of the present invention include methods for using the modified substrates along with the engineered kinase to identify which protein substrates the kinase act upon, to measure the extent of such action, and to determine if test compounds can modulate such action.

In a further aspect, the invention provides engineered protein kinase which can bind inhibitors that are not as readily bound by the wild-type forms of those enzymes. Methods of making and using all such engineered kinase are also provided. The invention further provides such inhibitors, methods of making them, and methods of using them. The methods of the present invention include methods for using the inhibitors along with the engineered kinase to identify which protein substrates the kinase act upon, to measure the kinetics of such action, and to determine the biochemical and cellular effects of such inhibition. They also relate to the use of such inhibitors and engineered kinase to elucidate which kinase may be involved in disease; these kinase can then become the subject to efforts to design or discover more traditional specific inhibitors of their wild-type forms, which may prove to be valuable in treating the kinase-related disease or disorder.

Furthermore, methods are provided for inserting the engineered kinase into cells or whole animals, preferably in place of the corresponding wild-type kinase, and then using the inhibitor to which it has been adapted as a tool for study of the disease-kinase relationship, and ultimately, as a drug for the treatment of the disease.

The present invention also more generally relates to engineered forms of multi-substrate enzymes which covalently attach part or all of at least one (donor) substrate to at least one other (recipient) substrate. These engineered forms will accept modified substrates and inhibitors that are not as readily bound by the wild-type forms of those enzymes.

The invention also relates to methods for making and using such engineered enzymes as well as modified donor substrates. The methods of the present invention include methods for using the modified substrates and inhibitors along with the engineered enzymes to identify which substrates the enzymes act upon, to measure the kinetics of such action, and in the instance of the modified substrates, to determine the recipient substrates to which part or all of the donor substrate becomes attached, to measure the extent of such action, and to identify and measure the extent of modulation thereof by test compounds.

In the instance of inhibitors, the methods seek to determine the biochemical and cellular effects of such inhibition. The methods also extend to the use of such inhibitors and engineered enzymes to elucidate which enzymes may be involved in disease; these enzymes can then become the subject of efforts to design or discover specific inhibitors of their wild-type forms, which may prove to be valuable in treating the enzyme-related disease or disorder. Furthermore, methods are provided for inserting the engineered enzyme into cells or whole animals, preferably in place of the corresponding wild-type enzyme, and then using the inhibitor to which it has been adapted as a tool for study of the disease-enzyme relationship, and ultimately, as a drug for the treatment of the disease.

According to the present invention, through enzyme engineering a structural distinction can be made between the nucleotide binding site of a protein kinase of interest, and the nucleotide binding sites of other kinase. This distinction allows the engineered kinase to use a nucleotide triphosphate or an inhibitor that is not as readily bound by the wild-type form of that kinase, or by other kinase. In a preferred embodiment with respect to the inhibitor, the inhibitor used is one that is "orthogonal" to the "natural" nucleotide triphosphate substrate for that kinase, or is orthogonal to a less specific inhibitor (e.g., one which is readily bound by the wild-type form of that kinase). The term "orthogonal," as discussed above, means that the substrate or inhibitor is similar in structure (including those that are geometrically similar but not chemically similar, as described below), but differs in a way that limits its ability to bind to the wild-type form.

V. Orthogonal Nucleotide Triphosphate

An engineered kinase made according to the present invention will be able to use an orthogonal nucleotide triphosphate substrate that is not as readily used by other, non-engineered kinase present in cells. Preferably, it will be able to use an orthogonal nucleotide triphosphate that is not substantially used by other kinase; and most preferably, it will be able to use an orthogonal nucleotide triphosphate substrate that cannot be used at all by other kinase. By labeling the phosphate on the orthogonal substrate, e.g., by using radioactive phosphorous ($P^{32}$), and then adding that labeled substrate to permeabilized cells or cell extracts, the protein substrates of the engineered kinase will become labeled, whereas the protein substrates of other kinase will be at least labeled to a lesser degree; preferably, the protein substrates of the other kinase will not be substantially labeled, and most preferably, they will not be labeled at all.

The detailed description and examples provided below describe the use of this strategy to uniquely tag the direct substrates of the prototypical protein kinase, v-Src. Through protein engineering a chemical difference has been made in the amino acid sequence which imparts a structural distinction between the nucleotide binding site of the modified v-Src and that of all other kinase. The v-Src kinase was engineered to recognize an ATP analog (A*TP), $\underline{N}^6$-(cyclopentyl)ATP, which is orthogonal to the nucleotide substrate of wild-type kinase. The generation of a v-Src mutant with specificity for an orthogonal A*TP substrate allows for the direct substrates of v-Src to be uniquely radiolabeled using [$\gamma$-$^{32}$P] $\underline{N}^6$-(cyclopentyl)ATP, because it is able to serve as substrate to the engineered v-Src kinase, but is not substantially able to serve as substrate for other cellular kinase.

The detailed description and examples provided below describe the use of this strategy to uniquely identify the direct substrates of the prototypical protein kinase, v-Src. Through protein engineering a chemical difference has been made in the amino acid sequence which imparts a new structural distinction between the nucleotide binding site of the modified v-Src and that of all other kinase. The engineered v-Src kinase that have been made and presented herein bind to an orthogonal analog of the more general kinase inhibitor PP3: the compound N-4 cyclopentyl PP3 (FIG. 11A). The generation of a v-Src mutant with specificity for such an inhibitor allows for the mutant to be inhibited, whereas other kinase in the same test system are not substantially inhibited, not even the wild-type form of that same kinase.

VI. Mutant Protein Kinase

As is apparent from the foregoing, it is one object of the present invention to provide a mutant protein kinase which accepts an orthogonal nucleotide triphosphate analog as a phosphate donor substrate. Another object of the present invention is to provide a nucleotide sequence which encodes such a mutant protein kinase; and it is a further object to provide a method for producing such a nucleic acid sequence. It is also an object of the invention to provide methods for producing such a mutant protein kinase, for example, by expressing such a nucleic acid sequence. It is also an object of the present invention to provide such orthogonal nucleotide triphosphates and methods for their synthesis, including $N^6$-(cyclopentyl)ATP, $N^6$-(cyclopentyloxy)ATP, $N^6$-(cyclohexyl)ATP, $N^6$-(cyclohexyloxy)ATP, $N^6$-(benzyl)ATP, $N^6$-(benzyloxy)ATP, $N^6$-(pyrolidino)ATP, and $N^6$-(piperidino)ATP, (27).

It is yet another object of the invention to provide a method for determining whether a test compound positively or negatively modulates the activity of a protein kinase with respect to one or more protein substrates. More particularly, and in accordance with the further aspect of the invention, it is a primary object to provide a mutant protein kinase which binds to and is inhibited by an inhibitor, which inhibitor less readily binds to or inhibits the corresponding wild-type kinase.

A further object of the present invention is to provide a nucleotide sequence which encodes such a mutant protein kinase; and it is a further object to provide a method for producing such a nucleic acid sequence. It is also an object of the invention to provide methods for producing such a mutant protein kinase, for example, by expressing such a nucleic acid sequence. It is another object of the present invention to provide such inhibitors, such as the compound N-4 cyclopentyl PP3, and methods for their synthesis. Another object is to provide a method for determining what are the substrates for a given protein kinase. It is yet another object of the invention to provide a method for determining whether specific inhibition of a particular kinase produces a biochemical or phenotypic effect in a test systems such as a cell-free extracts, cell cultures, or living multicellular organisms. It is a further object of the invention to provide a method to determine whether inhibition of a particular kinase might have therapeutic value in treating disease. It is yet another object to provide methods for the study of the activity, kinetics, and catalytic mechanisms of a kinase by studying the inhibition of the corresponding mutant of the present invention. A further object is to provide methods of preventing and treating kinase-mediated diseases by introducing an inhibitor-adapted mutant kinase of the present invention into a diseased organism, and preferably diminishing or, most preferably, depleting the organism of the wild-type enzyme; and then administering the inhibitor to regulate the activity of the now disease-mediating mutant kinase so as to diminish or eliminate the cause or symptoms of the disease.

VII. Multi-Substrate Enzymes

Based upon the foregoing and the detailed description of the present invention provided below, one of ordinary skill in the art will readily recognize that the present invention can be used more generally to study multi-substrate enzymes which covalently transfer a donor substrate or portion thereof to a recipient substrate, as do the kinase, and enzymes which do not bind two substrates or transfer a group. Such applications of the present invention are also further described in the detailed description which follows. Accordingly, it is yet a further object of the present invention to provide a mutant multi-substrate enzyme which binds to an inhibitor, which inhibitor is less readily bound to the wild-type enzyme or to other enzymes with similar activity.

It is another object of the invention to provide a nucleotide sequence which encodes such a mutant multi-substrate enzyme; and it is a further object to provide a method for producing such a nucleic acid sequence. It is also an object of the invention to provide methods for producing such a mutant multi-substrate enzyme, for example, by expressing such a nucleic acid sequence. It is also an object of the present invention to provide such inhibitors and methods for their synthesis. Another object is to provide a method for determining what are the substrates for a given multi-substrate enzyme. It is yet another object of the invention to provide a method for determining whether specific inhibition of a particular multi-substrate enzyme produces a biochemical or phenotypic effect in a test system such as cell-free extracts, cell cultures, or living multicellular organisms. It is a further object of the invention to provide a method to determine whether inhibition of a particular multi-substrate enzyme might have therapeutic value in treating disease.

The present invention involves the engineering of kinase and other multi-substrate enzymes such that they can become bound by inhibitors which are not as readily bound by their wild-type forms. Modified substrates and mutant enzymes that can bind them have been used to study an elongation factor (41) and a receptor for cyclophilin A (42). However, prior to the present invention, it was not known how, or even if, multi-substrate enzymes which covalently attach part or all of a donor substrate onto a recipient substrate could be engineered to bind to an inhibitor, yet still retain at least some catalytic activity and at least some specificity for the recipient substrate in the absence of the inhibitor. The present invention is that this can be done, as explained below; and this invention for the first time opens the door to the selective inhibition of individual kinase, which are not only important tools for understanding of the kinase cascades and other complex catalytic cellular mechanisms, but also may provide avenues for therapeutic intervention in diseases where those mechanisms come into play.

It is yet another object to provide methods for the study of the activity, kinetics, and catalytic mechanisms of a multi-substrate enzyme by studying the inhibition of the corresponding mutant of the present invention. A further object is to provide a method of preventing and treating multi-substrate enzyme-mediated diseases by introducing an inhibitor-adapted multi-substrate enzyme of the present invention into a diseased organism, and preferably diminishing or, most preferably, depleting the organism of the wild-type enzyme; and then administering the inhibitor to regulate the now disease-mediating mutant enzyme so as to diminish or eliminate the cause or symptoms of the disease.

As mentioned above, the present invention is not limited to mutant kinase, orthogonal inhibitors, and their synthesis and use. The present invention will work just as well for other multi-substrate enzymes which covalently transfer part or all of one substrate, here called the donor, to another substrate, here called the recipient; and there are surely more such enzymes yet to be discovered. In any such instance, one of skill in the art who has studied the present specification will well appreciate the applicability of the present invention to such enzymes. The tasks at hand in such an instance are quite similar to those described in detail here for the kinase. First, it is necessary to identify what the donor substrate is, and/or to identify compounds which can inhibit that kinase, even if it is not specific for that kinase.

Second, it is necessary to consider where a bulky substituent might be added to the substrate of the inhibitor such that it will not bind as readily to the wild-type kinase, or preferably will not bind substantially to the wild-type kinase, and preferably, will not bind at all. Of course, it is not really necessary, in the case of kinase or in other multi-substrate enzymes as described above, to be restrictive with respect to which analogs of these to make; one can make a variety of them, even including some that seem unlikely to be ideal, and determine by screening which one or ones are the best. Further guidance regarding how to do this can be gained from the examples below. The inhibition assay, the results of which are shown in FIG. 6, is a non-limiting example of an assay particularly well suited to such screening.

The third step is to engineer the kinase such that one or more amino acid in the three-dimensional location where the bulky group would be expected to be if the analog did bind are replaced with amino acids having less bulky side chains, thus "making room" for the bulky moiety of the inhibitor. Steps two and three can, of course, be carried out in the reverse order.

For example, transferase enzymes would be most interesting candidates for study using the present invention. One could, following the teachings provided herein, prepare mutant transferases which will accept orthogonal inhibitors, and these could be used together in order to identify the direct substrates of one particular transferase in a large gamily of homologous transferases, by the methods described above for the kinase. The family of methyl-transferases would be of clear interest, and could quite easily be studied using the methods provided herein. These enzymes all use the same nucleotide based cofactor, S-adenosylmethionine (AdoMet), as a methyl (CH3) group donor. The different members of the family can transfer the methyl group of AdoMet to a wide variety of cellular components such as proteins (in which case the methyl group is added to arginine, aspartate, and glutamate side chains), DNA (in which case the methyl group is added to the C-5 position of cytosine, or the N-7 of guanine), to components of cell membrane components such as phospholipids, and also to a number of small amine containing hormones. Many new targets are also being identified for this diverse family of enzymes. The present invention provides the opportunity to decipher the tremendously complex cellular mechanisms that these enzymes are carrying out.

For example, one could synthesize a set of AdoMet analogs that contain additional bulky hydrophobic groups at the N-6 position, or at other ring positions, which would make the analogs orthogonal, and thus not be accepted as readily by wild-type methyltransferases as is the natural substrate; and the structure in the region of the transferred methyl group might be altered such that the methyl group is more chemically resistant to transfer; or, for example, S-adenosylcysteine might be used as the starting compound instead. Using the crystal structures of DNA methyltransferase M.Hhal and the catechol methyltransferase catechol O-methyl-transferase (COMT), one can identify those amino acids in the adenine binding pocket which are candidates for mutation as was done herein for the protein kinase; and one of ordinary skill in the art should readily be able to identify a set of residues to mutate in order to accommodate the bulky hydrophobic groups of one or more of the orthogonal substrates.

For example, one might mutate large hydrophobic groups to smaller alanine or glycine residues, or replace hydrogen bonding amino acids with others that compliment the orthogonal purine analogs of AdoMet. Of course, a myriad of other possible mutations may work as well, and all would be within the scope of the present invention. In addition, from sequence alignments and crystal structures of methyltransferases, it is known that they have a common catalytic domain structure (70); so this approach is not limited to M.Hhal and COMT, but should be equally applicable to other methyl transferases.

After a methyltransferase mutant is identified which accepts an orthogonal inhibitor, radiolabeled AdoMet can then be synthesized which contains a C-14 labeled methyl group attached to the sulfur atom of AdoMet. When this radiolabeled analog is added to cells expressing one mutant methyltransferase, the direct substrates (e.g., protein or DNA, or polyamines) of all methyltransferases in the sample will be specifically radiolabeled with the C-14 methyl group. But when this is done in the presence of the orthogonal inhibitor, the specific substrates for the methyltransferase of interest will be less labeled in comparison to the sample not containing the inhibitor; preferably, they will not be substantially labeled, and most preferably, will not be labeled at all. In this way, or through the use of other methods described herein for the study of the kinase, direct substrates of methyltransferases can be identified which are important in cancer, embryonic development, chemotaxis of poly morphonuclear leukocytes, or in neurological disorders. In addition, the methods of the present invention can then be used to determining whether compounds can be identified that modulate the activity of the enzyme. The several other aspects of the present invention, although perhaps not described here, could also be applied to the methyl transferases, and also to other multi-substrate enzymes.

The foregoing discussion of the application of the present invention to the methyl transferases is not intended to limit the scope of the present invention, but to illustrate of the applicability of the present invention to multi-substrate enzymes other than the protein kinase. As will be appreciated by those in the art, the present invention could be applied similarly to other multi-substrate enzymes using similar approaches.

As described in the examples below, using the present invention the utility of a v-Src kinase which shows high specificity for a synthetic inhibitor while maintaining its wild-type specificity for tyrosine containing peptides and proteins was demonstrated and made, thus satisfying the initial research goals. By exploiting the highly conserved nature of the ATP binding site across the kinase superfamily and the availability of structural information from other protein kinase, novel inhibition specificity for v-Src was engineered without any detailed structural information about v-Src itself. That an unrelated kinase was used as a blueprint for designing orthogonal ATP analogs to tag the direct cellular substrates of v-Src, and have prepared inhibitors from like origins, demonstrates that this approach should work for other kinase as well.

VIII. Modified Inhibitors and Substrates

The inhibitors contemplated by this invention may be useful in studies directed towards developing other useful mutants of this and other kinase, and for the several methods described elsewhere herein. However, the scope of the present invention is not limited to the use of these particular inhibitors, and those of ordinary skill in the art will recognize that many other possible structures could be substituted for or supplement those described herein. For example, different, simpler, and even more complex aliphatic or aromatic groups could be added to the $N^6$ position of ADP or to the $N^4$ position of PP3. In addition, the inhibitors of the present invention are not limited to modifications of nucleotides at the $N^6$ position or modifications of PP3 at the $N^4$ position. Chemical means to modify various positions on such compounds are known, and any of the resulting derivatives would be within the scope of the present invention; it is even possible to make changes or substitutions in their ring structures. Exemplary variants are presented herein, and particular reference is made to FIG. 12 where both analogs and data relating to their activity is set forth. Of course, the use of such inhibitors may require that different positions in the protein sequence of the kinase be modified in order to make an engineered kinase that will bind to them, but such different modifications are well within the scope of the present invention.

In addition, it is important to note that the inhibitors of the present invention are not limited to ADP and PP3 derivatives. For example, it should be possible to utilize derivatives of other natural nucleotide phosphate donor substrate as such inhibitors. For studying some kinase, different analog bases may in fact be preferred. For example, it is know that some kinase utilize GTP as phosphate donor substrate and energy source; to make inhibitors for engineered forms of such kinase, analogs of guanosine diphosphate would be suitable. Furthermore, it is well known that related compounds (e.g., other bases) and compounds chemically unrelated to the natural substrate can sometimes nevertheless bind to an active site, and can (but for the purposes of this invention need not), be acted upon or act upon other substrates through chemical catalysis by the enzyme. Sometimes they participate in the catalyzed reaction in the same way as the natural substrate, sometimes in different ways. Such compounds and their derivatives would be suitable starting points for the design of inhibitors that are orthogonal to them, and which would be within the scope of the present invention. Similarly, other known kinase inhibitors can be used as a starting point for synthesis of inhibitors of the present invention, such as those whose structures appear in FIG. 9. Of course, even derivatives of inhibitors that are currently unknown would, once identified, be suitable core structures for the design of inhibitors of the present invention, as illustrated herein and made a part hereof.

Furthermore, the inhibitors of the present invention are not limited to those made by chemical synthetic means, but also include compounds which may be found in nature, and which can serve that role, some of which are discussed above. In addition, those of ordinary skill in the art will appreciate that there are other variations besides those set forth here, and that these are all within the scope of the present invention.

The inhibitors that are candidates for use in accordance with the present invention can conveniently be screened to determine the extent to which they are accepted by wild-type kinase, using a screening procedure such as that set forth in Example 13 below, or by a screening procedure involving the use of a cell or cells which are rich in protein kinase activity as set forth in Example 9 herein. By such an assay, one can determine whether each inhibitor is bound by wild-type kinase to a lesser degree than the engineered kinase, or preferably, if the wild-type kinase do not substantially bind to that inhibitor, or most preferably, do not bind the inhibitor at all. For those substrates that are less readily bound, it may be worthwhile to try to engineer the kinase of interest so that it will more readily bind to them. Of course, one could make the engineered kinase first and then assay it along side the wild-type enzyme to determine whether it uses a given orthogonal substrate better than the wild-type kinase; this was the approach used in Example 13. However, under most circumstances, pre-screening as described above will be preferred. Of course, other assay approaches will be apparent to those in the field, and the use of such assays would be within the scope of the present invention.

IX. Reengineering a Kinase

There are several criteria that should be satisfied in reengineering a kinase in order to uniquely tag its authentic substrates in the presence of wild-type tyrosine and serine/threonine kinase. The engineered kinase should: (1) accept an ATP analog (A*TP) that is utilized less readily by wild-type protein kinase; preferably, accept an A*TP that is not substantially utilized by wild-type kinase; and most preferably, accept an A*TP that is not utilized by wild-type kinase at all; (2) preferably, use the A*TP analog with high catalytic efficiency; and (3) preferably, have reduced catalytic efficiency for the natural nucleotide substrate (ATP) so that in the presence of cellular levels of ATP (1–2 mM) the mutated kinase would preferentially utilize A*TP as the phosphodonor. If such engineered kinase are to be used to study the protein substrate specificity of the wild-type kinase, then these criteria must be met without substantially altering the protein target specificity of the kinase.

Likewise several criteria should be satisfied in reengineering a kinase in order that it will be inhibited by the inhibitors of the present invention. The engineered kinase should: (1) bind to an inhibitor which is bound less readily by wild-type protein kinase; preferably, the inhibitor will not substantially bind to wild-type kinase; and most preferably, will not bind at all to wild-type kinase; (2) preferably, the engineered kinase will bind the inhibitor with high affinity (i.e., low $IC_{50}$). It is not generally of particular importance whether the inhibitor binds to the wild-type form of the kinase that corresponds to the engineered kinase, as such binding and the resulting inhibition would augment that of the engineered kinase. However, it is most likely that the wild-type form of that kinase will not bind the inhibitor any better than other wild-type kinase. If an inhibitable engineered kinase is to be used to study the protein substrate specificity of the wild-type kinase, or to replace the wild-type form of that kinase through gene therapy or other means, as further discussed below, then a further concern is that the above-described criteria must preferably be met without substantially altering the protein target specificity of the engineered kinase when compared with the corresponding wild-type form.

When viewed from the perspective of the state of the art when the present invention was made, it was not predictable whether it would be possible to satisfy all of these criteria simultaneously; in fact, it was doubtful, because the ATP binding site that is engineered is very close to the second substrate binding site, i.e., the peptide binding site. However, as shown by the examples below, all of these criteria, including the preferred criteria, were in fact met simultaneously when the described v-Src mutants were made, provided them with $N^6$(cyclopentyl)ATP and inhibited them using N4-cyclopentyl PP3.

Example 1 describes the twelve ATP analogs which were used in the studies on mutant v-Src, which are described in the further examples which follow. These orthogonal ATP analogs may be useful in studies directed towards developing other useful mutants of this and other kinase, and for the several methods described elsewhere herein. However, the scope of the present invention is not limited to the use of these particular ATP analogs, and those of ordinary skill in the art will recognize that many other possible orthogonal substrates could be substituted for or supplement those described herein. For example, different and even more complex aliphatic or aromatic groups could be added to the $N^6$ position of ATP. In addition, the orthogonal substrates of the present invention are not limited to modifications of nucleotides at the $N^6$ position. Chemical means to modify various positions on adenosine are known, and any of these would be within the scope of the present invention; and it is even possible to make changes or substitutions in the ring structures of nucleotides. Of course, the use of such orthogonal substrates may require that different positions in the protein sequence of the kinase be modified in order to make an engineered kinase that will bind to them, but such different modifications are well within the scope of the present invention.

In addition, it is important to note that the orthogonal substrates of the present invention are not limited to ATP derivatives. For studying different kinases, different analog bases may in fact be preferred. For example, it is known that some kinase utilize GTP as phosphate donor substrate and energy source; for studies of such kinase, analogs of guanosine triphosphate would be preferred. It is well known that compounds chemically unrelated to the natural substrate can sometimes nevertheless bind to an active site, and can even be acted upon or act upon other substrates through chemical catalysis by the enzyme. Sometimes they participate in the catalyzed reaction in the same way as the natural substrate, sometimes in different ways. Such compounds and their derivatives would also be within the scope of the terms "natural substrate" and "orthogonal substrate" as used herein.

Furthermore, the orthogonal substrates of the present invention are not limited to those made by chemical synthetic means, but also include compounds which may be found in nature, and which can serve that role. Those of ordinary skill in the art will appreciate that there are other variations besides those set forth here, and that these are all within the scope of the present invention.

The orthogonal nucleotides that are candidates for use in accordance with the present invention can conveniently be screened to determine the extent to which they are accepted by a wild-type kinase, using a screening procedure such as that set forth in Example 2 below. By such an assay, one can determine whether each orthogonal substrate is accepted by wild-type kinase to a lesser degree than the normal substrate for such kinase, or preferably, do not substantially accept that substrate, or most preferably, do not accept it at all. For those substrates that are least less readily accepted, it may be worthwhile to try to engineer the kinase of interest so that it will more readily accept them. Of course, one could make the engineered kinase first and then assay it along side the wild-type enzyme to determine whether it uses a given orthogonal substrate better than the wild-type kinase. However, under most circumstances, pre-screening such as is described in Example 2 will be preferred. Of course, other assay approaches will be apparent to those in the field, and the use of such assays would be within the scope of the present invention.

The design of an engineered v-Src is described in Example 3 below. As is described, the engineered form was designed by reference to the crystal structures of other kinases which have domains that are homologous to those found in most if not all kinase. As will be seen, the example mutant kinase described herein have been constructed as fragments of protein kinase, rather than as containing the entire sequences; but it was found there is no substantial difference in performance when the entire sequence is used. Of course, the concepts and the practicalities are the same whether fragments or whole kinase are used, and both are within the scope of the present invention. As such, the term "kinase" should be viewed as including the whole enzyme or a fragment of one, including when interpreting the claims.

Using this approach, it is possible to design similar mutants of virtually any other kinase, such as a protein kinase, a lipid kinase, or an aminoglycoside kinase. The method of doing this comprises the steps of: (a) identifying, from the amino acid the alignment of a kinase of interest with a kinase having a known kinase inhibitor (which may be non-specific for that kinase, specific for kinases generally but not for that kinase, or specific for that kinase), one or more amino acids which are close enough to a substituent on the bound phosphate donor substrate or inhibitor that would sterically restrict entry of a bulky substituent attached to that position in a putative orthogonal inhibitor; and (b) mutating a nucleotide sequence which encodes the wild-type protein kinase such that the nucleotide triplets encoding one or more of the identified amino acids, are converted to nucleotide triplets that encode amino acids having side chains that are sterically less bulky than the identified amino acids. The above-described method uses steric restriction of entry or exclusion as the criteria for deciding which amino acid(s) to change, and how to change them. However, the present invention is not so limited. It is also possible to engineer a kinase to change its ability to bind to an orthogonal substrate by considering other factors, such as hydrophobicity, hydrophilicity, ionic binding or repulsion, hydrogen bonding, forming covalent bonds between the enzyme and electrophilic groups on orthogonal substrates, etc.

The study of protein kinase using the present invention will be greatly facilitated by the vast knowledge regarding the domain structure of many different kinase, and their generally homologous sequences. The Protein Kinase Facts Book (71) provides protein sequence data for the three functional domains in literally hundreds of protein kinase, and this along with sequence information available in the primary literature, should greatly facilitate the further application of the present invention to the kinase. Similar information is available regarding other multi-substrate enzymes, which should facilitate their study and use according to the present invention.

Although the preferred method of the present invention involves the rational design of substrate analogs and mutant protein kinase, both could alternatively be made by use of methods known as combinatorial methods. There are many combinatorial methods of synthesizing organic compounds. Using one such method, one could synthesize nucleoside analogs on resin beads using sequential chemical steps, and then release them from the resin prior to phosphorylation to make the nucleotide triphosphates. After using such a method to make a collection or library of putative orthogonal substrates for mutants of v-Src kinase, other protein kinase, or other multi-substrate enzymes, the collection or library could be screened for particularly favorable binding or catalytic properties. This may allow for the more thorough search of structural, conformational, and electronic features of such putative orthogonal substrates. Moreover, it is often found that when larger numbers of analogs of a given substrate are investigated, an unexpectedly efficient substrate or inhibitor can be found Furthermore, sometimes the compounds which are the most desirable would not have been chosen if only well understood parameters were used to specifically design the best compound.

There are also many combinatorial methods known in the art for making protein mutants. These include "error prone" polymerase chain reaction (PCR), "sexual" PCR, or PCR using primers with random nucleotides as fixed positions in the protein sequence. Other sequence randomization methods might include using chemical mutagens of cDNA or plasmid DNA, or MutD type strains of bacteria, which are known to introduce mutations randomly in proteins that they express. It would be possible to carry out the present invention by exploiting such methods for making randomly mutated protein kinase or other multi-substrate enzymes, and then screening for one with particularly high activity with a particular orthogonal substrate, or with some or all of the putative orthogonal substrates made using combinatorial synthesis, as described in the paragraph above. The assay methods described in the examples below would be suitable for this purpose, and those in the art would be readily able to design alternative approaches.

These methods and other methods which are or may be developed to explore protein sequence space and the structural space of small organic molecules might be particularly useful for the technological application described here, where changing or altering both the protein and the putative inhibitor in order to find the best possible non-natural (i.e., orthogonal) fit. The use of any of these or any of the other methods described herein would be within the scope of the present invention.

The synthesis of one engineered kinase is described in Example 4. The focus of this effort was on amino acid side chains that were within about 4 Å of the $N^6$ of ATP; but there is nothing magical about that distance. Residues with side chains that are within about 1 Å, 2 Å, 3 Å, 5 Å, 6 Å, 7 Å, 8 Å, 9 Å, 10 Å, or lesser, greater or intermediate distances should also be considered as targets for modification. Amino acids with side chains that are within about 3 Å to about 6 Å would be preferred targets. Generally those amino acids with the closer side chains will be preferred over those with more distant side chains, as they would be expected to cause the greatest steric or other interference with the orthogonal substituent on the inhibitor; and those with the very closest side chains would be the most preferred.

Of course, there are many other ways to modify and express genetic sequences today then those used in the examples, such as site-directed mutagenesis. The use of any or all of these would be within the scope of the present invention. In addition, although the use of genetic engineering is today probably the preferred method to prepare such mutants, it is not the only way. For example, one could design an engineered kinase and then synthesize that protein by known methods of chemical peptide synthesis. Or, it may be possible to chemically modify a given enzyme in a specific location such that one or more side chain changes in size, hydrophobicity, or other characteristic, such that it can more readily utilize an orthogonal substrate. The use of all such methods are within the scope of the invention.

Example 7 describes testing which could be done to determine whether the engineered kinase had retained its protein substrate specificity. It is preferred that the wild-type protein substrate specificity be substantially retained if, as in the examples, the goal is to use the engineered kinase to study what substrates the kinase acts upon and to what degree it does so, or it is to be used to replace or supplement the corresponding wild-type kinase in vivo, e.g., through genetic engineering. However, although for such purposes it is important that the kinase still recognize the same substrates as the wild-type, it is not critical that it do so with the same kinetics; i.e., if it does so slower or faster, or to a greater or lesser degree, the engineered kinase may still have substantial value for such purposes. If the engineered kinase does not recognize the same protein substrates as the wild-type enzyme, it may have less value in studying the wild-type enzyme, but may still have substantial value in studying protein phosphorylation and kinase in general, and would still be within the scope of the invention.

Of course, the particular assays used in Example 7, although useful, need not be used. Those of skill in the art will readily be able to develop or adopt other assays that can provide comparable information.

Once a mutant kinase has been made which accepts a given orthogonal substrate analog, or which is inhibited by a given inhibitor, it can be characterized using classical enzyme kinetic analysis, as illustrated in Examples 5 and 6. Also, as shown in Example 8, one can study the degree to which the mutant can utilize or be inhibited by the analog, and whether the analog is a "dead" (i.e., wholly ineffective) inhibitor for the wild-type enzyme. Of course, the methods used in the examples are not the only ways these studies can be done, and those of skill in the art can easily design alternate approaches.

As illustrated in Example 10, it is not necessary to make multiple amino acid substitutions to provide a mutant that will be inhibited by an inhibitor of the present invention. It may only be necessary to make a single amino acid change, as is the case with the mutants GST-XD4(I338A) and GST-XD4 (I338G).

X. Assay to Identify Kinase Substrates

One embodiment of the present invention is as follows. First, the orthogonal inhibitor is added to two samples of the cell of interest which either express an added gene for the engineered kinase or express the normal copy of the kinase of interest. The inhibitor can be added before after or during the activation of a signaling cascade (such as permeabilized cells, cell extracts, or cells that are naturally permeable to them). Then a method which allows detection of all phosphorylated proteins in a cell or cell fraction, e.g., by using radioactive phosphorous [$\gamma$-$^{32}$P]ATP or by using monoclonal antibodies specific for phosphorylated amino acids is used to reveal the result of specifically inhibition of the kinase of interest. In the cells expressing the normal copy of the kinase of interest, the protein substrates of the native kinase will become labeled, even in the presence of the inhibitor, whereas the protein substrates of the engineered kinase will at least be labeled to a lesser degree; preferably, the protein substrates of the engineered kinase will not be substantially labeled, and most preferably, they will not be labeled at all.

It is also preferable if the wild-type kinase corresponding to the mutant has been removed from the cells, e.g., by "knock-out" of the cellular gene(s) for it. If the labeled proteins of such an assay are examined in tandem with control samples containing the wild-type kinase but not the mutant kinase, certain bands will be diminished in intensity in the mutant-treated sample relative to the control. Preferably, the difference in intensity will be high; most preferably, there will be bands which are missing in the mutant-containing samples treated with the inhibitor. This would indicate that the wild-type form of that kinase phosphorylates those differentially labeled proteins; when the kinase is inhibited, those bands do not get labeled.

Example 10 provides one example of a method of using a mutant kinase of the present invention, along with its orthogonal substrate analog or its inhibitor, as the case may be, to detect which are the intracellular protein substrates for that protein kinase. Developing such a test was primary goal of the research that led to the present invention.

Generally, the method described in Example 10 and in FIG. 8 would appear to be generally applicable; however, there are many other possible approaches that could be used, once a mutant that accepts an orthogonal substrate analog or inhibitor has been prepared. The natural phosphate donor substrate is first prepared to contain a labeled moiety on the terminal phosphate, for example, by replacing the phosphate with [$\gamma$-$^{32}$P] phosphate. This substrate, along with the analog or inhibitor, is then added to a sample of lysed cells, cell extracts, permeabilized cells, or cells which are naturally permeable to the orthogonal nucleotide triphosphate substrate analog or to the inhibitor, and which express the mutant kinase, or to which the mutant kinase has been exogenously added (e.g., by microinjection). After incubation under conditions that will allow the mutant kinase to become inhibited, and/or to phosphorylate its protein substrates to the extent not inhibited, the labeled products are then extracted and analyzed in comparison with those produced by a control sample, which was treated substantially the same way, but without the addition of the analog or inhibitor, respectively. Methods for the detection of labeled proteins are well known, and include both quantitative and qualitative methods. In addition, all methods for characterizing and identifying proteins can be used to determine with specificity what the protein substrates are, and what their functions are. Ultimately, it should be possible to develop an understanding of what protein substrates each of the various protein kinase act upon, and reveal in great detail the mysteries of cellular signal transduction.

Once one or more cellular protein substrate has been identified, similar assays can be used to identify drugs or other compounds that can modulate the activity of a given protein kinase on one or more substrates. For example, one could add small amounts of solutions of a variety of such compounds to test samples containing cell-free extract, mutant kinase, along with a labeled orthogonal substrate analog and/or inhibitor. The labeled proteins can then be identified, e.g., by gel electrophoresis followed by autoradiography, and compared with a duplicate test sample treated the same way, but to which no drug or other compound was added.

If a protein is not labeled in a sample having an added compound plus substrate analog and/or inhibitor that does get labeled in a sample treated with the analog and/or the inhibitor, this indicates that the added compound has caused the kinase to phosphorylate a protein that it does not act on in the absence of the compound, i.e., the compound upwardly modulates the activity of the kinase for that protein. Alternatively, if a labeled protein appears in a test sample to which the compound or drug was added, but does not appear in a test sample not having the compound or drug added, this indicates that the added compound has prevented the kinase from phosphorylating a protein that it does act on in the absence of the compound, i.e., the compound downwardly modulates the activity of the kinase for that protein substrate.

Furthermore, if quantitative measurements are made for each labeled protein, e.g., by scanning autoradiograms and integrating the data, more subtle effect on kinase activity can be detected. For example, it may be found that a protein is more fully or less fully phosphorylated in the presence or absence of a given compound (i.e., has been less dramatically modulated). It can also be expected that some compounds will upwardly modulate kinase activity for some proteins and downwardly modulate activity for others at the same time.

XI. Use in Screening for Drug Design Target Kinase

As mentioned above, because kinase plays key roles in various diseases, it is of great interest to develop inhibitors which can specifically inhibit a single wild-type kinase or group of wild-type kinase. By down-modulating the activity of these disease-involved kinase, it should be possible to reduce the disease symptoms, or even cure the disease. However, the great difficulty which has been experienced in making such inhibitors of wild-type kinase, as briefly described above, limits the potential of that approach. The primary difficulty is finding inhibitors which are specific, and do not inhibit other kinase than the intended target. The reasons for such non-specificity are (i) the nucleotide triphosphate binding sites of kinase are highly conserved in evolution, and (ii) many kinase are "degenerate," that is, they have sufficiently similar activities and specificities that they can substitute for other kinase that because of gene deletion or other reason are absent or diminished in concentration in the cells. The problem of binding site similarities can in many instances be overcome, e.g., by careful rational inhibitor design, or by selection of inhibitors from combinatorial libraries on the basis of specificity. However, efforts to do so with a kinase that is truly degenerate with another kinase will likely be unfruitful, either all of the co-degenerate kinase will be inhibited by even the best candidate compounds, or even if the target is inhibited, it will be impossible to tell, because a degenerate kinase will "take over" the activity of the inhibited one.

Because of this, there is a need for a way to screen kinases to determine which wild-type kinases are degenerate, and thus probably poor candidates for specific inhibition, and which are not degenerate, and therefore preferred candidates for specific inhibition. The present invention provides such a method. The present invention provides a means to generate a specific, unique kinase inhibitor for any kinase of interest, by making a mutant of the kinase that is specifically designed to be inhibited by candidate inhibitors selected, and then studying the effects of that inhibition.

Another, preferred method of such screening would be to produce animal models for the disease of interest, and then "knock out" the wild-type gene, and then, by genetic engineering, insert into the genome a gene encoding a mutant kinase of the present invention "knock-in". Then, an inhibitor of the present invention, preferably one which has been shown in vitro to inhibit the mutant, can be used to down-regulate the mutant kinase. If down regulation leads to a decrease in the symptoms or morbidity of the disease in the model animal, or eliminates the disease, then that kinase is a preferred candidate for the development of a specific inhibitor of the wild-type form.

XII. Gene Therapy Applications

The mutant kinase and inhibitors of the present invention can also be used directly to treat diseases in humans and animals. Just as described above for the animal model systems, gene substitution could be used on patients with diseases which are mediated by those kinase. The wild-type for one or more such wild-type kinase would be deleted, e.g., by "knock-out" methods known in the art, and then specifically inhibitable mutants of those one or more kinase would be added to the animal's genome, e.g.., by "knock-in" or gene therapy methods which are known in the art. Then, the inhibitor could be used as a drug to down-modulate those one or more mutant kinase, such that the disease is ameliorated to at lest some degree, but the degree of activity of those kinase which may be found to be necessary for normal cellular function could be maintained. Of course, the kinase could also be essentially "turned off" by strong inhibition, if that proved to be therapeutically effective. Furthermore, if it is found that the disease is greatly improved or cured by a period of down-regulation or being turned off, then administration of the inhibitor could be discontinued, and the disease well might not return or exacerbate. If not, then inhibition could be discontinued on a long term or even permanent basis, and the mutants could be left to function in the place of the wild-type kinase for the remainder of that patient's life. Since the specific inhibitors of the present invention are not present in the environment, the mutant kinase should behave just like the wild-type (except to the extent that the engineering may have changed their activity or kinetics). And if the disease should recur or flare up again in the future, the patient could again be treated with the inhibitor, without the need to repeat the gene exchange.

XIII. Development of a Molecular Switch for Inhibitor Sensitive Alleles of any Protein Kinase The present invention provides a general approach for sensitizing protein kinases to cell permeable molecules which do not inhibit any wild-type protein kinases. Using a chemical switch to design a unique protein/small molecule interface, protein kinases with unique sensitivity to cell permeable inhibitors were engineered. Seven protein kinases from five distinct families were selected in a semi-random fashion. Inhibitors were identified for every kinase. It is demonstrated that this approach can be successful even for protein kinases which are not potently inhibited by the chosen "lead" inhibitor. It has been shown that divergent scaffolds can be used to generate very different analogs which are specific for the same target. In addition, specific in vivo inhibition of a target kinase without the need to carry out an in vitro screen has been shown. The data suggests that a majority of protein kinases will be susceptible to this target specific inhibition strategy. For organisms that readily undergo homologous recombination (such as *Saccharomyces cerevisiae, Dictyostelium discoideum*, DT40 chicken B cells, and embryonic stem cells) this approach opens up the possibility of rapidly generating conditional allelic strains for every protein kinase in the genome, even those without visible null phenotypes. A library of such strains would represent a significant step forward in realizing the pharmacogenomic vision of identifying small molecule ligands for every gene product in the cell.

XIV. Cdc28 Mutant Kinase Sensitive to Cell-Permeable Chemical Inhibitor

The cyclin-dependent protein kinases (Cdks) drive and coordinate the events of the eukaryotic cell division cycle (112). In the budding yeast *Saccharomyces cerevisiae*, the cell cycle is regulated by Cdc28(Cdk1) (reviewed in (113)), whose function has been studied primarily by the analysis of temperature-sensitive (ts) mutant alleles (114). At 37° C., most of these mutants arrest in G1, suggesting that progression through START is uniquely sensitive to inhibition of Cdc28 activity. Interestingly, analysis of ts mutants has not provided clear evidence that Cdc28 plays a role in the G2/M transition, despite abundant evidence that Cdk1 is required for mitotic entry in other eukaryotes (115–117).

Temperature-sensitive mutants are powerful tools in the analysis of gene function, but analysis of ts phenotypes can sometimes be complicated by the effects of heat shock. In addition, the mechanism of ts protein inactivation is rarely understood in molecular detail. For example, the kinase activity of Cdc28 is decreased in certain cdc28 ts mutants at high temperature (118), but it is not clear if the cell cycle arrest is due to an effect on the catalytic function of the enzyme or due to defects in protein folding, stability, or interactions with other proteins.

Chemical genetics provides an alternative approach to the generation of conditional defects in gene function (119–121). In this approach, the function of a previously identified gene product is determined through the use of a highly specific chemical inhibitor identified by rational design or screening of chemical libraries. Unfortunately, this approach has had only limited success in the study of protein kinases, whose highly conserved active sites make it difficult to identify mutant specific inhibitors (121, 122).

A highly specific chemical genetic approach that involves the design of a mutated target kinase that is uniquely sensitive to a cell-permeable chemical inhibitor was developed (123–125). Based on mutation of the corresponding residue in the Src family of kinases (126), phenylalanine 88 in Cdc28 was replaced with a glycine, resulting in the formation of a new pocket in the ATP-binding site. This mutant kinase, Cdc28-as1 (analog-specific 1), was predicted to be sensitive to 4-amino-1-(tert-butyl)-3-(1'-naphthylmethyl)pyrazolo[3,4-d]pyrimidine (1-NM-PP1), an analog of the kinase inhibitor PP1 that carries a modification that should occupy the engineered pocket in the ATP binding site.

This invention demonstrates that an allele-specific chemical inhibitor can be used to study Cdc28 activity in vivo. At low concentrations of 1-NM-PP1, cdc28-as1 strains delay or arrest in G2/M with hyperpolarized buds. This phenotype is similar to that observed in cells lacking the mitotic cyclins Clb1-4 (139). The phenotype in cdc28-as1 cells is due to a reduction in Cdc28 activity below some threshold required for mitotic entry and for the switch from apical to isotropic bud growth. Apparently, the activity of G1/S cyclin-Cdk complexes in these cells is still sufficient to trigger budding and DNA replication. Only at higher concentrations of inhibitor is the activity of these complexes reduced below the threshold required for passage through START. These data are generally consistent with the notion that different cell cycle events are triggered by specific threshold levels of CDK activity, and that later events require higher amounts of activity (140). However, the differences in the substrate specificity of different cyclins also contribute to the ordering of cell cycle events (141–143).

The evidence that G2/M progression is most sensitive to Cdc28 inhibition seems to contradict previous results with temperature-sensitive cdc28 mutants, most of which arrest as unbudded cells in G1. Perhaps the G1 arrest at high temperature is explained by differences in the temperature sensitivity of different forms of Cdc28. For example, a G1 arrest might result if Cdc28-Clb complexes in S phase or G2/M are more heat-resistant than the monomeric Cdc28 that predominates in G1. The use of allele-specific chemical inhibition provides a powerful alternative method that avoids these and other problems with temperature-sensitive mutants.

The structure of the ATP binding site is highly conserved among protein kinases, and therefore our approach should be applicable to the analysis of any protein kinase (thus far, we have successfully identified specific inhibitors of engineered Src, Fyn, Cdk2, CaMKIIα, c-Abl, Fus3, Lck, p38, and Pho85 (123–125, 144). This method also provides an approach to the generation of conditional alleles that is more rapid than traditional methods for the isolation of temperature sensitive alleles. In addition, the availability of a new class of conditional alleles will allow straightforward epistasis analysis to order gene products in linear signaling pathways: reciprocal shift experiments between an analog-specific allele and any other temperature-sensitive or cold sensitive gene product of interest can now be performed. The results also suggest that the strength of the mutant allele can be controlled by varying the concentration of inhibitor: thus, cdc28-as1 behaves as a weak allele at moderate inhibitor concentrations and a virtual null allele at high concentrations. The application of this method to other protein kinases should therefore allow the identification of gene functions with different requirements for catalytic activity. Similarly, in cases where a protein kinase is thought to have both kinase-dependent and -independent functions (145), the use of an analog-specific allele would inhibit only those functions that require kinase activity. Finally, the same kinase mutation that generates the analog-specific allele also allows the kinase to use radiolabeled ATP analogs that are modified to complement the engineered ATP binding site (126, 146). Addition of these ATP analogs and the mutant kinase to cell lysates should lead to the labeling and identification of direct kinase targets. This approach can also be used to identify specific Cdc28 substrates.

XV. Cell Lines

As explained elsewhere herein, engineered expression vectors containing the nucleic acid encoding the mutant enzyme may be used to transform an appropriate host cell. A number of mammalian cell lines are known in the art and include immortalized cell lines available from the American Type Culture Collection (ATCC), such as, but not limited to, Chinese hamster ovary (CHO) cells, HeLa cells, baby hamster kidney (BHK) cells, monkey kidney cells (COS), human hepatocellular carcinoma cells (e.g., Hep G2), Madin-Darby bovine kidney ("MDBK") cells NIH/3T3, 293 cells (ATCC #CRL 1573), COS-7, 293, BHK, CHO, TM4, CV1, VERO-76, HELA, MDCK, BRL 3A, W138, Hep G2, MMT 060562, TRI cells, as well as others. A well known example of an avian cell line is the chicken B cell line "DT-40". Examples of vectors useful for transforming such cell lines include, but are not limited to, retroviral vectors, vaccinia virus vectors, adenovirus vectors, herpes virus vector, fowl pox virus vector, bacterial expression vectors, plasmids, such as pcDNA3 (Invitrogen, San Diego, Calif.) or the baculovirus transfer vectors.

Insect cells for use with baculovirus expression vectors include, inter alia, *Aedes aegypti, Autographa californica, Bombyx mori, Drosophila melanogaster, Spodoptera frugiperda,* and *Trichoplusia ni.*

In another embodiment, genes of the invention are cloned downstream of a *C. elegans* constitutive or inducible promoter, such as the heat-shock promoter element in an expression vector such as pPD69.78 hsp 16.2 or pPD69.3 hsp 16–41, which are public domain vectors for creating *C. elegans* transgenic lines in which the gene of interest is under the control of an inducible heat shock promoter element. Transgenic *C. elegans* may then be obtained by microinjection of oocytes.

In another embodiment, Drosophila cells may be transfected with commonly available vectors (156, 157).

Streptococcus spp. and other lower eukaryotic cells will find use with the present expression constructs. Yeast hosts useful in the present invention include inter alia, *Saccharomyces cerevisiae, Candida albicans, Candida maltosa, Hansenula polymorpha, Kluyveromyces fragilis, Kluyveromyces lactis, Pichia guillerimondii, Pichia pastoris, Schizosaccharomyces pombe* and *Yarrowia lipolytica.*

The following examples are provided to describe and illustrate the present invention. As such, they should not be construed to limit the scope of the invention. Those in the art will well appreciate that many other embodiments also fall within the scope of the invention, as it is described hereinabove and in the claims.

EXPERIMENTAL DETAILS SECTION

Example 1

Synthesis of ATP analogs: Twelve different orthogonal ATP analogs were synthesized. FIG. 2 is a schematic representation of their structure. The Figure shows adenosine triphosphate (ATP), with an "X" bound to the 6 position; and in the box below, schematic representations are provided for the twelve side chains that take the place of "X" in each of the orthogonal ATP analogs described in the examples (which are always referred to by the numbers 1–12). Those analogs are:

1  $N^6$(methoxy)ATP
2  $N^6$(ethoxy)ATP
3  $N^6$(acetyl)ATP
4  $N^6$(i-propoxy)ATP
5  $N^6$-(benzyl)ATP
6  $N^6$-(benzyloxy)ATP
7  $N^6$-(pyrolidino)ATP
8  $N^6$(cyclopentyl)ATP
9  $N^6$(cyclopentyloxy)ATP
10 $N^6$-(pipperidino)ATP
11 $N^6$-(cyclohexyl)ATP
12 $N^6$-(cyclohexyloxy)ATP Analogs 1, 2, 4, 6, 9, and 12 were synthesized via Dimroth rearrangement of the corresponding $\underline{N}^1$ alkoxy adenine derivatives in four steps starting from adenosine, according to the procedure of Fujii et al (43). Analog 5 was synthesized similarly via Dimroth rearrangement of $\underline{N}^1$ benzyladenosine (44). Analog 3 was prepared via in situ protection of the adenosine hydroxyl groups as trimethylsilyl ethers and subsequent treatment with acetyl chloride, according to McLaughlin et. al. (45). Analogs 7, 8, 10 & 11 were synthesized via treatment of 6-chloropurine riboside (Aldrich) with pyrrolidine, cyclopentylamine, piperidine & cyclohexylamine, respectively (46).

Triphosphate synthesis was carried out according to the method of Ludwig (47) with the exception of the preparation of pyrophosphate. Accordingly, bis-tri-N-butyl ammonium pyrophosphate was prepared by mixing 1 equivalent of pyrophosphoric acid with 2 equivalents of tributylamine in a (1:1) water: ethanol mixture until a homogenous solution was obtained. Solvent was removed under vacuum to dryness and the pyrophosphate was stored over $P_2O_5$ overnight. All non-radioactive nucleotides ere characterized by $^1$H-NMR, mass spectral analysis and strong anion exchange (SAX) HPLC (Rainin #83-EO3-ETI).

[γ-$^{32}$P] $\underline{N}^6$-(cyclopentyl)ATP was synthesized according the method of Hecht and Kozarich (48). The radiolabeled analog was purified by DEAE (A-25) Sephadex (Pharmacia) column chromatography and the triphosphate was identified by co-injection of the radiolabeled material with an authentic sample of $\underline{N}^6$-(cyclopentyl) ATP on an SAX-anion exchange HPLC column (Rainin) (linear gradient of 5–750 mM ammonium phosphate pH 3.9 in 10 min. At 0.5 mL/min). The chemical yield of the reaction varied from 70% to 80%.

Example 2

Screening of Nucleotide Analogs: To identify compounds that would not be accepted as substrates by any existing cellular kinase (53), a panel of synthetic A*TP analogs were screened in a murine lymphocyte lysate (CF) rich in protein tyrosine kinase (13). The assays were performed using spleenocytes (8–30 week old male and female C57/B6 mice from the Princeton University Animal Facility) which were isolated and washed in RPMI-1640 medium containing 5% Bovine Calf Serum (BCS), 1% Hepes and DNAseI (1 ug/ml). Red cells were lysed at 4° C. by treatment with 17 mM tris ammonium chloride pH 7.2. The cells were hypotonically lysed on ice for 10 min. In 1 nM Hepes pH 7.4, 5 mM $MgCl_2$, leupeptin (10 ug/ml), aprotinin (10 ug/ml) and 100 uM PMSF according to the method of Fukazawa et. al. (51). After vortexing and centrifugation at 500×g, the supernatant was collected. Cells were stored at 4° C. for 20 min.

To attenuate the basal protein phosphorylation level, after which the buffer was adjusted to 20 mM Hepes pH 7.4, 10 mM MgCl$_2$ and 1 mM NaF. Sodium vanadate (100 uM) was then added to inhibit the activity of phosphotyrosine phosphatases.

Each nucleotide triphosphate was added to a final concentration of 100 uM to 5×10$^6$ cell equivalents and incubated at 37° C. for 5 min. after which 4×Laemmli gel loading buffer was added to the cell lysate to quench the reaction. Proteins were separated by 12.5% SDS-PAGE and transferred to Protran BA85 (Schleicher-Schuell). The blot was probed with the anti-phosphotyrosine monoclonal antibody 4G10 (Upstate Biotechnology) and the bound antibody was detected via enhanced chemiluminescence (cat. 34080, Pierce) following treatment with HRP-coupled goat-anti-mouse antibody (VWR cat. 7101332) according to the manufacturer's instructions.

The results are shown in FIG. 3, which is an anti-phosphotyrosine protein immunoblot showing the level of protein tyrosine phosphorylation following treatment of a chains within a 4 Å sphere of the N$^6$ amino group of bound ATP: V104/M120 (PKA) and V64/F80 (CDK2) (60).

FIG. 4 shows a close-up view of the ATP binding site in cAMP dependent protein kinase (PKA), which is bound to ATP. Three residues within a 4 Å sphere of the N$^6$ amine of ATP (Val104, Met102, and Glu121) and the catalytically essential lysine residue (Lys72) are shown in ball-and-stick representation. The remainder of the protein is shown in ribbon format. This figure was created by feeding the output of Molscript into the Raster3D rendering program (68,69). Note that in the model, the side chain of Glu121 is pointed away from the adenine ring binding region, and therefore Glu121 was not a candidate for alteration.

The sequence alignment of the ATP binding regions of PKA (SEQ ID NO: 1), CDK2 (SEQ ID NO: 2), and v-Src (SEQ ID NO: 3) are shown below. The residues shown in bold correspond to the amino acids with side chains in a 5 Å sphere of the N$^6$ amino group of kinase bound ATP.

```
Subdomain              IV                       V
PKA (SEQ ID NO: 1)     (99)  NFPFLVKLEFSFKDNSNLYMVMEYVPG    (125)
CDK2 (SEQ ID NO: 2)    (59)  NHPNIVKLLDVIHTENKLYLVFEFLHQ    (85)
v-Src (SEQ ID NO: 3)   (318) RHEKLVQLYAVVSE-EPIYIVIEYMSK    (343)
``` murine lymphocyte cell lysate (CF) with 100 uM of ATP or A*TPs (1–12). The cell lysate used includes the protein tyrosine kinase Src, Fyn. Lck, Lyn, Yes, Fgr, Hck, Zap, Syk, Btk, Blk, and other protein tyrosine kinase present in B and T lymphocytes, macrophages, and follicular dendritic cells (13). Molecular size standards (in kilodaltons) are indicated. The A*TPs containing the smallest N$^6$ substituents, 1 (methoxy), 2 (ethoxy), and 3 (acetyl) showed some ability to serve as cellular protein tyrosine kinase substrates (FIG. 3, lanes 3–5). The A*TPs with sterically demanding N$^6$ substituents, 4 (I-propoxy), 5 (benzyl), and 6 (benzyloxy), and all analogs containing cyclic aliphatic substituents (7–12) showed little or no protein phosphorylation (FIG. 3, lanes 6–8, 11–16).

To test for possible metathesis of orthogonal A*TPs (7–12) with cellular ADP to give A*DP and ATP, 1 mM ADP was added to cell lysate kinase reactions identical to those shown in FIG. 3; the pattern of phosphoproteins was the same, indicating that no significant metathesis of A*TP occurs in a complete cell lysate system.

Based upon these results, it appears that analogs (7–12) are "dead substrates" for wild-type protein tyrosine kinase, i.e., the wild-type substrates do not substantially, or at all, accept these as phosphate donor substrate. These analogs thus were chosen as the most preferred targets for reengineering the nucleotide binding site of v-Src.

Example 3

Designing the Mutant v-Src: No crystal structures of any protein tyrosine kinase in an active conformation have been solved to date although several structures of inactive kinase have been solved (54,55). However, two crystal structures of catalytically active ser/thr kinase have been solved (56,57). There is a high degree of functional homology between the ser/thr and the protein tyrosine kinase catalytic domains as shown by affinity labeling of the identical catalytically active lysine residue in both kinase families (K72 in cAMP dependent kinase (PKA), K295 in v-Src) (58,58). Inspection of the PKA (56) and cyclin dependent kinase-2 (CDK2)-cyclinA (57) crystal structures revealed two amino acid side Based on the functional similarity between the above-described kinase, positions V323 and I338 in the v-Src catalytic domain were mutated, which correspond to V104/M120 in PKA & V64/F80 in CDK2. By mutating these residues to alanine, it was hoped to create an additional "pocket" in the nucleotide binding site of v-Src to allow binding of one of the preferred orthogonal A*TPs (4–12).

Example 4

Mutant Synthesis, Expression and Purification: The mutant (V323A, I338A) was made as described below. Both the wild-type and the double alanine mutant of the v-Src catalytic domain, (the XD4 fragment) were made as glutathione S-transferase (GST) fusion proteins (GST-XD4) (61,62). These were made in *E. coli*, which is a good expression host because it lacks any endogenous protein tyrosine kinase, as described in the following Example. The XD4 fragment of v-Src was used because it contains an intact SH1 catalytic domain but lacks the non-catalytic regulatory SH3 and SH2 domains, and exhibits higher specific activity than full-length v-Src.

Overlap extension PCR was used to make GST-XD4 (V323A, I338A) (49). Pfu polymerase (Stratagene) was used in the PCR reactions according to the manufacturer's protocol. Six synthetic oligonucleotides were used:
SEQ ID NO: 4 (5'-TTTGGATCCATGGGGAGTAGCAAGAGCAAG),
SEQ ID NO: 5 (5'-TTTGAATTCCTACTCAGCGACCTCCAACAC).
SEQ ID NO: 6 (5'-TGAGAAGCTGGCTCAACTGTACGCAG).
SEQ ID NO: 7 (5'-CTGCGTACAGTTGAGCCAGCTTCTCA).
SEQ ID NO: 8 (5'-CTACATCGTCGCTGAGTACATGAG).
SEQ ID NO: 9 (5'-CTCATGTACTCAGCGACGATGTAG).
Primer SEQ ID No: 4 contains a BamHl site and primer (SEQ ID NO: 5) contains and EcoR1 site (shown in italics). Primers (SEQ ID NO: 6) and (SEQ ID NO: 7) contain the nucleotide sequence changes to introduce the V323A mutation (nucleotides encoding mutations are shown in bold).

Primers (SEQ ID NO: 8) and (SEQ ID NO: 9) contain the I338A mismatch.

The XD4 gene from Yep51-XD4 plasmid (a gift of B. Cochran at Tufts Medical School) was amplified with primers (SEQ ID NO: 4) and (SEQ ID NO: 5). The PCR product was digested with BamH1 and EcoR1 and ligated into BamH1 and EcoR1-digested pGEX-KT and then transformed into the E. coli strain DH5α.

The GST-XD4 (V323A) was constructed using primer SEQ ID NO: 4, SEQ ID NO: 5, SEQ ID NO: 6 and SEQ ID NO: 7 with the GST-XD4 plasmid as the template. The PCR product from the two step procedure was digested with BamH1 and EcoR1, ligated into BamH1 and EcoR1-digested pGEX-KT, and transformed into DH5α E. coli cells. GST-XD4 (V323A, I338A) was made in the same manner using primers SEQ ID NO: 8 & SEQ. ID NO. 9 with GST-XD4 (V323A) as the template.

Expression and purification of the GST fusion kinases were carried out in E. coli strain DH5α as described by Xu et al (50), with the exception that the cells were stored at 4° C. overnight prior to centrifugation and lysis by French press (overnight storage is essential for producing highly active kinases).

Expression of 6-His-XD4 and 6-His-XD4 (V323A, I338A) in Sf9 insect cells was accomplished using the Life Technologies BAC-to-BAC system. Briefly, the 6-His-XD4 and 6-His-XD4 (V323A, I338A) genes were generated by PCR using the corresponding pGEX vectors as templates with primers SEQ ID NO: 4 and SEQ ID NO: 5, followed by digestion with BamH1 and EcoR1. The resulting PCR fragment was cloned into pFASTBAC which had been digested with BamH1 and EcoR1. Transformation of HB10BAC cells and subsequent transfection of Sf9 cells with the Bacmid containing XD4 or XD4 (V323A, I338A) were carried out as suggested by the manufacturer.

In an alternate procedure preformed herein, transfection of v-src or v-src (I338G) mutant kinase was performed by cloning the v-src gene from the pGEX-v-Src vector(4) into the Pbabe vector(5) which contains the 1tr promoter for high level of expression in NIH 3T3 cells. The pBabe v-Src (I338G) plasmid was transfected into viral packaging cell line. BOSC 23(6) and viral particles harvested after 2 days as described(6). NIH 3T3 cells were infected as described (7) with these viral particles and stable transfectants were selected in puromycin containing media as described (5). Stable transfectants were maintained in media containing puromycin to ensure no loss of expression of v-Src.

Figure 1:
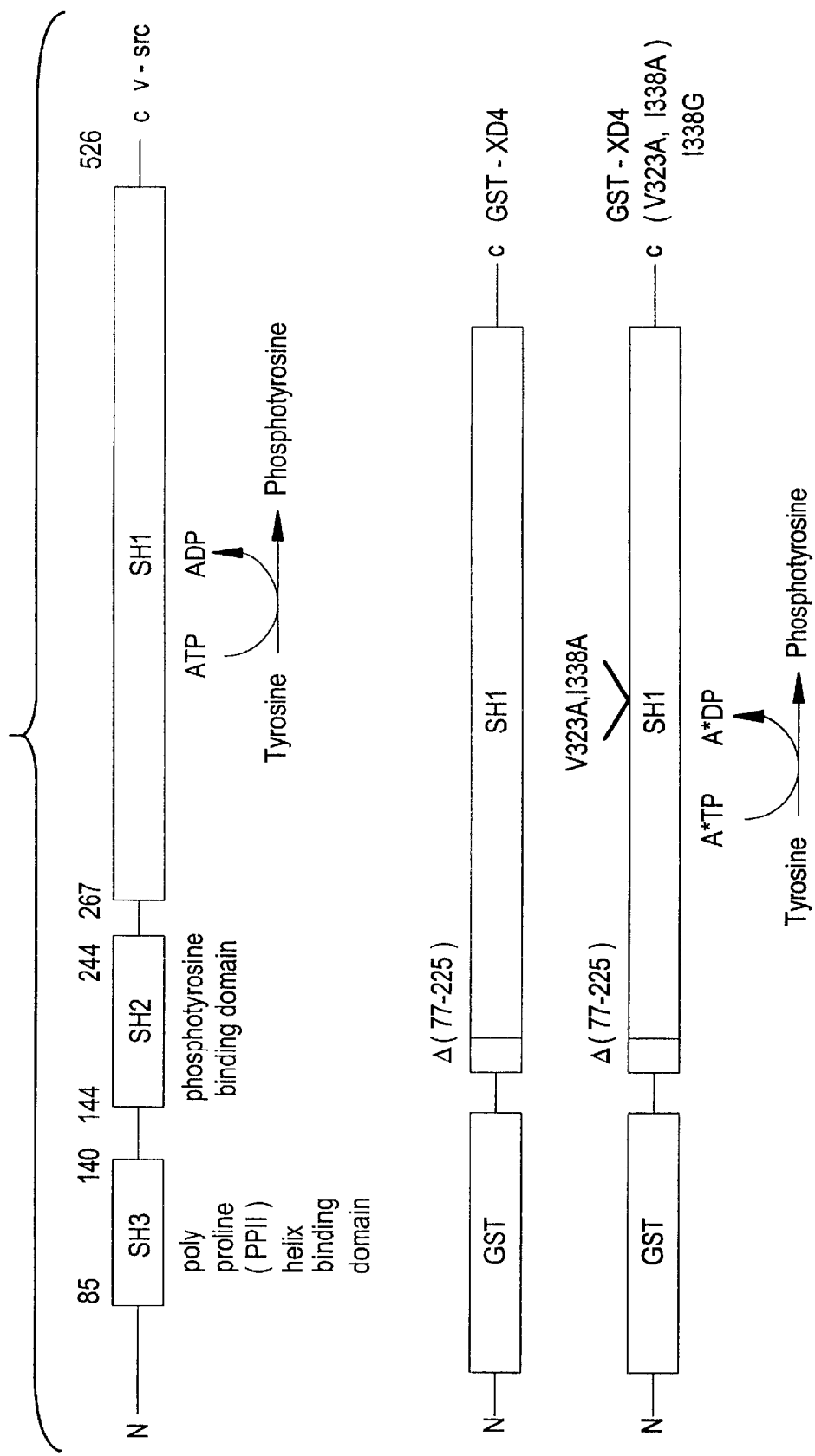
FIG. 1 is a schematic representation of the protein domain structures of v-Src, of XD4 (which has a deletion of residues 77–225), of the glutathione S-transferase (GST)-XD4 fusion protein, and of the GST-XD4 fusion protein double mutant (V323A, I338A).

The final results are shown in FIG. 1, which is a diagram showing the domain structure of v-Src including the Src-homology 3,2, and 1 (SH3, SH2 & SH1) domains, with the domain boundaries indicated by the amino acid residue numbers listed above each boxed domain. The domain structure of XD4 is also represented, which contains a deletion of residues 77–225 (Δ77–225). Domain organizations of the glutathione S-transferase (GST) fusion with XD4 (numbering from v-Src), and the doubly mutated GST-XD4 (representing both V323A, I338A and I338G) are also shown schematically.

Example 5

Testing the Mutant v-Src For Ability to Bind Orthogonal ATP Analogs: The ability of the $\underline{N}^6$ substituted ATP analogs (1–12, FIG. 2) to differentially inhibit wild-type and mutant kinase phosphorylation of RR-Src with [γ-$^{32}$P] ATP, which is a measure of their ability to bind to the respective ATP binding sites was evaluated. Assays were carried out in triplicate at 37° C. in a final volume of 30 μL buffered at pH 8.0 containing 50 mM Tris, 10 mM $MgCl_2$, 1.6 mM glutathione, 1 mg/ml BSA, 1 mM RR-Src peptide with either GST-XD4 (100 nM) or GST-XD4(V323A, I338A) (100 nM) and 10 μM [γ-$^{32}$P] ATP (1000 cpm/pmol) [Dupont NEN]. Cold ATP or ATP analogs (100 μM) (1–12) were added prior to addition of the kinase. After 30 minutes the reactions were quenched by spotting 25 μL of the reaction volume onto p81 phosphocellulose disks (Whattman) and these were immersed in 250 mL of 10% acetic acid for >30 minutes followed by washing and scintillation counting according to standard methods (52).

The results are shown in FIG. 6. Relative inhibition of GST-XD4 is shown by solid bars, and relative inhibition by GST-XD4(V323A, I338A) is represented by the diagonal filled bars. Percent inhibition $(1-v_I/v_0)$ is reported as a ratio of $v_I$ (cpm in the presence of 100 μM of the indicated triphosphate and 10 μM [γ-$^{32}$P] ATP (1000 cpm/pmol)/$v_0$ (cpm in the presence of 10 μM [γ-$^{32}$P] ATP (1000 cpm/pmol) alone—background cpm due to non-specific 10 μM [γ-$^{32}$P] ATP binding to the phosphocellulose disks (<0.1% of total input counts)). Error bars represent the S.D. determined from four separate experiments with three replicates.

The wild-type kinase GST-XD4 displays poor binding affinity for most ATP analogs (FIG. 6, solid bars) as expected from the lymphocyte kinase assay (FIG. 3). In contrast, the doubly mutated GST-XD4(V323A, I338A) shows excellent inhibition by more sterically demanding $\underline{N}^6$ substituted ATP analogs (FIG. 6, shaded bars). Most significantly, the GST-XD4(V323A, I338A) mutant is inhibited from phosphorylating RR-Src with [γ-$^{32}$P]-ATP by ATP analogs 5, 8, 9, and 11 almost as well as the wild-type kinase, GST-XD4, is inhibited from phosphorylating RR-Src with [γ-$^{32}$P]-ATP by its natural substrate ATP. It was confirmed that GST-XD4 (V323A, I338A) and the full length GST-v-Src(V323A, I338A) display the same inhibition pattern with ATPs (1–12).

Four of the nine "dead" substrates identified in the screen of wild-type kinase specificity (FIG. 3) bind well to the mutant kinase. This high success rate in identifying new substrates for a mutant v-Src which are not accepted by wild-type kinase suggests that a key feature of the v-Src nucleotide binding site was identified, namely the residues which make a close fit around the $\underline{N}^6$ amino group of ATP. It is worth noting that no wild-type protein kinase is known which contain an alanine at the position corresponding to I338 in v-Src (position 120 in PKA). If a sterically demanding amino acid side chain at this position also plays a critical role in determining the specificity of other kinase, it should well be possible to engineer them to accept orthogonal substrates using an approach very similar to the one described here, and such engineered kinase would be well within the scope of the present invention.

Example 6

Determining Catalytic Efficiency of Mutant v-Src with the Most Preferred Orthogonal ATP Analog: The ability of $\underline{N}^6$-(cyclopentyl) ATP, 8, to serve as a catalytically competent substrate of both wild-type GST-XD4 and the GST-XD4 (V323A, I338A) mutant over the other three ATP analogs 5, 9, and 11 because analog 8 exhibited a slightly lower level of phosphorylation with wild-type kinase was tested (FIG. 3, lane 12).

ATP and $\underline{N}^6$-(cyclopentyl) ATP dependent RR-Src phosphorylation (1 mM) by GST-XD4 (V323A, I338A) and GST-XD4 were carried out at low substrate conversion (<5%) in triplicate. Kinetic constants were determined by analysis of Lineweaver-Burk plots of the rate data (64). Assays were carried out in triplicate at 37° C. in a final volume of 30 µL buffered at pH 8.0 containing 50 mM Tris, 10 mM MgCl$_2$, 1.6 mM glutathione, 1 mg/mL BSA, 1 mM RR-Src peptide with either GST-XD4 (100 nM) or GST-XD4(V323A, I338A) (100 nM) and 10 µM.

[γ-$^{32}$P] ATP (1000 cpm/pmol) or [γ-$^{32}$P] N$^6$-(cyclopentyl) ATP (5000 cpm/pmol) as indicated.

TABLE 1

Kinetics for Phosphate Donor Substrates

| | GST-XD4 | | | GST-XD4(V323A, I338A) | | |
|---|---|---|---|---|---|---|
| Nucleotide | $k_{cat}$ (min$^{-1}$) | $K_M$ (µM) | $k_{cat}/K_M$ (min$^{-1}$ M$^{-1}$) | $k_{cat}$ (min$^{-1}$) | $K_M$ (µM) | $k_{cat}/K_M$ (min$^{-1}$ M$^{-1}$) |
| ATP | 2 ± 0.5 | 12 ± 3 | 1.6 × 10$^5$ | 0.8 ± 0.2 | 150 ± 20 | 5.3 × 10$^3$ |
| N$^6$-(cyclopentyl)-ATP | | 2000(K$_I$) | (5 ± 2-) × 10$^2$ | | 15 ± 3 | 3.3 × 10$^3$ |

As shown in Table 1 above, the wild-type kinase GST-XD4 did not substantially phosphorylate the RR-Src peptide with [γ-$^{32}$P] N$^6$-(cyclopentyl)ATP, confirming the previous observations that this analog is not a significant substrate for the wild-type kinase. In contrast, GST-XD4(V323A, I338A) displayed Michaelis-Menten kinetics with the orthogonal ATP, [γ-$^{32}$P] N$^6$-(cyclopentyl)ATP. The $K_M$ of the mutant for the orthogonal substrate is quite close to the $K_M$ of GST-XD4 for ATP. On the other hand, the mutant has a $K_M$ for ATP which is more than 10-fold higher than the $K_M$ of GST-XD4 for ATP.

The parameter used to rank catalysts for competing substrates is the ratio of the turnover number to the Michaelis-Menten constant, $k_{cat}/K_M$ (the "specificity constant") (64). The $k_{cat}/K_M$ of the engineered mutant GST-XD4(V323A, I338A) with the orthogonal substrate [γ-$^{32}$P] N$^6$-(cyclopentyl)ATP is only 50-fold lower than the $k_{cat}/K_M$ value of the wild-type kinase with its natural substrate, ATP. This catalytic efficiency with the orthogonal ATP substrate, coupled with the mutant kinase's lower catalytic efficiency with ATP when compared to the wild-type, satisfy two of the design criteria discussed above.

It is even more significant that the new substrate, [γ-$^{32}$P] N$^6$-(cyclopentyl)ATP, is not substantially utilized by wild-type GST-XD4, as demonstrated by the apparent complete inability of GST-XD4 to use this analog as a phosphodonor for autophosphorylation; this is illustrated in FIG. 5C, lane 3. FIG. 5C is an autoradiogram showing [γ-$^{32}$P] ATP dependent autophosphorylation of GST-XD4, lane 1, or GST-XD4 (V323A, I338A), lane 2; and [γ-$^{32}$P] N$^6$-(cyclopentyl)ATP dependent phosphorylation of GST-XD4, lane 3, or GST-XD4(V323A, I338A) phosphorylation, lane 4. Note that in contrast to GST-XD4, the engineered kinase is efficiently autophosphorylated with [γ-$^{32}$P] N$^6$-(cyclopentyl)ATP (FIG. 5C, lane 4).

Example 7

Confirming Retention of Protein Substrate Specificity: As shown in Table 2 below, it was discovered that the wild-type GST-XD4 kinase phosphorylated to a well characterized peptide substrate of v-Src, RR-Src, with kinetics consistent with literature reports (63). This indicates that the sequence engineering had not substantially affected the catalytic activity of the enzyme with respect to its protein substrates.

TABLE 2

Kinetics for Protein Substrate RR-Src

| Nucleotide (Saturated) | GST-XD4 $K_M$ (mM) | GST-XD4(V323A, I338A) $K_M$ (mM) |
|---|---|---|
| ATP | 2.6 ± 0.9 | 3.1 ± 0.9 |
| N$^6$-(cyclopentyl)ATP | — | 2.1 ± 0.9 |

Assays of GST-XD4 and GST-XD4(V323A, I338A) phosphorylation of RR-Src were carried out in triplicate at 37° C. in a final volume of 30 µL buffered at pH 8.0 containing 50 mM Tris, 10 mM MgCl$_2$, 1.6 mM glutathione, 1 mg/ml BSA, 1 mM RR-Src peptide with either GST-XD4 (100 nM) or GST-XD4(V323A, I338A) (100 nM) and 10 µM [γ-$^{32}$P] ATP (1000 cpm/pmol) [Dupont NEN].

To determine whether the alanine mutations have any effect on the protein substrate specificity, the $K_M$ of both the wild-type and the mutant fusion proteins for the RR-Src peptide was measured. At saturating concentrations of [γ-$^{32}$P] ATP the wild-type and the mutant display essentially the same $K_M$ for RR-Src, 2.6±0.9 mM, respectively (63). In addition, the K of the mutant for the protein substrate in the presence of saturating amounts of the orthogonal substrate was also essentially the same, 2.1±0.9 mM. These findings suggest that the alanine mutations in the ATP binding pocket, which is proximal to the adjacent phospho-acceptor binding site, do not affect the protein target specificity.

In support of this, the engineered kinase phosphorylates the same broad set of proteins that are phosphorylated by wild-type XD4 when each is expressed in Sf9 insect cells. This is shown in the FIG. 5(a), which shows an anti-phosphotyrosine protein blot of cell lysates (10$^8$ cell equivalents/land) from Sf9 insect cells expressing 6-His-XD4, lane 2, or 6-His-XD4 (V323A, I338A) lane 3. These blots were carried out following lysis of 10$^6$ cells in a buffer containing 0.1% Triton-X-100, 50 mM Tris, pH 8.0, using a procedure similar to that of the blots of Example 2.

The Sf9 insect cell system is a good host for expressing small amounts of protein tyrosine kinase because these cells contain most of the same machinery necessary to carry out post-translational modifications to proteins resulting in kinase which are more similar in activity to those found in mammalian cells. Furthermore, uninfected Sf9 cells lack endogenous protein tyrosine kinase activity, as shown in FIG. 5A, lane 1, and thus the phosphotyrosine containing proteins in lanes 2 and 3 of FIG. 5A are substrates of the expressed 6-His-XD4 or mutant 6-His-XD4 kinase. The small differences in phosphorylation level of particular proteins is attributed to the lower catalytic activity of the mutant XD4 (V323A, I338A) compared to the wild-type kinase. Taken together, these data show that the peptide specificity of the engineered kinase is virtually identical to that of wild-type v-Src.

Example 8

Confirmation that the Engineered Kinase Accepts the Preferred Orthogonal Substrate, but the Wild-Type Kinase Does Not Substantially Accept It: The ultimate goal of this work is to use mutant kinase specific for synthetic substrate analogs to tag the direct protein substrates in whole cells or cell lysates. For this it is preferable that no wild-type kinase, including ser/thr specific kinase (which carry out the bulk of cellular phosphorylation, as only 0.03% of all phospho-amino acids are tyrosine) (65), substantially accept the synthetic substrate. To establish that [γ-$^{32}$P] $\underline{N}^6$-(cyclopentyl)ATP is essentially a "dead substrate" for all wild-type cellular kinase, in vitro kinase reactions with [γ-$^{32}$P] ATP or [γ-$^{32}$P] $\underline{N}^6$-(cyclopentyl)ATP were performed with murine lymphocyte lysates.

These assays were performed in a manner similar to the procedure set forth in Example 2, with the exception of the use of radiolabeled [γ-$^{32}$P] ATP or [γ-$^{32}$P] $\underline{N}^6$-(cyclopentyl) ATP (5000 cpm /pmole) added to a final concentration of 100 μM with 5×10$^6$ cell equivalents and incubated at 37° C. for 10 min., after which 4×Laemmli gel loading buffer was added to the cell lysate to quench the reaction. Proteins were separated by 12.5% SDS-PAGE. The gel was soaked in 10% acetic acid, 10% isopropanol for 1 h. after which it was dried in a gel dryer and exposed to Biomax MS film (Kodak #111–1681) for 1 h.

The results are shown in FIG. 5(b), which is an autoradiogram showing the level of phosphorylation in hypotonically lysed murine lymphocytes with [γ-$^{32}$P] ATP, lane 1 or [γ-$^{32}$P] $\underline{N}^6$-(cyclopentyl)ATP, lane 2. There are no radiolabeled phosphoproteins in the cell lysate following addition of [γ-$^{32}$P] $\underline{N}^6$-(cyclopentyl)ATP, confirming the true orthogonal nature of $\underline{N}^6$-(cyclopentyl)ATP with respect to all wild type protein kinase. The same result was found when in vitro kinase reactions with [γ-$^{32}$P] ATP or [γ-$^{32}$P] $\underline{N}^6$-(cyclopentyl)ATP and NIH 3T3 cell lysates were used instead of freshly isolated murine lymphocytes. In principle, the ability to follow one protein kinase's activity in the presence of all other cellular kinase would allow for the identification of the direct kinase targets in a particular cell type by using membrane permeabilization (66) and a cell permeable form of A*TP to introduce [γ-$^{32}$P] A*TP into cells (67).

Example 9

Construction and Analysis of Single Mutation v-Src Mutants: In order to determine whether a single mutation might be sufficient to allow $\underline{N}^6$ (cyclopentyl)ATP to be efficiently used as a substrate, three additional v-Src derived mutants were prepared, using methods comparable to those of Example 4. However, these had only single mutations, at position 338. These were again expressed as GST-XD fusion proteins. These mutants, GIST-XD(I338A), GST-XD (I338G), were then tested as described in Example 8.

The results are shown in FIG. 7. The gel lanes shown on the top left of FIG. 7 show that the mutant with alanine at the 338 position was able to utilize the natural substrate, ATP, more readily than the mutant with serine at that same position. The gel lanes shown on the bottom left of FIG. 7 show that the mutant with alanine in position 338 is also better able to use ATP as a substrate than is the mutant with glycine at that position. The panels on the right side of FIG. 7 tell an even more interesting story. From the top right panel, it is clear that the mutant with the serine at position 338 is not able to utilize $\underline{N}^6$ (cyclopentyl)ATP nearly as well as is the mutant with alanine at that position. However, the bottom panel shows that the mutant with glycine at position 338 is better able to use $\underline{N}^6$ (cyclopentyl)ATP as substrate than is the mutant with alanine at that position.

These results are most promising. It appears that a single mutation is enough to allow the use of this orthogonal substrate. Notably, the mutant with glycine at position 338 appears to be the best engineered v-Src mutant that produced to date. Moreover, it is quite surprising that a glycine substitution would work here. Generally, glycine substitution is usually not expected to work in such situations, because it introduces too much flexibility into the enzyme structure, and thus detrimentally affects the desired outcome.

Example 10

Identifying the Substrates of v-Src: A schematic representation of an experimental approach to identifying v-Src substrates is shown in FIG. 8. The engineered v-Src, such as GST-XD(V323A, I338A), is added to cell extracts or permeabilized cells, along with a radiolabeled orthogonal substrate, such as[γ-$^{32}$P] $\underline{N}^6$-(cyclopentyl)ATP. Typically, this would be done in triplicate. After incubation, the cells would be lysed (if not already lysed), and the resulting samples would be separated by polyacrylamide gel electrophoresis. A western blot taken from the gel and labeled with anti-phosphotyrosine would show all phosphorylated proteins in the sample; and an autoradiogram of the gel would reveal which of those were phosphorylated by v-Src.

Example 11

Synthesis of inhibitors: The pyrazolopyrimidine backbone for the first six inhibitors is shown in FIG. 10A. Synthesis of 4-amino-1-tert-butyl-3-phenylpyrazolo [3,4-d] pyrimidine, having a phenyl group in the "R" position, compound 1 (which is the same structure as PP1, shown on FIG. 9, but without the para-methyl group on the phenyl ring) was carried out according to the method of Hanefeld et al. (76). Compounds 2–6, having cyclobutoyl, cyclopentoyl, cyclohexoyl, benzoyl, and 2-furoyl substituents at the "R" position (FIG. 10B), respectively, were synthesized by treatment of 1 with cyclobutoyl chloride, cyclopentoyl, cyclohexoyl chloride, benzoyl chloride, or furoyl chloride, respectively in dry pyridine for one hour at room temperature. The structures of each of the substitutents are shown in FIG. 10B. Purification by silica gel chromatography afforded pure products in 16–84% yield. Compounds 1–6 (FIG. 10B) were characterized by $^{11}$H-NMR and mass spectral methods.

Example 12

Screening of inhibitors which are orthogonal to wild-type kinases: To identify compounds that would not inhibit any existing cellular kinases, the panel of synthetic pyrazolo pyrimidine analogs (1–6) (FIG. 10) were screened against two closely related purified protein tyrosine kinases, v-Src and Fyn, in a peptide phosphorylation assay using [γ-$^{32}$P] ATP as the radiolabel tracer of kinase activity, as described in Shah et. al. (79). The results showed that each of the compounds 2–6 had IC$_5$0 values of over 400 μM for inhibition of Src and compounds 3 and 5 showed at over 400 μM IC$_{50}$ values for inhibition of wild-type Fyn, indicating that these analogs (2 and 5) are orthogonal to (do not inhibit) these representative wild-type kinases.

Examples 13–15

Deconvoluting protein kinase signaling pathways using conventional genetic and biochemical approaches has been difficult due to the overwhelming number of closely related kinases. If cell permeable inhibitors of each individual kinase could be designed, the role of each protein kinase could be systematically assessed.

An approach of combining chemistry and genetics was developed to obtain the first uniquely specific cell permeable inhibitor of the oncogenic protein tyrosine kinase, v-Src. A functionally silent active site mutation was made in v-Src in order to distinguish it from all other cellular kinases. A tight binding (IC$_{50}$=430 nM) cell permeable inhibitor of this mutant kinase was designed and synthesized which does not inhibit wild-type kinases. In vitro and whole cell assays established the unique specificity of the mutant v-Src/inhibitor pair. This inhibitor reverses the transforming effects of cellular expression of the engineered v-Src, but does not disrupt wild type v-Src mediated cellular transformation. These cell lines differ only by a single amino acid in a single protein kinase, establishing that dramatic changes in cellular signaling can be directly attributed to specific inhibition of the engineered kinase. The generality of this method was tested by engineering another protein tyrosine kinase. The generality of this method was tested by engineering another protein tyrosine kinase, Fyn, to contain the corresponding silent mutation. The same compound was found to be a potent inhibitor (IC$_{50}$=830 nM) of this mutant kinase as well, confirming the generality of the strategy toward making allele specific inhibitors of multiple protein tyrosine kinases.

Allele specific cell permeable inhibitors of individual Src family kinases can be rapidly developed using a combined chemical and genetic approach. Treatment of mutant v-Src transformed NIH 3T3 fibroblasts with a uniquely specific v-Src reverts the morphological hallmarks of transformation. The inhibitor exhibits no effect on cells transformed by the wild-type v-Src allele strongly suggesting that the phenotype induced by inhibitor treatment is a result of a single inhibitory event. The ability to rapidly generate kinases specific inhibitors in a generalizable way will be useful for deconvolution of kinase mediated cellular pathways and for validating novel kinases as good targets for drug discovery both in vitro and in vivo.

As stated earlier, a combined chemical and genetic strategy has been devised which allows for the generation of "chemical sensitive" mutant kinases which are uniquely inhibited by a rationally designed small molecule inhibitor. The approach involves engineering a unique pocket in the active site of the kinase of interest with a functionally silent mutation. A specific inhibitor of the engineered kinase is then synthesized by derivatizing a known kinase inhibitor with a bulky group designed to fit the novel active site pocket. The bulky group kills the potency of the inhibitor for wild type kinases. Successful complementary design, therefore, leads to favorable binding interactions that are only possible in the engineered kinase/inhibitor complex. Transfection of cells with the gene encoding the engineered kinase generates a cell in which only one kinase can be blocked by the designed inhibitor (see FIG. 13).

Importantly, since the mutant kinase serves the same function as the wild-type kinase, an inhibitor of the mutant will affect cell signaling in the same manner as a selective inhibitor of the wild-type kinase in non-transfected cells. The ability to observe the phenotype of cells after selective inhibition of any protein kinase provides a rapid method for determining the unique roles of individuals in signal transduction cascades.

The src family protein tyrosine kinases were targeted for specific inhibitor design because of their ubiquitous importance in mediating cell function. Despite intense investigation, the roles of individual src family members have been difficult to assess because of cellular co-localization and their high sequence identities. Although some potent inhibitors of src family kinases are known, no molecule which can effectively discriminate (20 fold selectively for one src family member) between these closely related enzymes have been identified. Two functionally important src kinases, v-Src and Fyn, were chosen as the primary targets of the mutant kinase/inhibitor pair design. Src kinase has emerged as a leading drug target because of its implication in the oncogenesis of breast, lung, and colon cancers. Although v-Src is the prototype for oncogenic protein tyrosine kinases, no small molecule inhibitors which are highly selective for this kinase have been discovered. Fyn is a src family protein tyrosine kinase which is important in T cell receptor mediated lymphocyte activation. Src and Fyn share a similar domain structure and have approximately 85% amino acid identity in their catalytic domains. The close structural relationship of the src family members provides the ideal test of the ability to engineer enzyme/inhibitor specificity between highly homologous kinases. If one can discriminate between these closely related src members using a cell permeable inhibitor, it is likely that specificity for members of other protein kinase families can also be achieved using a similar approach.

MATERIALS AND METHODS

Chemical synthesis: All starting materials and synthetic reagents were purchased from Aldrich unless otherwise noted. All compounds were characterized by $^1$H NMR and high resolution mass spectrometry. 4-Amino-1-tert-butyl-3-phenylpyrazolo [3,4-d] pyrimidine (2, FIG. 14) was synthesized according to Hanefeld, et al.

General procedure for N-4 acylation of Compound 2 (3a–3g, FIG. 14B). To a solution of 2 (100 mg) dissolved in 2 ml pyridine was added 10 equivalents of the desired acyl chloride at 0(C. The reaction mixture was allowed to warm to room temperature and stirred for 12 hours. The reaction was quenched by the addition of 25 ml water. The resulting mixture was extracted with Et$_2$O and the combined Et$_2$O extracts were washed with 1N HCl and 5% NaHCO$_3$. The Et$_2$O layer was dried over MgSO$_4$ and evaporated. The residue was purified by flash chromatography on 25 g silica gel by elution with 1:1 Et$_2$O/hexanes to yield pure 3a–3g.

4-cyclobutylamido-tert-butyl-3-phenylpyrazolo[3,4-d]pyrimidine (3a): yield 0.0116 g (16%), white powder; HRMS (EI) molecular ion calcd. for C$_{20}$H$_{23}$N$_5$O 349.19049, found 349.18762; $^1$HNMR (300 MHZ, CDCl$_3$, ppm) d 1.86 (9H, s), 1.89–2.27 (6H, m), 3.58 (1H, m), 7.26–7.67 (5H, m), 8.69 (1H,s).

4-cyclopentylamido-1-tert-butyl-3-phenylpyrazolo[3,4-d]pyrimidine (3b): yield 0.0456 g (68%), white powder; HRMS (EI) molecular ion calcd. for C$_{21}$H$_{25}$N$_5$O 363.20615, found 363.20398; $^1$H NMR (270 MHZ, CDCl$_3$, ppm) d 1.41–1.91 (8H, m), 1.87 (9H, s), 2.97 (1H, m), 7.51–7.67 (5H, m), 8.70 (1H,s).

4-cyclohexylamido-1-tert-butyl-3-phenylpyrazolo[3,4-d]pyrimidine (3c): yield 0.0575 g (84%), white powder; HRMS (EI) molecular ion calcd. for C$_{22}$H$_{27}$N$_5$O; $^1$H NMR (270 MHZ, CDCl$_3$, ppm) d 1.21–1.93 (10H, m), 1.86 (9H, s), 2.43 (1H, m), 7.51–7.67 (5H, m), 8.70 (1H, s).

4-2'-furylamido-1-tert-butyl-3-phenylpyrazolo[3,4-d]pyrimidine (3d): yield 0.0342 g (60%), white powder; HRMS (EI) molecular ion calcd. for C$_{20}$H$_{19}$N$_5$O$_2$ 361.15407, found 361.15254; $^1$H NMR (270 MHZ, CDCl$_3$, ppm) d 1.87 (9H, s), 6.52 (1H, d), 7.23 (1H, d), 7.43–7.53 (5H, m), 7.95 (1H, s), 8.59 (1H, s).

4-benzamido-1-tert-butyl-3-phenylpyrazolo[3, 4-d]pyrimidine (3e): yield 0.1309 g (56%), white powder; HRMS (EI) molecular ion calcd. for C$_{22}$H$_{21}$N$_5$O 371.17933, found 371.17324; $^1$H NMR (270 MHZ, CDCl$_3$, ppm) d 1.41–1.91 (8H, m), 7.22–8.11 (10H, m), 8.48 (1H, s).

4-(p-methyl)benzamido-1-tert-butyl-3-phenylpyrazolo[3, 4-d]pyrimidine (3f): yield 0.0751 g (33%), white powder;

HRMS (EI) molecular ion calcd. for $C_{23}H_{23}N_5O$ 385.19499, found 385.18751; $^1$H NMR (270 MHZ, CDCl$_3$, ppm) d 1.88 (9H, s), 2.42 (3H, s), 7.19 (2H, d), 7.41–8.11 (7H, m), 8.49 (1H, s).

4-(p-tert-butyl)benzamido-1-tert-butyl-3-phenylpyrazolo [3,4-d]pyrimidine (3g): yield 0.1050 g (42%), white powder; HRMS (EI) molecular ion calcd. for $C_{26}H_{29}N_5O$ 427.23747, found 427.23474; $^1$H NMR (270 MHZ, CDCl$_3$, ppm) d 1.35 (9H, s), 1.88 (9H, s), 7.38–7.99 (9H, m), 8.50 (1H, s).

General procedure for the reduction of N-4 acyl compounds to N-4 methylene compounds (4b, 4d, 4e, FIG. 14). A round bottom flask was charged with 30 mg LiAlH$_4$. The flask was equipped with a pressure equalizing dropping funnel and flushed with dry argon. The LiAlH$_4$ was suspended in 3 mL THF over an ice bath. Approximately 100 mg of the corresponding N-4 acyl 2 analogue was dissolved in 5 mL THF and added dropwise to the suspension of LiAlH$_4$. The reaction mixture was stirred for 30 min. on the ice bath and subsequently heated to reflux for 30 min. The reaction was quenched by the sequential, dropwise additions of 1 mL EtOAc, 1 mL water, and 1 mL 6N NaOH. After stirring for five minutes, the reaction mixture was filtered through a celite pad, diluted with water and extracted with Et$_2$O. The Et$_2$O extracts were combined, dried over MgSO$_4$, and evaporated. The residue was purified by flash chromatography on 10 g silica gel by elution with 4:1 hexanes/EtOAc.

4-cyclopentylmethylamino-1-tert-butyl-3-phenylpyrazolo[3, 4-d]pyrimidine (4b): yield 0/0649 g (75%), clear oil; HRMS (EI) molecular ion calcd. for $C_{21}H_{27}N_5$ 349.22691, found 349.22420; $^1$H NMR (270 MHZ, CDCl$_3$, ppm) d 1.16–2.14 (9H, m), 1.84 (9H, s), 3.54 (2H, d), 5.51 (1H, s), 7.46–7.67 (5H, m), 8.43 (1H, s).

4-2'-furylmethylamino-1-tert-butyl-3-phenylpyrazolo[3, 4-d]pyrimidine (4d): yield 0.0620 g (66%), beige powder; HRMS (EI) molecular ion calcd. for $C_{20}H_{21}N_5O$ 347.17483, found 371.17330; $^1$H NMR (270 MHZ, CDCl$_3$, ppm) d 1.83 (9H, s), 4.75 (2H, d), 5.64 (1H, s), 6.25 (2H, d), 7.34–7.63 (6H, m), 8.45 (1H, s).

4-benzylamino-1-tert-butyl-3-phenylpyrazolo[3, 4-d] pyrimidine (4e): yield 0.0520 g (54%), white powder; HRMS (EI) molecular ion calcd. for $C_{22}H_{23}N_5$ 357.19559, found 357.19303; $^1$H NMR (270 MHZ, CDCl$_3$, ppm) d 1.82 (9H, s), 4.76 (2H, d), 5.63 (1H, s), 7.28–7.63 (10H, m), 8.44 (1H, s).

Protein Expression and Purification: Site directed mutagenesis and cloning of the genes for the glutathione-S-transferase fusion proteins of WT v-Src SH1 domain. I338G v-Src SH1, WT Fyn, T339G Fyn, and WT Abl into the pGEX-KT plasmid was carried out as described previously. These kinases were expressed in DH5α E. Coli and purified on immobilized glutathione beads (Sigma). PKA was purchased (Pierce) and used without further purification. PKCd was expressed as the 6-His construct using the Bac-to-Bac(expression system (pFastBac B vector). PKCd was purified using a QIAexpress(Ni-NTA agarose column.

In Vitro Kinase Inhibition Assay: IC$_{50}$'s for putative kinase inhibitors were determined by measuring the counts per minute (cpm) of $^{32}$P transferred to an optimized peptide substrate for src family kinases (IYGEFKKK (SEQ ID NO: 12)). Various concentrations of inhibitor were incubated with 50 mM Tris (pH 8.0), 10 mM MgCl$_2$, 1.6 mM glutathione, 1 mg/mL BSA, 133 mM IYGEFKKK (SEQ ID NO: 12), 3.5% DMSO, 0.05 mM Kinase and 11 nM (2 mCi) [γ-$^{32}$P] ATP (6000 Ci/mmol, NEN) in a total volume of 30 mL for 30 minutes. Reaction mixtures (25 ml) were spotted onto a phosphocellulose disk, immersed in 10% HOAc, and washed with 0.5% H$_3$PO$_4$. The transfer of $^{32}$P was measured by standard scintillation counting. IC$_{50}$ was defined to be the concentration of inhibitor at which the cpm was 50% of the control disk. When the IC$_{50}$ fell between two measured concentrations it was calculated based on the assumption of an inversely proportional relationship between inhibitor concentration and cpm between the two data points. Because the solubility limit of the inhibitor analogues in aqueous solutions is (300 μM, IC$_{50}$ values to (250 μM are approximately as fill titrations to the upper limit of inhibition could not be tested. IC$_{50}$'s for non-scr family kinases were measured equivalently with the following exceptions. Kemptide (Pierce, 133 mg/mL) was used as the substrate for PKA. An optimized Abl; (EAIYAAPFAKKK (SEQ ID NO: 13), 133 mg/ml) was used for Abl assays. PKCd assays were performed in the presence of 17 ng/ml diacyl glycerol (Sigma) and 17 ng/ml phosphatidyl serine (Sigma) with 170 ng/ml histone (Sigma) as the kinase substrate.

Murine B Cell Assay: Splenic lymphocytes were isolated from 6–20 week old Balb/c or C57/B6 mice. The cells were washed out of the spleen into RPMI media containing 1 mg/mL DNase in and the red blood cells were lysed in 17 mM tris-ammonium chloride, pH 7.2. Approximately 4×10$^6$ cells were incubated at 37° C. for 30 minutes with 100 mM of 3 g or 2 in 1.1% DMSO. B cell stimulation was initiated by the addition of 2 mg of goat anti-mouse IgM (Jackson Immuno Research, cat#115-005-075) and subsequent incubation for 5 minutes at 37° C. The cells were isolated by centrifugation (13,000 rpm, 2 min) and lysed (lysis buffer: 1% Triton X-100, 50 mM tris pH 7.4, 2 mM EDTA, 150 mM NaCl, 100 mM PMSF, 2 mM sodium orthovanadate, 10 mg/mL leupeptin, 10 mg/mL apoprotin). The cellular debris was then pelleted at 13,000 rpm for 15 min. Cellular proteins were separated by 10% polyacrylamide gel electrophoresis and transferred to a nitrocellulose membrane by Western blotting. Phosphotyrosine containing proteins were visualized by immunoblotting with anti-phosphotyrosine antibody (Upstate Biotechnology, Inc.).

Retroviral Infection of NIH 3T3 Fibroblasts: Genes encoding WT and I338G v-Src were transfected into a packaging cell line and NIH 3T3 fibroblasts were retrovirally infected using the pBabe retroviral vector and a puromycin (2.5 mg/mL) selectable marker as described (Shah, K., Liu, Y., Shokat, K. M., in preparation). WT and I338G v-Src transformed cells were cultured in DMEM/10% BCS containing 2.5 mg/mL puromycin).

Inhibition of v-Src in NIH3T3 Fibroblasts: Non-transformed NIH3T3 cells, WT v-Src transformed NIH3T3 cells, and I338G v-Src transformed NIH3T3 cells were incubated at 37° C. with 1.1% DMSO or 100 μM 3 g in 1.1% DMSO. After 12 hours, the cells were washed with PBS and lysed (lysis buffer: 1% Triton X-100, 50 mM tris pH 7.4, 2 mM EDTA, 150 mM NaCl, 100 mM phenylmethylsulphonyl fluoride, 2 mM sodium orthovanadate, 10 mg/mL leupeptin, 10 mg/mL apoprotin). The lysate was clarified by centrifugation at 13,000 rpm for 15 min. Lysate protein concentrations were normalized and equal volumes of the lysate were resolved electrophoretically and analyzed for phosphotyrosine content as described above.

Microscopy: Non-transformed, WT v-Src transformed, and I338G v-Src transformed NIH3T3 fibroblasts were grown in DMEM/10% BCS on tissue culture treated slides. V-Src expressing cells were treated with either 1.1% DMSO or 100 μM 3 g in 1.1% DMSO. After 48 hours cells were photographed at 400×magnification on an Nikon TMS light microscope. Immediately following light microscopy, the cells were fixed for 20 min in 3.7% formaldehyde/PBS and permeabilized for 60 sec in 0.2% Triton X-100/PBS. Permeabilized cells were incubated with 200 ng/mL phalloidin-FITC/PBS for 20 min. Slides were rinsed with PBS and polymerized actin was visualized by fluorescence microscopy at 600× magnification on a Zeiss fluorescence microscope.

RESULTS

Enzyme engineering: A functionally conserved residue in the ATP binding pocket of v-Src (Ile 338) was developed which could be mutated to glycine without altering the phosphoacceptor specificity or biological function of the kinase. The space creating mutation causes only a modest drop in $k_{cat}$, a modest increase in the $K_m$ for ATP and no quantitative changes in the level of fibroblast transformation (Shah K, unpublished results). The biological substrates of the mutant v-Src are unchanged and I338G v-Src carries out the same biological functions as wild type v-Src. All crystal structures of ATP bound protein kinases have revealed a close contact interaction between the residue corresponding to 338 (Src numbering) and ATP. Analysis of protein kinase sequence alignments confirmed that residue 338 contains a bulky side chain (usually Thr, Ile, Leu, Met, or Phe) in all known eukaryotic protein kinases. Thus, a glycine mutation at the 338 position should create a novel pocket that is not present in any wild type kinase. Due to the expanded ATP binding site, the glycine mutant kinases should accept bulky inhibitors that could not bind wild type kinases. Using standard methods the glutathione-S-transferase (GST) fusion protein of the WT and I338G v-Src catalytic domains was cloned, expressed and purified as described previously. WT Fyn, T339G Fyn (Src numbering), and WT Abl were also expressed and purified as GST fusion proteins.

Inhibitor design and synthesis: To test the basic design strategy the WT and I338G v-Src SH1 domains against a previously synthesized panel of N-6 substituted adenosine molecules for selective inhibition of I338G v-Src over WR v-Src. Because adenosine is only a moderate inhibitor of src family protein tyrosine kinases, to discover a potent inhibitor of the engineered kinase was not expected. As expected, all of the N-6 adenosine analogues inhibited I338G v-Src more potently than WT v-Src. The most potent inhibitor found in this screen was N-6 cyclopentyloxyadenosine (1, FIG. 14A) with a 50% inhibitory concentration ($IC_{50}$) of 1 mM for I338G v-Src. Subsequent experiments to test for selectivity demonstrated that N-6 cyclopentyloxyadenosine showed no detectable in vitro inhibition of WT v-Src or Fyn at concentrations up to 400 mM. This first screen encouraged us to pursue the strategy of developing novel inhibitors of I338G v-Src since the design had allowed us to readily overcome selectivity barriers which are major problems in conventional inhibitor discovery.

As inhibitors, adenosine analogues are not ideal because of the many cellular functions performed by adenosine as well as the large number of cellular proteins which bind adenosine. N-6 adenosine analogues have been shown to act as adenosine receptor agonists and antagonists, and one can imagine N-6 adenosine analogues acting as substrates for nucleoside kinases. For these reasons a class of known protein tyrosine kinase inhibitors that are not direct analogues of biologically known molecules were used. The design strategy called for a core structure which exhibits potent inhibition of multiple wild type kinases and is easily synthesized. Also, the binding orientation of the molecule in the enzyme active site must be known or readily predictable. In addition, the molecule must bind in a manner in which the site pointing toward Ile338 can be easily modified. As the core inhibitor structure 4-amino-1-tert-butyl-3-phenylpyrazolo[3,4-d]pyrimidine (2, FIG. 14B) was used. This molecule is a derivative of 4-amino-1-tert-butyl-3-(p-methylphenyl)pyrazolo[3,4-d]pyrimidine (PP1) which was reported by Hanke and co-workers as a potent src family kinase inhibitor. Based on the co-crystal structure of the src family kinase, Hck, bound to the general kinase inhibitor, quercetin (5, FIG. 15A), it was postulated that 2 binds to src family kinases in a conformation similar to that of ATP. The predicted binding orientation of 2 in Hck is shown in an overlay with the known Hck co-crystal structures of AMP PNP (6) and quercetin (FIG. 15B). In this conformation the easily derivatizable N-4 position of 2 corresponds to the N-6 of ATP (close contact with residue 338, FIG. 15C.) And the tert-butyl moiety roughly corresponds to the ribose ring of ATP. It was hypothesized that in this orientation, the C-3 phenyl ring of 2 could bind in a pocket that surrounds the N-7 of ATP as seen in the Hck/quercetin co-crystal structure. This analysis lead us to synthesize a small panel of N-4 derivatized analogues of 2 (FIG. 14).

Identification of a uniquely selective inhibitor: The panel of pyrazolo[3,4-d]pyrimidines was screened against WT and I338G v-Src kinases. All of the analogues are better inhibitors of the engineered v-Src as compared to wild type, confirming the prediction of the binding orientation of 2 in the kinase active site. Any derivatization of 2 at the N-4 position destroys the inhibitory activity against WT v-Src (no detectable inhibition at the limit of solubility, 300 mM). All 10 analogues demonstrated measurable inhibition of I338G v-Src and several of the compounds have $IC_{50}$'s in the low mM range. The N-4 -(p-tert-butyl)benzamido-1-tert-butyl-3-phenyl analogue (3 g of FIG. 14) is the most potent inhibitor of I338G v-Src in the panel ($IC_{50}$=430 nm). This molecule shows no inhibition of WT v-Src at 300 mM suggesting that 3 g is at least a 1000 fold better inhibitor of the mutant v-Src as compared to wild type. The large size of the derivatization needed to achieve sub-micromolar potency for the I338G v-Src active site was rather unexpected. Only four carbon atoms were removed from the ATP binding site and derivatized the parent molecule with eleven carbon atoms. This discrepancy may be due to an imperfection in the binding prediction. Also the Ile to Gly mutation may confer greater flexibility to the enzyme active site allowing the mutant kinase to accept a larger inhibitor analogue than predicted. To confirm that 3 g does inhibit I338G v-src at the ATP binding site it was investigated its kinetics of inhibition at various ATP concentrations. Lineweaver-Burk analysis confirmed that 3 g does inhibit I338G v-Src competitively with respect to ATP with an inhibitory constant ($K_i$) of approximately 400 nM.

The panel of inhibitor analogues was next screened against WT Fyn to investigate their potential to cross react with this kinase. WT Fyn was chosen as the "worst case" control of wild type kinases because the published parent molecule, PP1, and 2 (FIG. 14) are highly potent (low nM) Fyn inhibitors. Many of the 10 synthetic analogues did not display high selectivity for the target kinase. The N-acyl analogues with saturated ring systems (3a–3c, FIG. 14) effectively inhibit wild type Fyn. The N-methylene compounds (4b, 4d, 4e, FIG. 14) are sufficiently orthogonal to WT Fyn but show only poor to moderate inhibition of the engineered v-Src. Importantly, 3 g (FIG. 14), the most potent inhibitor of the mutant v-Src inhibited WT Fyn very weakly ($IC_{50}$=300 mM). Thus, 3 g inhibits the engineered v-Src over 700 times more effectively than WT Fyn, which is likely to be the wild type cellular kinase which is most capable of binding the molecule. Other non-src family kinases tested were fortuitously inhibited by 3 g in vitro. The serine/threonine kinases, PKCd and PKA, were not detectably inhibited at concentrations up to 300 mM. Likewise, 3 g exhibited only weak inhibition ($IC_{50}$>300 mM) of the Abl protein tyrosine kinase. Therefore 3 g satisfied all of the initial design requirements for potent selective inhibition of one engineered kinase.

Selectivity in whole cells: To further demonstrate that 3 g (FIG. 14) does not inhibit wild type protein tyrosine kinases it was investigated the effects of 3 g treatment on the B cell receptor (B CR) mediated phosphorylation cascade. Src family (Fyn, Lyn, Lck, Blk) and non-src family protein tyrosine kinases (Btk, Syk) are known to be activated upon BCR cross-linking. Due to the amplifying nature of the BCR mediated cascade, inhibition of any of these kinases would dramatically alter the distribution and intensity of post-activation cellular phosphotyrosine. Because 3 g was designed to be sterically incompatible with the active sites of wild type kinases, it should not disrupt tyrosine phosphorylation dependent signaling in wild type B cells. Treatment of 100 µM 3 g with antigen receptor cross linked murine B cells has no effect on the phosphotyrosine pattern of B cell stimulation. The signal intensities of all the major bands are unchanged and only slight depletion of some minor bands is detectable, confirming that 3 g does not appreciably inhibit the panel of protein tyrosine kinases that are activated by BCR cross linking. Treatment of B cells with 100 [mM2] mM 2, however, causes a significant reduction in tyrosine phosphorylation (FIG. 4, lane 4) that is consistent with its potent inhibition of wild types src family kinases.

Selective inhibition of I338G v-Src in NIH3T3 cells: In order to use the selective inhibitor to study a Src mediated pathway it was retrovirally introduced both WT and I338G v-Src into NIH3T3 fibroblasts. These cells acquire a transformed phenotype which is dependent on v-Src expression. It was shown that 3 g (FIG. 14) could selectively disturb the Src dependent signal transduction pathway of I338G v-Src transformed cells while not affecting WT transformed cells. Treatment of WT v-Src infected cells (100 µM 3 g) causes no loss of tyrosine phosphorylation compared to control DMSO treated lanes (FIG. 16), demonstrating that the designed inhibitor does not inhibit WT v-Src or any of the other protein tyrosine kinases that are activated by v-Src mediated cellular transformation. Equivalent treatment of I338G v-Src transformed cells gives rise to a dramatic diminution in the tyrosine phosphorylation of the putative v-Src substrate, p36, as well as a moderate overall decrease in the cellular level of phosphotyrosine. Previously, it has been shown that treatment of v-Src transformed cells with general protein tyrosine kinase inhibitors causes a reduction in the tyrosine phosphorylation of a 36 kD protein. It is thought that p36 is associated with a specific phosphotyrosine phosphatase, possibly explaining its rapid dephosphorylation in inhibitor treated cells. The 3 g $IC_{50}$ for p36 phosphotyrosine signal in I338G v-Src expressing cells (50 mM) is roughly 100 times the in vitro value. This is presumably due to the fact that the inhibitor must compete with millimolar concentrations of ATP for the kinase active site in the cellular experiments.

Selective inhibition of I338G mutant v-Src reverses transformed cell morphology: V-Src activity is required for Rous sarcoma virus transformation of mammalian cells. Treatment of the I338G v-Src expressing NIH 3T3 cells with 100 µM 3 g (FIG. 14) caused dramatic changes in cell morphology which are consistent with the reversal of transformation (FIG. 17). The mutant cells that were treated with inhibitor 3 g appeared flat and did not exhibit growth characteristics of transformed cells (i.e. the ability to grow on top of one another). Under identical conditions, WT v-Src infected cells demonstrated the prototypical rounded morphology and overlapping growth patterns of transformed cells.

To further demonstrate the selective reversal of cell morphology fluorescence microscopy was used to view 3 g treated cells after staining the cellular polymerized actin with phalloidin-FITC (FIG. 17). Non-transformed NIH3T3 cells show long actin spindles that form across the cells. V-Src transformed cells (both WT and I338G) appear rounded with no discernible pattern of actin formation. In agreement with the light microscopy data, inhibitor treated WT v-Src expressing cells appear indistinguishable from untreated WT cells. However, 3 g treated I388G v-Src expressing cells have defined polymerized actin strings, strongly resembling the actin formations of non-transformed NIH3T3 fibroblasts. These inhibitor treated cells have an exaggerated flattened morphology and show peripheral actin staining that is not present in the non-transformed NIH3T3 cells. This data shows that 3 g can uniquely induce morphological changes in cells which are engineered to contain a single amino acid change in the kinase of interest. This is the first demonstration that a small molecule inhibitor selective for a protein tyrosine kinase oncogene product can revert the morphological changes associated with cellular transformation. Previous examples of morphological reversion of transformation by herbimycin A (and other benzoquinone ansamycins) have recently been shown to operate via a mechanism unrelated to kinase inhibition consisting of heat shock protein (hsp90) mediated targeting of the oncogenic protein tyrosine kinase to the proteasome.

Generalization to other kinases: The advantage of using mutagenesis to provide a unique molecular difference between the enzyme of interest and all others is that, due to the conserved kinase fold, the approach should be extendible across the kinase superfamily. Almost all known protein kinases contain a bulky side chain at the position corresponding to residue 338 of v-Src. Therefore a space creating mutation at this position should render multiple kinases susceptible to selective inhibition. To test this the inhibition of the analogues against T339G Fyn was measured. There exists a striking similarity in the structure activity relationships of the analogues for I338G v-Src and T339G Fyn. In agreement with the data for I338G v-Src, 3 g was the most potent inhibitor analogue against T339G Fyn, exhibiting an $IC_{50}$ of 830 nM. This corresponds to greater than 300 fold selectivity for T339G Fyn over WT Fyn. The implication of this data is that multiple protein tyrosine kinases can be systematically engineered to preferentially accept one inhibitor analogue without the need to screen large libraries of putative inhibitors.

The above, describes a novel approach to selective protein kinase inhibition through the complementary engineering of chemical sensitive kinases and rationally designed inhibitors. It was demonstrated that high selectivity for the target kinase can be achieved in whole cells, and that active site inhibition of an oncogenic protein tyrosine kinase can be sufficient for the disruption of a transformed cell morphology. Because the approach is easily generalized, it should have far reaching applications in deconvoluting signal transduction pathways as well as validation of kinases as targets for drug design. The pace of effective drug discovery is limited by the identification and validation of important drug targets. This is not a trivial problem in a milieu of 2000 homologous proteins. The use of chemical sensitive mutants of protein kinases expands the capability to probe the cellular and physiological effects of pharmacological kinase inhibition. Since transfected cell lines and even "knock-in" mice can now be generated rapidly, the approach should greatly expedite the process of testing the effects of selective inhibition of a given kinase in a whole cell or animal model. As more inhibitor-bound protein kinase crystal structures become available, this strategy will allow for the systematic investigation of the effects of time and dose dependent inhibition of any given kinase in the scope of an entire signal transduction cascade.

Example 16
Generation of Mutant Specific Nanomolar Protein Tyrosine Kinase Inhibitors via a Chemical Genetic Approach Based on the experiments herein, directed structure-based design of kinase/inhibitor pairs has yielded mutant specific, cell-permeable inhibitors of engineered Src family kinases with potencies that have not been attainable with conventional inhibitor screening methods. By mutating the active site of v-Src it has not only differentiated one protein kinase from all others but simultaneously created a newly accessible binding site to use in designing more potent inhibitors. Thus, one can increase both potency and selectivity compared to traditional inhibitor design strategies. The design is highly generalizable, owing to the conservation of kinases at the site corresponding to Ile338 in v-Src. In fact, recent work has shown that the sensitivity of mitogen-activated protein kinases (MAPKs) to pyrdinylimidazole inhibitors is in large part controlled by the side chain of residue 106 which corresponds to 338 of Src. The primary advantage of the approach to the design of selective kinase inhibitors for the study of protein kinase function is the ability to genetically "program" the kinase of interest for unique inhibition by a small molecule. This allows for the unambiguous assignment of the activity of a specific kinase to the induced phenotype. The combination of genetic manipulation and small molecule control of enzyme activity should have far reaching applications in the pharmacological validation of protein kinases as viable drug targets in cells as well as whole organisms.

MATERIALS AND METHODS

Protein Expression and Purification: Site directed mutagenesis and cloning of the genes for the glutathione-S-transferase fusion proteins of wild type v-Src catalytic domain, I338G v-Src SH1, and WT Fyn into the pGEX-KT plasmid was carried out as described previously. These kinases were expressed in DH5α $E.$ $Coli$ and purified on immobilized glutathione beads (Sigma).

In Vitro Kinase Inhibition Assay: $IC_{50}$'s for putative kinase inhibitors were determined by measuring counts per minute (cpm) of $^{32}P$ transferred to an optimized peptide substrate for src family kinases (IYGEFKKK, SEQ ID NO: 12). Various concentrations of inhibitor were incubated with 50 mM Tris (pH 8.0), 10 mM $MgCl_2$, 1.6 mM glutathione, 1 mg/mL BSA, 100 mM IYGEFKKK (SEQ ID NO: 12), 3.3% DMSO, the appropriate kinase and 11 nM (2 mCi) [γ-$^{32}P$] ATP (6000 Ci/mmol, NEN) in a total volume of 30 mL for 30 minutes. Reaction mixtures (25 mL) were spotted onto a phosphocellulose disk, immersed in 10% HOAc, and washed with 0.5% $H_3PO_4$. The transfer of $^{32}P$ was measured by standard scintillation counting. $IC_{50}$ was defined to be the concentration of inhibitor at which the cpm was 50% of the control disk. When the $IC_{50}$ fell between two measured concentrations it was calculated based on the assumption of an inversely proportional relationship between inhibitor concentration and cpm between the two data points.

Chemical synthesis: All starting materials and synthetic reagents were purchased from commercial suppliers unless otherwise noted. Acid chlorides that were not readily commercially available (3c, 3d, 3e, 3h, 3i) were synthesized by treating the corresponding carboxylic acids with excess oxalyl chloride and catalytic DMF in diethyl ether. All PP1 analogues were synthesized according to Hanefeld, et al.

4-amino-1-(tert-butyl)-3-(1-naphthyl)pyrazolo[3,4-d] pyrimidine (6a, FIG. 18). White powder; $^1H$ NMR (270 MHZ $CDCl_3$) d 1.92 (s, 9H), 5.04 (m, 2H), 7.43–7.73 (m, 4H), 7-92–8.02 (m, 3H), 8.34 (s, 1H); HRMS (EI) molecular ion calcd. for $C_{19}H_{19}N_5$ 317.16427, found 317.16247.

4-amino-1-(tert-butyl)-3-(2'-naphthyl)pyrazolo[3,4-d] pyrimidine (6b, FIG. 18). White powder; $^1H$ NMR (270 MHZ $CDCl_3$) d 1.88 (s, 9H), 5.55 (m, 2H), 7.56–8.00 (m, 6H), 8.16 (s, 1H), 8.39 (s, 1H); HRMS (EI) molecular ion calcd. for $C_{19}H_{19}N_5$ 317.16427, found 317.16359.

4-amino-1-(tert-butyl)-3-(m-phenoxyphenyl)pyrazolo[3, 4-d]pyrimidine (6c, FIG. 18). White powder; $^1H$ NMR (270 MHZ $CDCl_3$) d 1.83 (s, 9H), 5.61 (m, 2H), 7.08–7.49 (m. 9H), 8.35 (s, 1H), HRMS (EI) molecular ion calcd. for $C_{21}H_{21}N_5$ 359.17483, found 359.17325.

4-amino-1-(tert-butyl)-3-(m-benzyloxyphenyl)pyrazolo [3,4-d]pyrimidine (6d, FIG. 18). White powder; $^1H$ NMR (270 MHZ $CDCl_3$) d 1.85 (s, 9H), 5.17 (s, 2H), 5.55 (m, 2H), 5.74 (s, 2H), 7.10 (d, J=8 Hz, 1H), 7.27–7.48 (m, 8H), 8.34 (s, 1H), HRMS (EI) molecular ion calcd. for $C_{22}H_{23}N_5O$ 373.19049, found 373.18833.

4-amino-1-(tert-butyl)-3-(m-(2',6'-dichloro) benzyloxyphenyl)pyrazolo[3,4-d]pyrimidine (6e, FIG. 18). White powder; $^1H$ NMR (270 MHZ $CDCl_3$) d 1.85 (s, 9H), 5.36 (m, 2H), 5.74 (s, 2H), 7.11–7.51 (m, 7H), 8.36 (s, 1H), HRMS (EI) molecular ion calcd. for $C_{22}H_{21}Cl_2N_5O$ 441.11263, found 441.11050.

4-amino-1-(tert-butyl)-3-piperonylpyrazolo[3,4-d] pyrimidine (6f, FIG. 18). White powder; $^1H$ NMR (270 MHZ $CDCl_3$) d 1.83 (s, 9H), 5.70 (m, 2H), 6.05 (s, 2H), 6.96 (d, J=8 Hz, 1H), 7.13–7.27 (m, 2H), 8.34 (s, 1H), HRMS (EI) molecular ion calcd. for $C_{16}H_{17}N_5O_2$ 311.13841, found 311.13777.

4-amino-1-(tert-butyl)-3-(p-tert-butylphenyl)pyrazolo[3, 4-d]pyrimidine (6 g, FIG. 18). White powder; $^1H$ NMR (300 MHZ $CDCl_3$) d 1.38 (s, 9H), 1.84 (m, 9H), 5.83 (s, 2H), 7.58 (dd, J=8 Hz, 12 Hz, 4H), 8.33 (s, 1H), HRMS (EI) molecular ion calcd. for $C_{19}H_{25}N_5$ 323.21125, found 323.21024.

4-amino-1-(tert-butyl)-3-(1'-naphthylmethyl)pyrazolo[3, 4-d]pyrimidine (6h, FIG. 18). White powder $^1H$ NMR (270 MHZ $CDCl_3$) d 1.85 (s, 9H), 4.76 (s, 2H), 5.04 (s, 2H), 7.19 (d, J=6 Hz, 1H) 7.39 (t, J=8 Hz, 1H) 7.55 (t, J=4 Hz, 2H), 7.79–7.92 (m, 2H), 8.20 (d, J=8 Hz, 1H), 8.24 (s, 1H); HRMS (EI) molecular ion calcd. for $C_{20}H_{21}N_5$ 331.17993, found 331.17951.

4-amino-1-(tert-butyl)-3-(1'-naphthoxymethyl)pyrazolo [3,4-d]pyrimidine (6i, FIG. 18). Beige powder $^1H$ NMR (270 MHZ $CDCl_3$) d 1.83 (s, 9H), 5.57 (m, 2H), 6.12 (s, 2H), 7.07 (d, J=6 Hz, 1H) 7.39–7.54 (m, 4H), 7.84 (d, J=8 Hz, 1H), 8.25 (s, 1H); HRMS (EI) molecular ion calcd. for $C_{20}H_{21}N_5O$ found 347.17483 found 347.17408.

RESULTS

Inhibitor Design and Modeling: Initially the $N^4$ exocyclic amine of the Src family kinase inhibitor 4-amino-1(tert-butyl)-3-phenylpyrazolo[3,4-d]pyrimidine (1, FIG. 19) was utilized as a chemical hook to which could be tethered to bulky groups to destroy the molecule's affinity for wild type kinases (1 is a des-methyl modified analogue of PP1, reported by Hanke et al.). While this approach did yield a very selective inhibitor (2, FIG. 19) of the engineered v-Src kinase (I338G v-Src), it was not totally satisfactory because more than an order to magnitude in binding energy from the starting affinity of the parent molecule for wild type Src family kinases was lost (see FIG. 19).

To increase the potency of the inhibitors, the binding of 1 was modeled in the active site of the Src family kinase, Hck. Using the molecular graphics program, GRASP, the protein was compared to the surface map of the ATP binding pocket of Hck with the corresponding predicted map of the expanded pocket in the engineered protein kinase, T338G Hck. From this model, it was deduced that derivatization of $N^4$ was not the only means of generating complementary van der Waal's interactions with the unique binding pocket of I338G v-Src. It could be seen from the surface map that derivatization of the $C^3$ phenyl ring of 1 (ex: phenyl ring replaced with naphthyl ring system, compound 6a) with a bulky group leads to steric clash between the derivatized inhibitor and the molecular surface created by Thr338. Mutation of residue 338 to glycine generates a unique binding pocket which is predicted to be large enough to accept the naphthyl analogue of 1. Derivatization of this phenyl group with hydrophobic substituents affords compounds that complement the corresponding I338G v-Src active site, without disrupting any potential hydrogen bonding interactions at $N^4$. In addition, this added bulk at the $C^3$ moiety causes these molecules to be sterically incompatible with the active sites of wild type protein tyrosine kinases, affording high specificity for the suitably engineered v-Src.

Inhibitor Synthesis and Screening: A small panel of $C^3$ derivatized PP1 analogues (6a–6i) was synthesized as shown in FIG. 18. The group of modified inhibitors was screened against the catalytic domain of the target kinase, I338G v-Src, which was expressed in bacteria and purified as a glutathione-S-transferase (GST) fusion protein. All of the $C^3$ derivatized analogues are more potent inhibitors of I338G v-Src than the most potent molecule (2, $IC_{50}$=430 nM) identified from the first generation panel of $N^4$ derivatized compounds (see Table 3). Four of the molecules (6a, 6b, 6d, 6h) inhibit the target kinase at low nM concentrations with the two naphthyl isomers (6a, 6b) exhibiting the greatest potency ($IC_{50}$=1.5 nM). Under the conditions of the assay the parent molecule, PP1, inhibited its optimal target, Fyn, at only $IC_{50}$=30 nM). This date shows that an inhibitor design strategy combining enzyme engineering with directed small molecule synthesis can not only match the potency of molecules identified through screening of large libraries, but can lead to a significant increase (20 fold in the case of 6a, 6b) in affinity over previously optimized inhibitors of wild type kinases. Compounds having the formula of 6a and 6b are the most potent inhibitors of any Src family protein tyrosine kinase that have been reported to date.

TABLE 3

50% inhibitory concentrations ($1C_{50}$'s) of $C^3$ derivatized PP1 analogues for engineered and wild type Src family protein tyrosine kinases.

| Compound | I338G v-Src ($\mu$M) | vSrc($\mu$M) | Fyn($\mu$M) |
| --- | --- | --- | --- |
| 6a | 0.0015 | 1.0 | 0.60 |
| 6b | 0.0015 | 1.0 | 0.13 |
| 6c | 0.14 | 40 | 0.80 |
| 6d | 0.0070 | 26 | 6.0 |
| 6e | 0.13 | 300 | 84 |
| 6f | 0.025 | 3.1 | 0.040 |
| 6g | 0.099 | 65 | 9.2 |
| 6h | 0.0042 | 28 | 1.1 |

TABLE 3-continued

50% inhibitory concentrations ($1C_{50}$'s) of $C^3$ derivatized PP1 analogues for engineered and wild type Src family protein tyrosine kinases.

| Compound | I338G v-Src ($\mu$M) | vSrc($\mu$M) | Fyn($\mu$M) |
| --- | --- | --- | --- |
| 6i | 0.045 | >300 | >300 |
| 6j | 0.020 | >300 | >300 |

Importantly, all nine molecules show striking selectivity for I338G v-Src with respect to the wild type enzyme. The in vitro selectivities range from 120 for the piperonyl compound (6f) to as high as >6500 for the naphthoxy methyl derivative (6i). This range is similar to the selectivities generated by derivatization of $N^4$, further validating both the prediction of binding orientation for the parent inhibitor as well as the modeling of the expanded binding site of I338G v-Src. These selectivities compare favorably to those from other strategies which combine protein engineering with small molecule recognition, as well as strategies that utilize selection techniques to identify tight binding proteins from large pools of mutants.

To further confirm the selectivity for the target kinase, the panel was screened against wild type Fyn (Table 3). This is presumably a more stringent control inhibition of wild type v-Src because Fyn is more potently inhibited by PP1. Three of the four most potent inhibitors (6a, 6d, 6h, FIG. 18) showed sufficient selectivity for the target kinase (100 fold) with respect to wild type Fyn. The most potent inhibitor of I338G v-Src, 6a, binds wild type Fyn at 600 nM representing 400 fold selectivity for the designed target.

Cellular Inhibition of the Target Kinase: Two cell culture systems were employed to investigate the utility of compound 6a as a specific kinase inhibitor in the context of a whole cell. First NIH3T3 fibroblast cell lines that express either wild type or I338G v-Src were generated by retroviral infection. Because v-Src is a highly activated, oncogenic protein tyrosine kinase the majority of the tyrosine phosphorylation in these cells is a result of v-Src expression. To investigate the selective inhibition of the engineered v-Src, both wild type and I338G v-Src expressing cells were incubated with varying concentrations of 6a. Anti-phosphotyrosine blots of lysates derived from these cells demonstrate that 6a strongly diminishes tyrosine phosphorylation in a concentration dependent manner within minutes (FIG. 20, lanes 3–8). In agreement with the in vitro potencies, the ablation of phosphotyrosine signal from 6a is much more rapid and complete than that caused by the most potent $N^4$ derivatized analogue in the same cell line. Wild type v-Src expressing cells in the presence of 500 nM 6a show no loss of phosphotyrosine signal (lanes 1 and 2) and can be grown in the presence of the compound for days with no loss of tyrosine phosphorylation or apparent cytotoxicity.

To further confirm the selectivity of 6a, Jurkat cells (a human derived T cell line with no engineered kinases) were treated with the general protein tyrosine phosphatase inhibitor, pervanadate, which covalently binds to a catalytically essential cysteine in the active site of phosphotyrosine phosphatases. The presence of pervanadate effectively shifts the cellular equilibrium of phosphotyrosine giving rise to a large increase in tyrosine phosphorylation (see FIG. 20, compare lane 10 to lane 9). When these cells are treated with 500 nM 6a (lane 11) there is no detectable decrease in phosphorylation, indicating that none of the wild type protein tyrosine kinases in Jurkat cells are appreciably inhibited by the designed inhibitor. PP1 was used as a positive control for inhibition of wild type kinases at 10 μM (lane 12) the concentration at which it has previously been shown to strongly suppress T cell receptor mediated tyrosine phosphorylation.

Selective Disruption of Cellular Transformation: The rapid generation of highly selective kinase inhibitors should have far reaching applications in the pharmacological validation of protein kinases as viable drug targets. To test this idea it was investigated whether or not compound 6a (FIG. 18) could selectively disrupt oncogenic transformation in cells that expressed the target kinase. Normal NIH3T3 fibroblasts have long fibers of polymerized actin across the cells that can be visualized by staining the cells with phalloidin conjugated to rhodamine (FIG. 21A.). Cells that express an oncogenic protein (either wild type or I338G v-Src) are rounded and therefore have a diffuse pattern of actin (FIG. 21B.). Wild type v-Src expressing cells that are treated with 6a appear indistinguishable from untreated wild type cells, suggesting that 6a has no effect on this non-mutant cell line. However, cells expressing the target kinase have clear actin fibers and appear indistinguishable from normal NIH3T3 fibroblasts when incubated with 250 nM 6a for 16 hours. From this data it is clear that small molecule inhibition of v-Src's catalytic activity is sufficient to block its role in oncogenesis.

Example 17
Development of General Chemical Switch for Targeting any Protein Kinase of Choice for Specific Inhibition In the examples above Src family protein tyrosine kinases were engineered to contain a unique binding pocket which is not present in any wild-type protein kinase. These mutants are uniquely sensitive to derivative of the Src family selective inhibitor PP1 (10, FIG. 28) (85–87) which have been modified to complement the enlargement of the mutant's active site. All protein kinases identified to date possess the conserved active site feature exploited by this approach (88). However, since the PP1 scaffold is selective for Src family kinases, it would presumably not provide a widely generalizable strategy for inhibiting kinases across the superfamily (not be the ideal parent compound for broad applications across divergent kinase families) (85). Therefore it is desirable to develop a general chemical switch, based on a more promiscuous kinase inhibitor, which could be used to rapidly target any protein kinase of choice for specific inhibition.

Indolocarbazole Natural Product (+)K252a and Mutant Kinases: To re-engineer the kinase/inhibitor interface, indolocarbazole natural product (+)-K252a (1, FIG. 22A) was selected. The product satisfies three important design criteria: 1) 1 inhibits many different families of protein kinases; 2) the binding orientation of 1 is readily predictable; 3) rationally derivatized analogs of 1 are synthetically accessible. K252a is a very general protein kinase inhibitor which was predicted to bind kinase active sites in an orientation identical to that of the closely related compound, staurosporine (2, FIG. 22A). K252a has been reported to be a potent ($IC_{50} \leq 30$ nM) inhibitor of protein kinase C, protein kinase A, cGMP dependent protein kinase, myosin light chain kinase, and Trk family tyrosin kinases (89, 90). This example shows that the same molecule can efficiently inhibit Src family kinases, cyclin dependent kinases, and calmodulin dependent kinases (FIG. 27). The structures of 2 (FIG. 22A) bound to protein kinase A (91), cyclin dependent kinase 2 (CDK2) (92), and Lck (93) have recently been solved, allowing for structure based design to engineer unique sensitivity to the indolocarbazole class of kinase inhibitors (FIG. 22B).

As shown in the examples above, mutation of I338 to glycine was sufficient to confer unique inhibitor sensitivity to a PP1 derivative. The corresponding residue in CDK2 is F80, which is close (3.7 Å) to C(7) (K252a numbering) of 2 (FIG. 22A) in the crystal structure of CDK2 bound to staurosporine (FIG. 22B) (92). Thus, it was anticipated that developing unique indolocarbazole-based inhibitors of our sensitized kinases would require selective manipulation of C(7) in either 1 or 2 (FIG. 22A). To explore this hypothesis, total synthesis and the recently developed approach that allows for the modular assembly of 1 (FIG. 22A), as well as derivatives of 1 which are stereospecifically modified at C(7) (94, 95)

A small panel of C(7) substitute K252a derivatives were synthesized. Given that F80 of CDK2 is not coplanar with the indolocarbazole ring (FIG. 22B), it was anticipated that syntheses utilizing S-(L)-amino acids would yield K252a derivatives that would best complement the space creating mutation of F80 to glycine or alanine. In addition to the S-C(7) analogs, R-C(7)-benzyl (+)-K252a (6, FIG. 27) was prepared which, based on the binding mode prediction, was presumed to inhibit engineered protein kinases less potently than the corresponding S diastereomer (FIG. 27).

The K252a analogs described immediately above were screened for inhibition against a panel of protein kinases comprised of both tyrosine and serine/threonine kinases. The in vitro inhibition of at least one protein kinase from four distinct and physiologically important subfamilies (FIG. 26A; Src family (v-src, Fyn) (96, 97), Abl family (c-Able)(98), $Ca^{2+}$/Calmodulin dependent family (CAMK IIα) (99), and cyclin dependent family (CDK2) (100). The amino acid corresponding to 338 of v-Src was mutated to a small residue (glycine or alanine) for all of the above protein kinases (FIG. 24B, for c-Abl the T315G mutant was unstable (101)) to generate the following inhibitor sensitive kinases; I338G v-Src, T339G Fyn, T315A Abl, F89G CAMK IIα and F80G CDK2. Kinases which are sensitive to K252a and one which is not (c-Abl) were selected to represent both classes of target kinases (FIG. 27).

The K252a analogs were screened against the wild-type and engineered protein kinases for in vitro inhibition of phosphorylation of an exogenous substrate. As predicted all of the C(7) substituted K252a derivatives were much less efficient than 1 (FIG. 22A) at inhibiting the panel of wild-type protein kinases (FIG. 27). Of the five wild-type kinases, CAMK IIα is the most susceptible to inhibition by the K252a derivatives which is not surprising because it is also the most sensitive to K252a itself. For each of the kinases, the $IC_{50}$ values of the K252a analogs decreased in the presence of the mutation, confirming our prediction of the binding orientation of 1. A derivatized partner for each of the mutant kinases was found such that the binding either approached or exceeded the affinity of the wild-type kinase/1 pair. Strikingly, the 2-methyl-propyl analog (4, FIG. 27) bound to the engineered Src family kinases (v-src and c-Fyn) with sub-nanomolar $IC_{50}$ values (230 pM and 550 pM, respectively), roughly two orders of magnitude lower than the values for 1 against the same wild-type kinases. These values represent the most potent inhibition of any Src family kinase reported to date. Potent ($IC_{50}$<50 nM) and selective ($\geq$15 fold compared to all wild-type kinases in the panel) matches were found for all of the mutant kinases except for c-Abl. Abl is the only wild-type protein kinase in the panel which is not effectively inhibited by K252a, suggesting that sensitivity to 1 is a predictive determinant for whether or not other kinases (not in FIG. 26) would be well suited for inhibition by K252a analogs.

Initially, it was unclear whether the weak inhibition of T315A c-Abl was due to the β-methyl group of the alanine side chain or due to the intrinsic insensitivity of c-Abl to inhibition by 1 (FIG. 22A). To probe the effect of the β-methyl group more directly we checked another kinase with an Ala substitution. We measured the inhibition of the two most potent I338G v-Src inhibitors, 4 and 7 (FIG. 27), against I338A v-Src. The alanine mutant of v-Src has IC50 values of 0.024 and 0.43 μM, respectively, for these compounds, roughly 100 times greater than the values for I338G. However, the inhibition values differ between I338G v-Src and T315A c-Abl by more than 10,000 fold, implying that c-Abl is intrinsically less inhibitable by analogs of 1.

Generalized Inhibitor Capable of Inhibiting any Suitably Mutated Kinase: In an effort to develop a more generalizable inhibitor which could inhibit any suitably mutated kinase, a panel of wild-type and mutant kinases were tested against a group of C(3)-phenyl modified PP1 analogs. Although PP1 is Src family selective, it was reasoned that the mutation of the 338 position (v-Src) to a small amino acid may confer unique PP1 analog sensitivity to other kinases, since this amino acid was shown to be largely responsible for the selectivity of PP1 itself. From this panel of inhibitors either C(3)-1'-naphthyl PP1 (9, FIG. 28) or C(3)-1'-naphthylmethyl PP1 (11, FIG. 28) was the most potent inhibitor of every engineered kinase tested. Analysis of the PP1 analog inhibition data in FIG. 28 reveals some striking trends. PP1 yielded analogs with wider utility in the context of the engineered kinase/inhibitor pairs. Each of the five target kinases were inhibited by PP1 analogs at low nanomolar concentrations with target specificities ranging from 85 to 400 fold (measured against the most inhibitable wild-type kinase). There is little or no correlation between the wild-type PP1 $IC_{50}$ and the PP1 analog sensitivity of the same (engineered) kinase. This is most apparent in the Ser/Thr kinases CDK2 and CMK IIα. These wild-type enzymes both possess weak PP1 $IC_{50}$'s of greater than 15 μM. However the engineered versions of these kinases are very potently inhibited by the PP1 analog (11; 5.0 nM and 8.0 nM, respectively). This dichotomy is most likely due to a combination of the importance of residue 338 in determining the PP1 sensitivity of a given protein kinase (86) and the affinity of the naphthyl ring for the expanded kinase active site. The $IC_{50}$'s for 11 for all of the glycine mutants were within a 3 fold range (all <10 nM) of one another even though their wild-type PP1 sensitivities vary by more than 400 fold. Importantly, none of the wild-type kinases tested are inhibited at concentrations less than 1 μM 11, demonstrating the high target selectivity of this compound.

The PP1analogs, 10 and 11 (FIG. 28), are selective for different space-creating mutations based on their size and flexibility. The more rigid C(3)-1'naphthyl PP1 (10) shows a broader range of potency between different kinase glycine mutants (FIG. 28). However, it potently inhibits T315A c-Abl (7.0 nM) with high specificity, yielding the first mutant inhibitor of this protein tyrosine kinase (102). To determine if 10 could be generally used to inhibit protein kinases which are mutated to alanine at the 338 position we tested its potency against I338A v-src. 10 inhibits the alanine mutant v-Src ($IC_{50}$=1.0 nM) even more strongly than it inhibits the corresponding glycine mutant, suggesting that this molecule will provide a general scheme for the development of mutant inhibitors for protein kinases whose activity or stability is significantly compromised by the glycine mutation (101).

Example 18

PP1 Analog Sensitive Kinase Alleles

Subsequently, the above strategy was investigated to determine whether it could be used to generate "PP1 analog sensitive" (as) kinase alleles with in vivo utility. We have chosen this nomenclature because the same mutant kinases can be used to identify the direct cellular substrates of each kinase by use of orthogonal ATP analogs designed to complement the "as" mutation (154, 155).

It has been shown that C(3) derivatized PP1 analogs can be used for target specific inhibition of retrovirally expressed v-src in murine fibroblasts. It is, however, more interesting to demonstrate mutant inhibition of endogenous kinase gene products in an organism that has broad utility in traditional genetic screens. The budding yeast, *Saccharomyces cerevisiae*, is widely used as a unicellular model organism in genetic studies due to its susceptibility to genetic manipulation and rapid growth (103). The *S. Cerevisiae* genome encodes roughly 120 protein kinases including homologues of proteins from many mammalian kinase families (104). The yeast cyclin-dependent kinase, Cdc28, was chosen as the initial target for in vivo inhibition. This enzyme is the major CDK in budding yeast and is essential for cell viability at START and mitosis in the *S. Cerevisiae* cell cycle (105). Cdc28 is 62% identical to human CDK2, suggesting that the engineered F88G Cdc28, Cdc28-as1, should be susceptible to inhibition by C(3) derivatized PP1 analogs. Wild-type Cdc28 and Cdc28-as1 were expressed and the sensitivity of the two kinases to PP1 derivatives in vitro were investigated. As with CDK2, 11 (FIG. 28)is a very potent inhibitor of the engineered Cdc28 ($IC_{50}$=3.9 nM), but it does not inhibit the wild-type protein ($IC_{50}$=>50 μM). It was also found that the growth of yeast which express Cdc28-as1 was completely ablated at concentrations of 11 that had no effect on the growth of wild-type strains. Due to the fact that these cell lines differ by only one amino acid side chain in one protein, this selective cell cycle disruption is unambigously target specific. Moreover, the ability of 11 to easily cross the yeast cell wall is unusual and avoids the need to add extremely high concentrations of the inhibitor during assays.

To determine whether this strategy could be extended to identify analog sensitive alleles of other families of protein kinases without individually purifying and assaying every enzyme in vitro, the *Saccharomyces cerevisiae* MAP kinase, Fus3, which is required for induction of pheromone inducible genes, cell cycle arrest and cell fusion during mating was selected (106). In the presence of mating factor pheromones, Fus3 phosphorylates Far1 and Ste12. These phosphorylation events are required for G1 cell cycle arrest and transcription of genes required for mating (107, 108). No temperature sensitive (ts) alleles of Fus3 have been isolated, possibly due to the temperature sensitivity of the mating process (109).

To generate an analog sensitive allele of fus3, glutamine 93 (corresponding to I338 in v-Src) was mutated to glycine (D93G Fus 3, Fus-as1) and this enzyme was expressed in budding yeast that lacks wild-type Fus3. The fus3-as1 mutant fully complemented the gene deletion as shown by the mating of equal numbers of haploid wild-type or fus3-as1 cells (URA3 his3) to a fus1Δfus2A ura3 HIS3 strain followed by selection for diploid progeny on media lacking uracil and histidine (FIG. 23). Fus3 and Fus3-as1 expressing strains both yielded approximately $7.5 \times 10^4$ colony forming units (cfu)/ml while mating of a fus3Δ strain gave only 0–100 cfu/ml under the same selection conditions. When the mating of a fus3-as1 strain was carried out in the presence of 50 μM 10 (FIG. 28), the amount of diploids formed was indistinguishable from a fus3Δ strain (FIG. 23B–23C). Even at 500 nM 10, the fus3-as1 strain gave only $1.7 \times 10^3$ cfu/ml, a 44 fold decrease from equivalent control cells (FIG. 23C).

Due to the competition with millimolar quantities of ATP in the yeast cell, this strong inhibition at 500 nM 10 implies an in vitro $IC_{50}$ for Fus3-as1 in the low nanomolar range. 11 (FIG. 28) also disrupted Fus3-as1 mediated mating, but with less potency (85 fold decrease at 50 μM). By contrast, no decrease in mating efficiency was observed when wild-type Fus3 expressing cells were treated with 10 or 11 (0.6–1.1× $10^5$) cfu/ml at all concentrations up to 50 μM, FIG. 23C). Therefore fus3-as1 represents the first conditional allele of the MAPK, fus3. Through the in vivo addition of 10, the activity of the fus3 gene product can be controlled selectively, rapidly, and in a dose dependent fashion.

The analog sensitive alleles described here hold a number of advantages over traditional ts alleles. They are subject to stoichiometric and temporal control. Addition of a uniquely specific inhibitor should not disrupt the stability of the enzyme target or its protein-protein interactions. Inhibitor sensitized strains can be generated for genes that function in cellular processes which are inherently temperature sensitive (actin cytoskeleton rearrangement, mating, etc.) (109, 110). In addition protein kinase activity can be controlled specifically without causing the non-specific transcriptional effects that are induced by heat shock (111).

Example 19

Cdc28 Mutant Kinase Sensitive Cell-Permeable Inhibitors

METHODS

Purification of Cdc28-$His_6$, Cdc28-as1-$His_6$, MBP-Clb2: Lysate was prepared from insect cells co-infected with baculoviruses encoding Cdc28-$His_6$ or Cdc28-as 1-$His_6$ and Cak1-$HA_3$ (151). Cdc28-$His_6$ and Cdc28-as1-$His_6$ were purified by metal affinity chromatography as described (152), followed by anion-exchange (Pharmacia SP Sepharose Fast Flow) and cation-exchange (Pharmacia Q Sepharose Fast Flow). MBP-Clb2 was purified from lysates of bacteria expressing MBP-Clb2 (a gift of R. Deshaies) on an amylose column (NEBL), followed by anion-exchange chromatography (Pharmacia Q Sepharose Fast Flow).

Purified Cdc28-$His_6$ (1 nM final concentration) and MBP-Clb2 (3 nM final concentration) were incubated for 10 min at 23° C. in a 25 μl reaction mixture containing 5 μg Histone H1, 1 μCi of γ-$^{32}$P-ATP (1 μCi/10 μM and 1 μCi/1 mM), and several concentrations of 1-NM-PP1 in kinase buffer (41). Reaction products were analyzed by 15% SDS-PAGE followed by autoradiography. Phosphate incorporation was determined at each inhibitor concentration by scintillation counting. Inhibitor concentration vs. phosphate incorporation was plotted and the 1-NM-PP1 concentration at which phosphate incorporation was 50% that of the no inhibitor control was reported as the $IC_{50}$.

Yeast Plasmid and Strain Construction: Media and genetic and microbial techniques were essentially as described (148, 153). All strains were derivatives of W30-3 (ura3-a, leu2-3, 112, trpl-1, his3-11,15, ade2-1, can1-100, GAL+). All strains were grown a 23° C. unless otherwise noted. To create cdc28-as1, the CDC28 coding sequence and 400 bp of 5'-and 386 bp of 3'-flanking DNA was PCR-amplified from genomic DNA and ligated into pRS306 to make pJAU1. The F88G mutation was engineered by oligonucleotide-directed mutagenesis of pJAU1. The plasmid was integrated into the wild-type CDC28 locus following AflII digestion by a pop-in-pop-out strategy as described (148, 153).

Cdc28 and Cdc28-as1 ATP kinetics: Purified Cdc28-$His_6$ (1 nM final concentration) and MBP-Clb2 (3 nM final concentration) were incubated for 10 min at 23° C. in a 25 μl reaction mixture containing 5 μg Histone H1 and several concentrations of γ-$^{32}$P-ATP in kinase buffer (25 mM Hepes-NaOH pH 7.4, 10 mM NaCl, 10 mM $MgCl_2$, and 1 mM dithiothreitol (DTT)). Reaction products were analyzed by 15% SDS-PAGE followed by autoradiography. Phosphate incorporation was determined at each ATP concentration by scintillation counting. Eadie-Hofstee plots were then used to calculate $K_m$ and $k_{cat}$.

1-NM-PP1 $IC_{50}$ Values: Purified Cdc28-$His_6$ (1 nM final concentration) and MBP-Clb2 (3 nM final concentration) were incubated for 10 min at 23° C. in a 25 μl reaction mixture containing 5 μg Histone H1, 1 μCi of γ-$^{32}$P-ATP (1 μCi/10 μM and 1 Ci/1 mM), and several concentrations of 1-NM-PP1 in kinase buffer.

Purified Cdc28-$His_6$ (1 nM final concentration) and MBP-Clb2 (3 nM final concentration) were incubated for 10 min at 23° C. in a 25 μl reaction mixture containing 5 μg Histone H1 and several concentrations of δ-$^{32}$P-ATP in kinase buffer (25 MM Hepes-NaOH pH 7.4, 10 mM NaCl, 10 mM $MgCl_2$, and 1 mM dithiothreitol (DTT)). Reaction products were analyzed by 15% SDS-PAGE followed by autoradiography. Phosphate incorporation was determined at each ATP concentration by scintillation counting. Eadie-Hofstee plots were then used to calculate $K_m$ and $k_{cat}$.

Reaction products were analyzed by 15% SDS-PAGE followed by autoradiography. Phosphate incorporation was determined at each inhibitor concentration by scintillation counting. Inhibitor concentration vs. phosphate incorporation was plotted and the 1-NM-PP1 concentration at which phosphate incorporation was 50% that of the no inhibitor control was reported as the $IC_{50}$.

DNA flow cytometry: Approximately $1 \times 10^7$ cells for each sample were fixed in 70% ethanol, resuspended in 50 mM Tris-HCl pH 8.0, briefly sonicated, digested with 2mg/ml RNase for 2 hours at 37° C., and resuspended in 0.2 ml protease solution (5 mg/ml pepsin. 0.5% concentrated HCl) and digested for 45 minutes at 37° C. DNA was stained with 1 μM Sytox Green (Molecular Probes) in 50 mM Tris-HCl pH 7.5 and 20,000 cells from each sample were scanned with a FACScan FACS machine (Becton-Dickinson).

RESULTS

Cdc28-$His_6$ and Cdc28-as-1-$His_6$ were expressed and purified from Sf9 insect cells. They formed active complexes with purified MBP-Clb2 from bacteria. Lysate was prepared from insect cells co-infected with baculoviruses encoding Cdc28-$His_6$ or Cdc28-as1-$His_6$ and Cak1-$HA_3$ (48). Cdc28-$His_6$ and Cdc28-as1-$His_6$ were purified by metal affinity chromatography as described (49), followed by anion-exchange (Pharmacia SP Sepharose Fast Flow) and cation-exchange (Pharmacia Q Sepharose Fast Flow). MBP-Clb2 was purified from lysates of bacteria expressing MBP-Clb2 (a gift of R. Deshaies) on an amylose column (NEBL), followed by anion-exchange chromatography (Pharmacia Q Sepharose Fast Flow).

Relative to wild-type Cdc28, Cdc28-as1 displayed a moderate reduction in activity, including a 10-fold reduction in binding affinity for ATP and a 6-fold reduction in maximum ATP turnover rate (Table 4). More importantly, Cdc28-as1 was exquisitely sensitive to the inhibitor 1-NM-PP1. In the presence of 1 mM ATP, which roughly approximates intracellular ATP concentration, Cdc28-as1 was about 15,000-fold more sensitive to 1-NM-PP1 than wild-type Cdc28 ($IC_{50}$3 nM for Cdc28-as1 and 44,000 nM for Cdc28). Thus, the single substitution of a glycine for a phenylalanine results in a Cdc28 mutant that displays both high affinity and specificity for 1-NM-PP1.

To examine the function of Cdc28 in vivo, a yeast strain in which the wild-type copy of CDC28 was replaced by cdc28-as1 was constructed. Media and genetic and microbial techniques were essentially as described (148, 153). All strains were derivatives of W303 (ura3-1, leu2-3,112, trpl-1, his3-11,15, ade2-1, canl-100, GAL+). All strains we 23° C. unless otherwise noted. To create cdc28-as1, the CD C28 coding sequence and 400 bp of 5'-and 386 bp of 3'-flanking DNA was PCR-amplified from genomic DNA and ligated into pRS306 to make pJAU1. The F88G mutation was engineered by oligonucleotide-directed mutagenesis of pJAU1. The plasmid was integrated into the wild-type CDC28 locus following AflII digestion by a pop-in-pop-out strategy as described (148, 153).

In the absence of 1-NM-PP1, cdc28-as1 cells displayed normal viability and growth on plates, although they were hyperpolarized and larger than an isogeneic CDC28 strain, and had a 20% longer doubling time in liquid culture. Flow cytometric analysis of asynchronously dividing cells revealed that the cdc28-as1 and CDC28 strains displayed similar DNA content profiles. Finally, synthetic oligonucleotide DNA arrays were used to measure genome-wide transcriptional differences between asynchronous wild-type and cdc28-as1 cells (127).

Changes were deemed significant if they were greater than or equal to 2-fold or if the transcript changed present/absent status (as indicated by Affymetrix software) in the following comparisons: for non-specific drug effects: CDC28+1-NM-PP1vs. CDC28; for cdc28-as1 effects: cdc28-as1 vs. CDC28. For specific Cdc28 inhibition effects, changes were deemed significant if they were greater than or equal to 2.5-fold for cdc28-as1 1-NM-PP1 vs. Cdc28-as! AND a greater than or equal to 2.0-fold change for cdc28-as1 1-NM-PP1 vs. CDC28+1-NM-PP1.

In two separate experiments, greater than two-fold changes were observed in only eleven transcripts (0.2% of the genome). Greater than 2-fold differences were observed in expression of the following genes in a comparison of wild-type and cdc28-as1 cells:

Experiment 1: LEU2, YDL241W, YFL057C, YHR071W, CBP1 YJR130C, CWP1, YLL060c; ATR1 YML128C, YMR095C, YMR096W, YNL275W, YNR065C, ARG1, YOL101C, SPS4, SSU1, SVS1, OYE3, RLF2, and YPR203W, TWT1, YHR209W, YIL011W, YIL023C, DAL4, YKL218C, YLL060C, YLO108C, YLR237W, YLR437C, YML071C, ATR1,1, YMR095C, YMR096W, YNR065C, ARG1, YOR302W, SPS4, YPL088W, SVS1, YPR013C, CTR1.

The minor growth defect in cdc28-as1 cells was suspected to be due to the 6-fold lower $k_{cat}$ of the mutant enzyme, which would result in a 6-fold lower activity at the high ATP concentrations in vivo (the lower ATP binding affinity of the mutant should not be relevant in vivo, where ATP concentration is much greater than $K_m$). Thus, cdc28-as1 is a slightly weakened allele of CDC28 that can nevertheless support cell cycle progression.

Next, the effects of the inhibitor 1-NM-PP1 on cell growth and morphology were analyzed. Proliferation of wild-type cells was unaffected by the inhibitor except at very high concentrations (50,000 nM), when doubling times increased about 2-fold. DNA microarray analysis revealed that transcription of only 6 genes (0.1%) was changed greater than two-fold after 30 minutes treatment of wild-type cells with 500 nM 1-NM-PP1.

Of the six transcripts that changed in wild-type cells after 30 minutes of inhibitor treatment, three have no known function (YGR035C, YLR346C, YPL222W) and the others have roles in heat shock (SSA4), osmotic stress response (GRE2), and drug resistance (YOR1). The transcription of only one of these genes (YGR035C) is cell cycle regulated (150). Treatment of wild-type cells with inhibitor for 120 minutes resulted in changes in only 3 genes (YGR035C and two genes encoding ribosomal proteins: RPS26A and RPL26B).

Treatment of cells for 120 minutes caused even fewer transcriptional responses: greater than two-fold changes were seen for only three transcripts. Interestingly, no significant activation of stress-responsive transcripts was observed, consistent with the proposal that many drug-sensing mechanisms respond to the function rather than the presence of the drug (122). Therefore, it was concluded that 500 nM 1-NM-PP1 treatment has no significant effects on wild-type cell physiology, suggesting that it does not inhibit or stimulate any wild type kinase or other enzyme in yeast.

The single amino acid change in the Cdc28-as1 kinase makes it exceedingly sensitive to the inhibitor 1-NM-PP1in vivo. Growth of the cdc28-as1 strain was inhibited 50% at 50 to 100 nM inhibitor; complete growth arrest occurred above 500 nM. The close correspondence between the $IC_{50}$ in vivo and those measured in kinase assays (Table 4) illustrates the efficacy with which 1-NM-PPL can penetrate a yeast cell, a feature not exhibited by other small molecule CDK inhibitors (122).

TABLE 4

Comparison of Activity of Cdc28 and Cdc28-as1 in the Presence of an Inhibitor

| | ATP Kinetics[1/] | | | 1-NM-PP1 $IC_{50}$[2/] ($\mu$M) | |
|---|---|---|---|---|---|
| Kinase | $K_m$ ($\mu$M) | $k_{cat}$ (min$^{-1}$) | $k_{cat}/K_m$ ($\mu$M$^{-1}$·min$^{-1}$) | @10 $\mu$M ATP | @1 mM ATP |
| Cdc28•MBP-Clb2 | 35 | 132 | 3.730 | 22 | 44 |
| Cdc28-as1MBP-Cl·b2 | 322 | 21.3 | 0.066 | .0020 | .0029 |

TABLE 4-continued

Comparison of Activity of Cdc28 and Cdc28-as1
in the Presence of an Inhibitor

| | ATP Kinetics[1/] | | | 1-NM-PP1 IC$_{50}$[2/] ($\mu$M) | |
|---|---|---|---|---|---|
| Kinase | K$_m$ ($\mu$M) | k$_{cat}$ (min$^{-1}$) | k$_{cat}$/K$_m$ ($\mu$M$^{-1}$·min$^{-1}$) | @10 $\mu$M ATP | @1 mM ATP |

[1/]Purified Cdc28-His$_6$(1 nM final concentration) and MBP-Clb2 (3 nM final concentration) were incubated for 10 min at 23° C. in a 25 $\mu$l reaction mixture containing 5 $\mu$g Histone H1 and several concentrations of $\gamma$-$^{32}$P-ATP in kinase buffer (25 mM Hepes-NaOH pH 7.4, 10 mM NaCl, 10 mM MgCl$_2$, and 1 mM dithiothreitol (DTT)). Reaction products were analyzed by 15% SDS-PAGE followed by autoradiography. Phosphate incorporation was determined at each ATP concentration by scintillation counting. Eadie-Hofstee plots were then used to calculate K$_m$ and k$_{cat}$.
[2/]Purified Cdc28-His$_6$(1 nM final concentration) and MBP-Clb2 (3 nM final concentration) were incubated for 10 min at 23° C. in a 25 $\mu$l reaction mixture containing 5 $\mu$g Histone H1, 1 $\mu$ Ci of $\gamma$-$^{32}$P-ATP (1 $\mu$ Ci $\mu$M and 1$\mu$Ci/1mM), and several concentrations of 1-NM-PP1 in kinase buffer (147). Reaction products were analyzed by 15% SDS-PAGE followed by autoradiography. Phosphate incorporation was determined at each inhibitor concentration by scintillation counting. Inhibitor concentration vs. phosphate incorporation was plotted and the 1-NM-PP1 concentration at which phosphate incorporation was 50% that of the no inhibitor control was reported as the IC$_{50}$.

Cdc28-as1 is highly sensitive to 1-NM-PP1 in vitro and is a slightly weakened kinase. Active cyclin-Cdk complexes were formed by the addition of excess MPB-Clb2 to purified Cdc28-His$_6$, or Cdc28-as1-His$_6$, and their ability to phosphorylate Histone H1 at different ATP concentrations was measured to generate K$_m$ and k$_{cat}$ values. To determine IC$_{50}$, the inhibitor concentration at which the kinase is 50% inhibited, we measured the kinase activity of Cdc28 MBP-Clb2 or Cdc28-as1 MBP-Clb2 in the presence of varying concentrations of 1-NM-PP1, at two different ATP concentrations.

Detailed analysis of DNA content and morphology of cdc28-as1 cells revealed that lower concentrations of 1-NM-PP1 caused a delay (50 nM) or arrest (500 nM) with a G2/M DNA content and large hyperpolarized buds. Higher inhibitor concentrations (5,000 nM) caused a non-uniform arrest that included unbudded G1 cells as well as large-budded G2/M cells; bud hyperpolarization was no longer evident. Thus, it appears possible to titrate the level of Cdc28-as1 activity in vivo, allowing the identification of cell cycle events that are differentially sensitive to decreases in the catalytic activity of Cdc28.

When cdc28-as1 cells were synchronized in G$_1$ with the yeast mating pheromone, $\alpha$-factor, and then released into fresh media containing 500 nM 1-NM-PP1, initiation of budding and DNA synthesis were delayed about 30 to 60 minutes, while accumulation of the mitotic cyclin Clb2 was delayed 60 to 90 minutes. Cells went on to arrest with moderate Clb2 levels, highly hyperpolarized buds, and a G2/M DNA content, much like the arrest observed in asynchronous cells. Microscopic analysis of microtubules and DNA revealed that these cells lacked a mitotic spindle and arrested with a single DNA mass correctly positioned at the bud neck. Thus, cells treated with low concentrations of the inhibitor are slightly delayed during progression through early stages of the cell cycle, but eventually arrest due to a failure to assemble a mitotic spindle and enter mitosis.

When GI-synchronized cdc28-as1 cells were released into media containing 5,000 nM 1NM-PPI, they arrested with a IC DNA content and initially failed to bud, suggesting an arrest at START. These cells eventually budded after 180 to 240 minutes and arrested with a 1C. DNA content, large hyperpolarized buds, a single DNA mass in the mother cell, and an interphase astral microtubule array.

Pho85, a Cdk that is closely related to Cdc28, has been implicated in the initiation of budding in S. cerevisiae (128, 129). Therefore, the budding observed in cdc28-as1 cells released into 5,000 nM 1-NM-PP1 due to residual Cdc28-as1 activity or due to Pho85 activity was investigated. A cdc28-as1 strain lacking PCL1 and PCL2, which encode the two G1 activating cyclins of Pho85 were constructed. When these cells were synchronized in G1 and released into 5,000 nM 1-NM-PP1, they arrested with a 1C. DNA content and never budded, even after 6 hours. It was concluded that Pcl1-and Pcl2-associated Pho85 activity, and not residual Cdc28 activity, are responsible for the greatly delayed budding observed in cdc28-as1 cells treated with high concentrations of inhibitor.

To further characterize the cell cycle arrest caused by inhibitor treatment, genome-wide transcription after treatment of asynchronous cdc28-as1 cells with 500 nM 1-NM-PP1was analyzed (FIGS. 25A–D). Two hours treatment caused 2.5-fold or greater changes in the transcription of 104 genes (66 decreases, 38 increases) (FIGS. 25B and C). Of the down-regulated transcripts, 60 are cell cycle-regulated and 32 have peak expression at G2/M. This downregulated G2/M subset contains a broad range of well-established mitotic regulators, including CLB2, SW15, CDC20, and CDC5. Decreased levels of the CLB2 transcript are consistent with the delay in Clb2 accumulation following release from GI arrest. The downregulated G21M subset also included 11 transcripts of unknown function, these transcripts may encode G2/M regulators under transcriptional control by Cdc28. 30 minutes treatment with I-NM-PPI produced a similar G2/M transcriptional block (37 of the 42 down-regulated genes are cell cycle regulated and 57% of these peak at G2/M) (130).

Two-hour drug exposure also increased the expression of 38 transcripts over 2.5-fold (10 cell cycle regulated) (FIG. 25A–D). All but one of these cell cycle regulated transcripts are expressed at peak levels in G1. This group includes genes encoding G I cyclins (Cln2 an PcI I). This result, combined with the observation that the Cln-Cdc28 inhibitor Far 1 was down-regulated 20-fold, suggests that prolonged Cdc28 inhibition and G2/M arrest leads to a transcriptional program that boosts the activity of G I cyclin-Cdk complexes.

To assess general trends in the transcriptional response to Cdc28 inhibition, mean changes in the expression of all genes from each of the major cell cycle gene clusters were calculated (FIG. 25D). This analysis confirmed that inhibitor treatment of cd28-as1 cells led primarily to decreased expression of genes that are normally expressed in the G2/M and M/G1 stages of the' cell cycle.

In addition to being required for mitotic entry, Cdk1 is also known to control the exit from mitosis (131, 132). Cdk1 activity inhibits progression from anaphase to G1, and therefore Cdk1 inactivation (primarily by cyclin proteolysis) is required for mitotic exit. In addition, Cdk 1 inhibits its own inactivation in late mitosis by phosphorylating and inactivating components of the anaphase-promoting complex (APC) that targets cyclins for destruction (133, 134). If cells are arrested in mitosis with the microtubule poison nocodazole, cyclin destruction and mitotic exit can be triggered by overexpression of the Cdk inhibitory protein Sic 1 (135). Consistent with these results, treatment with 500 nM I-NM-PPI was found to lead to rapid (<60 min) cyclin destruction and rebudding of cdcM-as1 cells arrested in late mitosis with the cdc15-2 mutation (136).

Although Cdks inhibit progression from anaphase to G1, they also appear to promote APC activity and sister chromatid separation at the metaphase-to-anaphase transition (131, 132, 137). For example, genetic evidence suggests that certain weak alleles of CDC28, including cdcM-as1, display minor defects in progression through anaphase (137); in addition, one ts mutant of CDC28 (cdc28-IN) exhibits a metaphase arrest at the restrictive temperature (138). Experimental conditions where inhibitor treatment causes a metaphase arrest in cdc28-as1 cells have not been determined, presumably because low inhibitor concentrations either prevent mitotic entry or trigger premature mitotic exit. Furthermore, the metaphase arrest in cdc28-IN cells may not be due to a general decrease in kinase activity, but instead could be due to a limited defect in activity toward substrates involved in metaphase-to-anaphase progression.

Example 20

Generation of Mutant Specific Inhibitors of Lipid Kinases—Phosphatidyl Inositol-3 Phosphate Kinase (PI-3K) Alpha (α)

A family of protein kinases which phosphorylate inositol triphosphates in cells is called phosphatidyl inositol-3 phosphate kinases (PI-3K's). These proteins utilize ATP as the phosphodonor substrate. They are key regulators of cell signalling which is important in cancer.

Based on previous examples, residues in protein kinases which can be altered to allow binding of inhibitor molecules that do not inhibit any wild-type kinases have been identified. Using the methods described previously, a protein sequence alignment between protein kinases and PI-3K's is generated. This alignment is also based on the crystal structure of PI-3Kγ. Based on the structural similarity between PI-3Kγ and PI-3Kα and on the sequence alignment of protein kinases and PI-3K's, it is proposed that residue 1848 in PI-3Kα corresponds to residue I338 in v-Src. Therefore, mutating 1848 to Ala or Gly generates mutant I848A PI-3-Kα or I848G PI-3-Kα that is expected to be sensitive to the inhibitors disclosed herein.

Example 21

Generation of Mutant Specific Inhibitors of Aminoglycoside Kinases

Another family of enzymes which can be engineered by the methods previously described is the bacterial kinases which phosphorylate aminoglycoside antibiotics such as kanamycin. An example of an aminoglycoside kinase is APH (III-a').

Following the methods described previously, a sequence alignment between APH (III-a') and v-Src is generated. This alignment is also based on the crystal structure of APH (III-a'). Based on the sequence alignment, it is proposed that methionine residue 90 in APH (III-a') corresponds to I338 in v-Src. M90 in APH(III-a') is mutated to alanine and glycine to generate mutant M90A APH (III-a') or M90G APH (III-a') which is expected to be sensitive to the inhibitors of the present invention.

The foregoing detailed description has been given for clearness of understanding only and no unnecessary limitations should be understood therefrom as modifications will be obvious to those skilled in the art.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

Thus, this invention may be embodied in other forms or carried out in other ways without departing from the spirit or essential characteristics thereof. The present disclosure is therefore to be considered as in all respects illustrative and not restrictive, the scope of the invention being indicated by the appended claims, and all changes which come within the meaning and range of equivalency are intended to be embraced therein.

REFERENCES

1. T. Mustelin, *Immunity.* 1: 351 (1994).
2. M. W. Renshaw et al. *EMBO J.* 11(11): 3941 (1992).
3. G. B. Cohen et al., *Cell.* 80: 237 (1995).
4. T. Hunter, *Cell.* 50: 823 (1987).
5. E. Eiseman et al. *Nature.* 355 (1992).
6. A. W. Murray, *Chem. and Bio.* 1: 191 (1994).
7. M. F. White, Mini-Review: Structure and Function of Tyrosine Kinase Receptors. *J. Bioenergetics Biomem.* 23(1): 63 (1991).
8. T. Hunter, *Cell.* 80: 225 (1995).
9. C. L. Sawyers, *Cancer Surveys.* 15: 37 (1992).
10. G. R. Crabtree, *Ann. Rev. Biochem.* 63: 1045 (1994).
11. R. Kurzrock et al., R., *New Engl. J. Med.* 319(15): 990 (1988).
12. A. Ullrich et al., *Cell.* 61: 203 (1990).
13. J. B. Bolen et al., *FASEB.* 6: 3403 (1992).
14. P. Cicchetti et al., *Science.* 257: 803 (1992).
15. C. L. Sawyers et al., *Cell.* 77:121 (1992).
16. E. T. Kipreos et al., *Science.* 256: 382 (1992).
17. L. Velazquez et al., *Cell.* 70: 313 (1992).
18. J. Duyster et al., Proc. *Natl. Acad. Sci., USA.* 92: 1555 (1995).

19. B. B. Mayer et al., *Proc. Natl. Acad. Sci., USA.* 88: 627 (1991).
20. M. P. Kamps et al., *Cell,* 45(1): 105 (1986).
21. A. J. Muller et al., *Proc. Natl. Acad. Sci., USA.* 90: 3457 (1993).
22. B. J. Mayer et al., *Mol. Cell. Bio.* 14(5): 2883 (1994).
23. B. J. Mayer et al., *Mol. Cell. Bio.* 12(2): 609–618 (1992).
24. S. Koyama et al., *Cell.* 7: 945 (1993).
25. H. Yu et al., *Science.* 258: 1665 (1992).
26. D. Kohda et al., *Cell.* 72: 953 (1993).
27. G. Waksman et al., *Cell.* 72: 779 (1993).
28. M. J. Eck et al., *Nature.* 362: 87 (1993).
29. J. Y. J. Wang et al., *J. Biol. Chem.* 257(22): 13181 (1982).
30. P. L. Schwartzerg et al., *Cell.* 65: 1165 (1991).
31. V. L. Tybulewicz et al., *Cell.* 65: 1153 (1991).
32. J. S. Brugge et al., *Nature* 269(5626): 346 (1977).
33. R. Jove et al., *Ann. Rev. Cell. Bio.* 3: 31 (1987).
34. T. Erpel et al., *Curr. Op. In Cell Biology* 7: 176 (1995).
35. T. Pawson, *Nature* 373: 573 (1995).
36. G. Waksman et al., *Nature* 358: 646 (1992).
37. S. J. Taylor et al., *Curr. Opin. Genet. Dev.* 3:26 (1993).
38. M. T. Brown et al., *Biochemica et Biophysica Acta* 1287: 121 (1996).
39. Z. Songyang et al., *Nature* 373: 536 (1995).
40. M. P. Kamps et al., *Oncogene Res.* 3: 105 (1988).
41. A. Weijland et al., *Science* 259: 1311 (1993).
42. P. J. Belshaw et al., *Angew. Chem. Int. Ed. Engl.* 34(19): 2129 (1995).
43. T. Fujii et al., *Chem. Pharm. Bull.* 21(8): 1676 (1973).
44. M. J. Robins et al., *Biochemistry* 12(12):2179 (1993).
45. L. W. McLaughlin et al., *Synthesis,* 322–3 (1985).
46. K. Kikugawa et al., *J. Med. Chem.* 16:358–364 (1973).
47. J. Ludwig, *Acta Biochim. et Biophy. Acad. Sci. Hung.* 16: 131 (1981).
48. S. M. Hecht et al., *Biochim. Biophy. Acta* 331: 307 (1973).
49. J. Reikofski et al., *Biotech. Adv.* 10: 535 (1992).
50. B. Xu et al., *J. Biol. Chem.* 270: 29825 (1995).
51. H. Fukazawa et al., *Analytical Biochemistry* 212: 106 (1993).
52. T. R. Lee et al., *J. Biol. Chem.* 270(10): 5375 (1995).
53. A. P. Kwiakowski et al., *Biochemistry* 26: 7636 (1987).
54. S. R. Hubbard et al., *Nature* 372: 746 (1994).
55. M. Mohammadi et al., *Cell* 86: 577 (1996).
56. J. Zheng et al., *Biochemistry* 32: 2154 (1993).
57. P. D. Jeffrey et al., *Nature* 376: 313 (1995).
58. M. P. Kamps, et al., *Nature* 310: 589–592 (1984).
59. M. J. Zoller et al., *J. Biol. Chem.* 256: 10837–10842 (1981).
60. S. S. Taylor, *Structure* 2: 345–355 (1995).
61. J. E. DeClue et al., *J. Virol.* 63(2): 542–554 (1989).
62. C. Seidel-Dugan et al., *Mol. Cell Biol.* 12(14): 1835–45 (1992).
63. A. D. Czernilofsky et al., *Nature (London)* 287: 198–200 (1980).
64. A. Fersht, Enzyme *Structure and Mechanism* 2: 475 (1985).
65. T. Hunter et al., *Proc. Nature Acad. Sci.* USA 77(3): 1311–1315. (1980).
66. K. Ozawa et al., *J. Biol. Chem.* 268(3): 1749–1756 (1993).
67. C. Schultz et al., , *Mol. Pharm.* 46: 702–708 (1994).
68. E. A. Merritt et al., *Acta Cryst.* D50: 869–873 (1994).
69. D. J. Bacon et al., *J. Molec. Graphics* 6: 219–220 (1988).
70. G. Schluckebeir et al., *Mol. Biol.* 247: 16–20 (1995).
71. G. Hardie et al., *Protein Kinase Facts Book* 0-12-324719-5. (1995).
72. A. Lehninger et al., *Principles of Biochemistry* 2: 500–4.
73. C. R. Faltynek, et al., *Biochemistry* 34: 12404–10. (1995).
74. J. Hanke, et al., *Biol. Chem.* 271: 695–701 (1996).
75. B. J. Druker, et al., *Nat. Med.* 5: 561–6 (1996).
76. U. Hanefeld et al., *J. Chem. Soc.Perkin Trans* 1: 1545–1552 (1996).
77. J. Reikofski et al., *Biotech. Adv.* 10: 535–554 (1992).
78. B. Xu et al., *J. Biol. Chem.* 270: 29825–29830 (1995).
79. K. Shah et al., *Proc. Nat. Acad. Sci.* 94: 3565–3570 (1997).
80. J. P. Morgenstern et al., *Nucleic Acids Res.* 18: 3587–3596 (1990).
81. W. S. Pear et al., *Proc. Natl. Acad. Sci. USA* 90: 8392–8396 (1993).
82. O. Danos et al., *Proc. Natl. Acad. Sci. USA* 85: 6460–4 (1988).
83. T. R. Lee et al., *J. Biol. Chem.* 270: 5375–5380 (1995).
84. P. M. Coussens et al., *Molecular and Cell. Biol.:* 2753–2763. (1985).
85. J. H. Hanke et al., *J. Biol. Chem.* 271: 695 (1996).
86. Y. Liu et al., *Chem. Biol.* 6, 671 (1999).
87. J. Waltenberger et al., *Circ. Res.* 85, 12 (1999).
88. S. K. Hanks and A. M. Quinn, *Meth. Enzymol.* 200, 38 (1991).
89. S. Omura, Y. Sasaki, Y. Iwai, H. Takeshima, *J. Antibiot. (Tokyo)* 48, 535 (1995).
90. L. F. Tapley P, Barbacid M, *Oncogene* 7, 371 (1992).
91. L. Prade et al., *Structure* 5, 1627 (1997).
92. A. M. Lawrie et al., *Nat. Struct. Biol.* 4, 796 (1997).
93. X. Zhu et al., *Structure Fold Des.* 7, 651 (1999).
94. J. L. Wood et al., *J. Am. Chem. Soc.* 119, 9641 (1997).
95. J. L. Wood et al., *Synthesis* SI, 1529 (1999).
96. M. T. Brown et al. *Biophys. Acta* 1287, 121 (1996).
97. M. D. Resh, *Int. J. Biochem. Cell Biol.* 30, 1159 (1998).
98. P. Laneuville, *Semin. Immunol.* 7, 255 (1995).
99. P. T. Kelly, *Mol. Neurobiol.* 5, 153 (1991).
100. D. O. Morgan, *Nature* 374, 131 (1995).
101. Y. Liu et al., unpublished material.
102. B. J. Druker et al., *Nat. Med.* 2, 561 (1996).
103. D. Botstein et al., *Science* 240, 1439 (1988).
104. T. Hunter et al., *Trends Biochem. Sci.* 22, 18 (1997).
105. M. D. Mendenhall et al., *Microbiol Mol. Biol. Rev.* 62, 1191 (1998).
106. H. A. Fujimura, *J. Cell. Sci.* 107, 2617 (1994).
107. M. Tyers et al., *Mol. Cell. Biol.* 13, 5659 (1993).
108. A. Gartner et al., *Mol. Cell. Biol.* 18, 3681 (1998).
109. S. Doi et al., *Arch Microbiol* 114, 287 (1977).
110. P. A. Delley et al., *J. Cell Biol.* 147, 163 (1999).
111. D. A. Lashkari et al., *Proc. Natl Acad. Sci USA* 94, 13057 (1997).
112 D. O. Morgan, *Annu. Rev. Cell Dev. Biol.* 13, 261–291 (1997).
113. D. J. Lew et al., *The Molecular and cellular biology of the yeast Saccharomyces cerevisiae,* 3, 607–95.
114. S. 1. Reed, *Genetics* 95, 561–577 (1980).
115. P. Nurse, Nature 344, 503–508 (1990).
116. R. W. King et al., *Cell* 79, 563–571 (1994).
117. S. 1. Reed et al., *Proc. Natl. Acad. Sci.* USA 87, 5697–570 1 (1990).
118. S. 1. Reed et al., *Proc. Natl. Acad. Sci.* USA 82, 4055–4059 (1985).
119. T. J. Mitchison, *Chem. Biol.* 1, 3–6 (1994).
120. S. L. Schreiber, *Bioorg. Med. Chem.* 6, 1127–1152 (1998).
121. N. Gray et al., *Curr. Med. Chem.* 6, 859 875 (1999).
122. N. S. Gray, et al., submitted for publication (1998).

123. A. C. Bishop, et al., *Curr. Biol.* 8, 257–66 (1998).
124. A. C. Bishop, et al., *J. Am. Chem. Soc.* 121, 627–631 (1999).
125. A. C. Bishop, et al., co-submitting for publication (2000).
126. K. Shah et al., *Proc. Natl. Acad. Sci. USA* 94, 3565–70 (1997).
127. L. Wodicka et al., *Nat. Biotechnol.* 15, 1359–1367 (1997).
128. F. H. Espinoza, et al. *Science* 266, 1388–1891 (1994).
129. V. Measday et al., *Science* 266, 1391–1395 (1994).
130. A. C. Bishop et al., unpublished data, available from authors upon request.
131. R. W. King, et al., *Science* 274, 1652–1659 (1996).
132. D. O. Morgan, *Nature Cell Biol.* 1, E47–E53 (1999).
133. W. Zachariae et al., *Science* 282, 1721–1724 (1998).
134. S. L. Jaspersen et al., *Curr. Biol.* 9, 227–236 (1999).
135. A. Amon, *EMBO J.* 16, 2693–2702 (1997).
136. J. A. Ubersax et al., unpublished data.
137. A. Rudner et al., submitted for publication (2000).
138. U. Surana et al., *Cell* 65, 145–161 (1991).
139. I. Fitch et al., *Mol. Biol. Cell* 3, 805–18 (1992).
140. B. Stem et al., *Trends in Genetics* 12, 345–350 (1996).
141. K. Levine et al., Mol. Cell. Bio. 16, 6794–803 (1996).
142. K. Levine et al., Mol. Cell. Biol. 18, 290–302 (1998).
143. F. R. Cross et al., *Mol. Cell* 4, 11–19 (1999).
144. A. C. Bishop et al., unpublished data.
145. H. D. Madhani et al., *Cell* 91, 673–84 (1997).
146. Y. Liu et al., *Chem. Biol.* 5, 91–101 (1998).
147. M. R. Gerber et al., *Proc. Natl. Acad. Sci. USA* 92, 4651–4655 (1995).
148. M. Rose et al.,Cold Spring Harbor Laboratory Press, Cold Spring Harbor, N.Y., (1990).
149. S. Biggins et al., *Genes Dev.* 13, 532–44 (i999).
150. P. T. Spellman et al.,*Mol. Biol. Cell* 9, 3273–97 (1998).
151. A. Farrell et al., *Mol. Cell. Biol.* in press, (2000).
152. K. K. Kim et al., *Nature Struct. Biol.* 3, 849–855 (1996).
153. F. Sherman et al., *Methods in yeast genetics* (Cold Spring Harbor Laboratory Press, Cold Spring Harbor, N.Y., 1974).
154. Y. Liu et al., *Chem. Biol.* 5, 91, (1998).
155. K. Shah et al., *Proc. Natl. Acad. Sci. USA* 94, 3565 (1997).
156. G. M. Rubin et al., *Nucl. Acids Res.* 11, 6341–6351 (1983).
157. G. M. Rubin et al., *Science* 218, 348 (1982).

What is claimed is:

1. A protein kinase inhibitor represented by the following formula I:

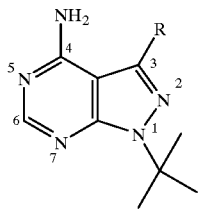

wherein R is a 1'-naphthyl; 2'-naphthyl; m-phenoxyphenyl; m-benzyloxyphenyl; m-(2',6'-dichloro)benzyloxyphenyl; 3-piperonylpyrazolo; 1'-naphthylmethyl; 1'-napthoxymethyl; or 2'-naphthylmethyl.

2. A protein kinase inhibitor of claim 1, wherein R is 1'-naphthyl.

3. A protein kinase inhibitor of claim 1, wherein R is 2'-naphthyl.

4. A protein kinase inhibitor of claim 1, wherein R is 1'-napthyhnethyl.

5. A protein kinase inhibitor of claim 1, wherein R is 2'-napthylmethyl.

6. A composition comprising the protein kinase inhibitor of any of claim 1–5 and a carrier.

7. A method of inhibiting phosphorylation of a substrate of a mutant protein kinase comprising incubating an inhibitor of claim 1 with a mixture containing the mutant protein kinase and its substrate.

8. The method of claim 7, wherein the mutant protein kinase is a mutant protein kinase of the Src family.

9. The method of claim 8, wherein the mutant protein kinase is a mutant v-Src.

10. The method of claim 9, wherein the mutant v-Src is I338G v-Src.

11. The method of claim 7, wherein the mutant protein kinase is a mutant Fyn.

12. The method of claim 11, wherein the mutant Fyn is T339G Fyn.

13. The method of claim 7, wherein the mutant protein kinase is a mutant c-Abl.

14. The method of claim 13, wherein the mutant c-Abl is T315A Abl.

15. The method of claim 7, wherein the mutant protein kinase is a mutant CAMK IIα.

16. The method of claim 15, wherein the mutant CAMK IIα is F89G CAMK IIα.

17. The method of claim 7, wherein the mutant protein kinase is a mutant CDK2.

18. The method of claim 17, wherein the mutant CDK2 is F80G CDK2.

19. The method of claim 7, wherein the mutant protein kinase is a mutant Cdc28.

20. The method of claim 19, wherein the mutant Cdc28 is Cdc28-as1.

21. The method of claim 7, wherein the mutant protein kinase is a mutant Fus3.

22. The method of claim 21, wherein the mutant Fus3 is Fus-as1.

23. A method of inhibiting a catalytic activity of a mutant protein kinase comprising incubating the mutant protein kinase with an inhibitor of claim 1.

24. The method of claim 23, wherein the mutant protein kinase is a mutant protein kinase of the Src family.

25. The method of claim 24, wherein the mutant protein kinase is a mutant v-Src.

26. The method of claim 25, wherein the mutant v-Src is I338G v-Src.

27. The method of claim 23, wherein the mutant protein kinase is a mutant Fyn.

28. The method of claim 27, wherein the mutant Fyn is T339G Fyn.

29. The method of claim 23, wherein the mutant protein kinase is a mutant c-Abl.

30. The method of claim 29, wherein the mutant c-Abl is T315A Abl.

31. The method of claim 23, wherein the mutant protein kinase is a mutant CAMK IIα.

32. The method of claim 31, wherein the mutant CAMK IIα is F89G CAMK IIα.

33. The method of claim 23, wherein the mutant protein kinase is a mutant CDK2.

34. The method of claim 33, wherein the mutant CDK2 is F80G CDK2.

35. The method of claim 23, wherein the mutant protein kinase is a mutant Cdc28.

36. The method of claim 35, wherein the mutant Cdc28 is Cdc28-as1.

37. The method of claim 23, wherein the mutant protein kinase is a mutant Fus3.

38. The method of claim 37, wherein the mutant Fus3 is Fus-as1.

39. A method of inhibiting growth of a cell that expresses a mutant protein kinase comprising incubating the cell with an inhibitor of claim 1.

40. The method of claim 34, wherein the mutant protein kinase is a mutant v-Src.

41. The method of claim 40, wherein the mutant v-Src is I338G v-Src.

42. The method of claim 34, wherein the mutant protein kinase is a mutant c-Abl.

43. The method of claim 42, wherein the mutant c-Abl is T315A Abl.

44. The method of claim 34, wherein the mutant protein kinase is a mutant CDK2.

45. The method of claim 44, wherein the mutant CDK2 is F80G CDK2.

46. The method of claim 34, wherein the mutant protein kinase is a mutant Cdc28.

47. The method of claim 46, wherein the mutant Cdc28 is Cdc28-as1.

48. A method of disrupting transformation in a cell that expresses a mutant protein kinase comprising contacting the cell with an inhibitor of claim 1.

49. The method of claim 48, wherein the mutant protein kinase is a mutant protein kinase of the Src family.

50. The method of claim 49, wherein the mutant protein kinase is a mutant v-Src.

51. The method of claim 50, wherein the mutant v-Src is I338G v-Src.

52. The method of claim 48, wherein the mutant protein kinase is T339G Fyn.

53. A method of disrupting transformation in a cell that expresses a mutant protein kinase comprising contacting the cell with a composition comprising an inhibitor of claim 1.

54. The method of claim 53, wherein the mutant protein kinase is a mutant protein kinase of the Src family.

55. The method of claim 54, wherein the mutant protein kinase is a mutant v-Src.

56. The method of claim 55, wherein the mutant v-Src is I338G v-Src.

57. The method of claim 53, wherein the mutant protein kinase is T339G Fyn.

58. A method of inhibiting phosphorylation of a substrate of a mutant protein kinase comprising incubating a composition comprising an inhibitor of claim 1 with a mixture containing the mutant protein kinase and its substrate.

59. A method of inhibiting a catalytic activity of a mutant protein kinase comprising incubating the mutant protein kinase with a composition comprising an inhibitor of claim 1.

60. A method of inhibiting growth of a cell that expresses a mutant protein kinase comprising incubating the cell with a composition comprising an inhibitor of claim 1.

* * * * *